United States Patent
Zorniak et al.

(10) Patent No.: US 11,780,932 B2
(45) Date of Patent: Oct. 10, 2023

(54) ANTIBODIES TARGETING GLIOBLASTOMA STEM-LIKE CELLS AND METHODS OF USE THEREOF

(71) Applicant: Wisconsin Alumni Research Foundation, Madison, WI (US)

(72) Inventors: Michael Zorniak, San Diego, CA (US); Paul A. Clark, Madison, WI (US); Yongku Peter Cho, Storrs, CT (US); Benjamin J. Umlauf, Madison, WI (US); Eric V. Shusta, Madison, WI (US); John Shu-Shin Kuo, Austin, TX (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 557 days.

(21) Appl. No.: 16/754,677

(22) PCT Filed: Oct. 9, 2018

(86) PCT No.: PCT/US2018/054952
§ 371 (c)(1),
(2) Date: Apr. 8, 2020

(87) PCT Pub. No.: WO2019/074892
PCT Pub. Date: Apr. 18, 2019

(65) Prior Publication Data
US 2020/0354472 A1    Nov. 12, 2020

Related U.S. Application Data

(60) Provisional application No. 62/569,834, filed on Oct. 9, 2017.

(51) Int. Cl.
| | | |
|---|---|---|
| *C07K 16/30* | (2006.01) | |
| *A61K 49/00* | (2006.01) | |
| *G01N 33/574* | (2006.01) | |
| *A61K 39/00* | (2006.01) | |

(52) U.S. Cl.
CPC ...... *C07K 16/3053* (2013.01); *A61K 49/0058* (2013.01); *G01N 33/57407* (2013.01); *A61K 2039/505* (2013.01); *C07K 2317/565* (2013.01); *C07K 2317/622* (2013.01); *C07K 2317/92* (2013.01)

(58) Field of Classification Search
None
See application file for complete search history.

(56) References Cited

U.S. PATENT DOCUMENTS

| | | |
|---|---|---|
| 2008/0019984 A1 | 1/2008 | Shusta |
| 2013/0287748 A1 | 10/2013 | June |
| 2015/0196663 A1 | 7/2015 | Shusta |
| 2017/0174778 A1 | 6/2017 | Shusta |

FOREIGN PATENT DOCUMENTS

| | | |
|---|---|---|
| WO | 2007143711 A2 | 12/2007 |
| WO | 2012075037 A1 | 6/2012 |
| WO | 2014033074 A1 | 3/2014 |
| WO | 2014099671 A1 | 6/2014 |
| WO | 2015101586 A1 | 7/2015 |
| WO | 2017120998 A1 | 7/2017 |

OTHER PUBLICATIONS

Zhu et al. (Molecular Cancer Therapeutics, vol. 9, No. 7, Jul. 2010, pp. 2131-2141) (Year: 2010).*
Almagro & Fransson, Frontiers in Bioscience 2008; 13:1619-33 (Year: 2008).*
De Genst et al., Dev Comp Immunol 2006; 30:187-98 (Year: 2006).*
Yoshinaga et al., J. Biochem 2008; 143:593-601 (Year: 2008).*
Ackerman, M. et al. Highly avid magnetic bead capture: an efficient selection method for de novo protein engineering utilizing yeast surface display. Biotechnology progress 25, 774-783, doi:10.1002/btpr.174 (2009).
Altschul, SF et al., "Gapped BLAST and PSI-BLAST: a new generation of protein database search programs." Nucleic Acids Res. 25 (1997): 3389-3402.
Arnold, A. E., et al. "Antibody-antisense oligonucleotide conjugate downregulates a key gene in glioblastoma stem cells." Molecular Therapy-Nucleic Acids 11 (2018): 518-527.
Beck, S., et al. "Identification of a peptide that interacts with Nestin protein expressed in brain cancer stem cells." Biomaterials 32.33 (2011): 8518-8528.
Boder, E. T., et al. "Yeast surface display for screening combinatorial polypeptide libraries." Nature biotechnology 15.6 (1997): 553-557.
Boder, E. T., et al. Yeast surface display for directed evolution of protein expression, affinity, and stability. Methods in enzymology 328, 430-444 (2000).
Burns ML, et al. Directed evolution of brain-derived neurotrophic factor for improved folding and expression in *Saccharomyces cerevisiae*. Applied and environmental microbiology. 2014;80:5732-5742. doi: 10.1128/AEM.01466-14.
Chen, R. et al. A hierarchy of self-renewing tumor-initiating cell types in glioblastoma. Cancer cell 17, 362-375, doi:10.1016/j.ccr.2009.12.049 (2010).
Chen, Y, et al. "The oligodendrocyte-specific G protein-coupled receptor GPR17 is a cell-intrinsic timer of myelination." Nature neuroscience 12.11 (2009): 1398-1406.
Cho YK, et al. A yeast display immunoprecipitation method for efficient isolation and characterization of antigens. Journal of immunological methods. 2009;341:117-126. doi: 10.1016/j.jim.2008.11.005.
Choi BD, et al. Systemic administration of a bispecific antibody targeting EGFRvIII successfully treats intracerebral glioma. Proceedings of the National Academy of Sciences of the United States of America. 2013;110:270-275. doi: 10.1073/pnas.1219817110.

(Continued)

*Primary Examiner* — Meera Natarajan
(74) *Attorney, Agent, or Firm* — Quarles & Brady, LLP

(57) ABSTRACT

The present invention provides antibodies that target glioblastoma stem-like cells and methods and kits for their use.

34 Claims, 17 Drawing Sheets
Specification includes a Sequence Listing.

(56) References Cited

OTHER PUBLICATIONS

Clark PA, et al. "SC-003. Identification of Glioblastoma Cancer Stem-Like Cell-Binding Human Antibodies Via Yeast Expression Library Biopanning." Neuro-oncology 15.suppl_3 (2013).
Clark PA, et al. Activation of multiple ERBB family receptors mediates glioblastoma cancer stem-like cell resistance to EGFR-targeted inhibition. Neoplasia 14, 420-428 (2012).
Clark PA, et al. Analysis of Cancer-Targeting Alkylphosphocholine Analogue Permeability Characteristics Using a Human Induced Pluripotent Stem Cell Blood-Brain Barrier Model. Mol Pharm 13, 3341-3349, doi:10.1021/acs.molpharmaceut.6b00441 (2016).
Clark PA, et al. Developmental signaling pathways in brain tumor-derived stem-like cells. Dev Dyn 236, 3297-3308, doi:10.1002/dvdy.21381 (2007).
Clark PA, et al. Resveratrol targeting of AKT and p53 in glioblastoma and glioblastoma stem-like cells to suppress growth and infiltration. J Neurosurg, 1-13, doi:10.3171/2016.1.JNS152077 (2016).
Clement V, et al. Marker independent identification of glioma initiating cells. Nature methods. 2010;7:224-228. doi: 10.1038/nmeth.1430.
Cross, R. Controlling CAR-T: How scientists plan to make the engineered T cell therapy safer, and work for more cancers. Chemical & Engineering News, vol. 96, Issue 19. 2018.
Ebben, J. D., et al. "Introduction to induced pluripotent stem cells: advancing the potential for personalized medicine." World neurosurgery 76.3-4 (2011): 270-275.
Ebben, J. D., et al. "The cancer stem cell paradigm: a new understanding of tumor development and treatment." Expert opinion on therapeutic targets 14.6 (2010): 621-632.
Feldhaus MJ, et al. Flow-cytometric isolation of human antibodies from a nonimmune *Saccharomyces cerevisiae* surface display library. Nature biotechnology. 2003;21:163-170. doi: 10.1038/nbt785.
Finzsch, M., et al. "Sox9 and Sox10 influence survival and migration of oligodendrocyte precursors in the spinal cord by regulating PDGF receptor a expression." Development 135.4 (2008): 637-646.
Galli, R. et al. Isolation and characterization of tumorigenic, stem-like neural precursors from human glioblastoma. Cancer research 64, 7011-7021, doi:64/19/7011 (2004).
Gavrilyuk, JI et al. ß-Lactam-based Approach for Chemical Programming of Aldolast Antibody 38C2, Bioorg Med Chem Lett. Mar. 1, 2009; 19(5):1421-1424.
Gurney, A., et al. "Wnt pathway inhibition via the targeting of Frizzled receptors results in decreased growth and tumorigenicity of human tumors." Proceedings of the National Academy of Sciences 109.29 (2012): 11717-11722.
Hackel BJ, et al. Production of soluble and active transferrin receptor-targeting single-chain antibody using *Saccharomyces cerevisiae*. Pharmaceutical research. 2006;23:790-797. doi: 10.1007/s11095-006-9778-7.
Hamblett KJ, et al. AMG 595, an Anti-EGFRvIII Antibody-Drug Conjugate, Induces Potent Antitumor Activity against EGFRvIII-Expressing Glioblastoma. Molecular cancer therapeutics. 2015;14:1614-1624. doi: 10.1158/1535-7163. MCT-14-1078.
Hegi, M. E., et al. "MGMT gene silencing and benefit from temozolomide in glioblastoma." New England Journal of Medicine 352.10 (2005): 997-1003.
Hjelmeland, A. B. et al. "The quest for self-identity: not all cancer stem cells are the same." Clinical Cancer Research 18.13 (2012): 3495-3498.
Homma T, et al. Correlation among pathology, genotype, and patient outcomes in glioblastoma. Journal of neuropathology and experimental neurology. 2006;65:846-854. doi: 10.1097/01.jnen.0000235118.75182.94.
Hoogenboom HR. Selecting and screening recombinant antibody libraries. Nature biotechnology. 2005;23:1105-1116. doi: 10.1038/nbt1126.
Huang, D., et al. Increasing yeast secretion of heterologous proteins by regulating expression rates and post-secretory loss. Biotechnol Bioeng 101, 1264-1275, doi:10.1002/bit.22019 (2008).
Huse, J. T. et al. "Targeting brain cancer: advances in the molecular pathology of malignant glioma and medulloblastoma." Nature reviews cancer 10.5 (2010): 319-331.
Ignatova TN, et al. Human cortical glial tumors contain neural stem-like cells expressing astroglial and neuronal markers in vitro. Glia. 2002;39:193-206. doi: 10.1002/glia.10094.
International Searching Authority, International Search Report and Written Opinion for application PCT/US2018/054952, dated Feb. 4, 2019.
Jones, A.R. et al, Blood-brain barrier transport of therapeutics via receptor-mediation. Pharmaceutical Research, 2007. 24(9): p. 1759-1771.
Karlin, S. et al. "Methods for assessing the statistical significance of molecular sequence features by using general scoring schemes." Proceedings of the National Academy of Sciences 87.6 (1990): 2264-2268.
Kim, T-M, et al. "A developmental taxonomy of glioblastoma defined and maintained by MicroRNAs." Cancer research 71.9 (2011): 3387-3399.
Kim, Y, et al. "Aptamer identification of brain tumor-initiating cells." Cancer research 73.15 (2013): 4923-4936.
Kreitman, R. J., et al. "Efficacy of the anti-CD22 recombinant immunotoxin BL22 in chemotherapy-resistant hairy-cell leukemia." New England Journal of Medicine 345.4 (2001): 241-247.
Kreitman, R. J., et al. "Phase I trial of anti-CD22 recombinant immunotoxin moxetumomab pasudotox (CAT-8015 or HA22) in patients with hairy cell leukemia." Journal of Clinical Oncology 30.15 (2012): 1822.
Krenciute G, et al. Characterization and Functional Analysis of scFv-based Chimeric Antigen Receptors to Redirect T Cells to IL13Ralpha2-positive Glioma. Mol Ther. 2016;24:354-363. doi: 10.1038/mt.2015.199.
Lee, J. et al. "Tumor stem cells derived from glioblastomas cultured in bFGF and EGF more closely mirror the phenotype and genotype of primary tumors than do serum-cultured cell lines." Cancer cell 9.5 (2006): 391-403.
Lin, J., et al. "Cadherin-19 expression is restricted to myelin-forming cells in the chicken embryo." Neuroscience 165.1 (2010): 168-178.
Lipovsek D, et al. Selection of horseradish peroxidase variants with enhanced enantioselectivity by yeast surface display. Chemistry & biology. 2007;14:1176-1185. doi: 10.1016/j.chembiol.2007.09.008.
Liu, G. et al. Analysis of gene expression and chemoresistance of CD133+ cancer stem cells in glioblastoma. Molecular cancer. 2006;5:67. doi: 10.1186/1476-4598-5-67.
Liu, H. et al. *Saccharomyces cerevisiae* S288C has a mutation in FLO8, a gene required for filamentous growth. Genetics 144, 967-978 (1996).
Liu, HL et al. Focused Ultrasound Enhances Central Nervous System Delivery of Bevacizumab for Malignant Glioma Treatment. Radiology. 2016;281:99-108. doi: 10.1148/radiol.2016152444.
Liu, JK et al. "Phage display discovery of novel molecular targets in glioblastoma-initiating cells." Cell Death & Differentiation 21.8 (2014): 1325-1339.
Liu, R. et al. Intracarotid delivery of oncolytic HSV vector G47Delta to metastatic breast cancer in the brain. Gene therapy. 2005;12:647-654. doi: 10.1038/sj.gt.3302445.
Zorniak, M. et al. Mining a Yeast Antibody Library for Glioblastoma Cancer Stem Cell-Specific Surface Markers. Poster presented at 2009 AACR conference. Denver, CO. 2009.
Zorniak, M. et al. Myelin-forming cell-specific cadherin-19 is a marker for minimally infiltrative glioblastoma stem-like cells. J Neurosurg 122, 69-77, doi:10.3171/2014.9.JNS132373 (2015).
Zorniak, M. et al. scFv-Based Detection and Isolation of Invasive Glioblastoma Cancer Stem-Like Cells from a Yeast Antibody Library. Presented at PEGS Conference 2013. Boston, MA.
Zorniak, M. Identifying Biomarkers and Antibodies for Brain Cancer and their Stem-Like Cells. Campus Stem Cell Lab Meeting. Mar. 20, 2012.
Zorniak, M. Membrance Proteomics of Human Glioblastoma Stem-Like Cells. Dissertation. University of Wisconsin-Madison. 2013.

(56) References Cited

OTHER PUBLICATIONS

Zorniak, M. Membrane Proteomics of Human Glioblastoma Stem-Like Cells. Presentation at 2013 Neurosurgery Research Day. Oct. 15, 2013. University of Wisconsin-Madison.
Zorniak, M. Strategies for Precision Medicine in Brain Cancer. Presentation at Hostage Brain Conference. Lake Forest College. Dec. 8, 2012.
Bao, S. et al. Glioma stem cells promote radioresistance by preferential activation of the DNA damage response. Nature 444, 756-760, doi:10.1038/nature05236 (2006).
Lockman PR, et al. Heterogeneous blood-tumor barrier permeability determines drug efficacy in experimental brain metastases of breast cancer. Clinical cancer research: an official journal of the American Association for Cancer Research. 2010;16:5664-5678. doi: 10.1158/1078-0432.CCR-10-1564.
Marasco, W.A., et al., 2007. The growth and potential of human antiviral monoclonal antibody therapeutics. Nature biotechnology 25, 1421-1434.
Marshall CJ, et al. An evolved Mxe GyrA intein for enhanced production of fusion proteins. ACS Chem Biol. 2015;10:527-538. doi: 10.1021/cb500689g.
Martin, CR, et al., Nanomaterials in Analytical Chemistry, Analytical Chemistry News & Features, May 1, 1998; pp. 322 A-327 A.
Minniti, G., et al. "Chemotherapy for glioblastoma: current treatment and future perspectives for cytotoxic and targeted agents." Anticancer Research 29.12 (2009): 5171-5184.
Myllykoski, M., et al. "Myelin 2', 3'-cyclic nucleotide 3'-phosphodiesterase: active-site ligand binding and molecular conformation." PloS one 7.2 (2012): e32336.
Oh, P., et al. "Subtractive proteomic mapping of the endothelial surface in lung and solid tumours for tissue-specific therapy." Nature 429.6992 (2004): 629-635.
Pardridge W.M. CSF, blood-brain barrier, and brain drug delivery. Expert Opin Drug Deliv. 2016;13:963-975. doi: 10.1517/17425247. 2016.1171315.
Ardridge W.M. Re-engineering therapeutic antibodies for Alzheimer's disease as blood-brain barrier penetrating bi-specific antibodies. Expert Opin Biol Ther, 1-14, 10.1080/14712598.2016.1230195 (2016).
Pepper, LR, et al. "A decade of yeast surface display technology: where are we now?." Combinatorial chemistry & high throughput screening 11.2 (2008): 127-134.
Pointer, KB, et al. Administration of non-torsadogenic human Ether-a-go-go Related Gene (hERG) inhibitors are associated with better survival for high hERG-expressing glioblastoma patients. Clinical cancer research : an official journal of the American Association for Cancer Research, doi:10.1158/1078-0432.CCR-15-3169 (2016).
Pointer, KB, et al. Glioblastoma cancer stem cells: Biomarker and therapeutic advances. Neurochem Int. 2014;71:1-7.
Pollard, S. M. et al. Glioma stem cell lines expanded in adherent culture have tumor-specific phenotypes and are suitable for chemical and genetic screens Cell stem cell 4, 568-580, doi:S1934-5909(09)00149-0 (2009).
Rapoport SI. Osmotic opening of the blood-brain barrier: principles, mechanism, and therapeutic applications. Cellular and molecular neurobiology. 2000;20:217-230. doi: 10.1023/A:1007049806660.
Richman SA, et al. Development of a novel strategy for engineering high-affinity proteins by yeast display. Protein engineering, design & selection: PEDS. 2006;19:255-264. doi: 10.1093/protein/gzl008.
Rodgers, D. T., et al. "Switch-mediated activation and retargeting of CAR-T cells for B-cell malignancies." Proceedings of the National Academy of Sciences 113.4 (2016):E459-E468.
Shiina S, et al. CAR T Cells Targeting Podoplanin Reduce Orthotopic Glioblastomas in Mouse Brains. Cancer Immunol Res. 2016;4:259-268. doi: 10.1158/2326-6066.CIR-15-0060.
Shusta E. V., et al. Directed evolution of a stable scaffold for T-cell receptor engineering. Nature biotechnology 18, 754-759, doi:10. 1038/77325 (2000).
Shusta, E. V., et al. Increasing the secretory capacity of Saccharomyces cerevisiae for production of single-chain antibody fragments. Nature biotechnology 16, 773-777, doi:10.1038/nbt0898-773 (1998).
Singh SK, et al. Identification of a cancer stem cell in human brain tumors. Cancer research. 2003;63:5821-5828.
Singh SK, et al. Identification of human brain tumour initiating cells. Nature. 2004;432:396-401. doi: 10.1038/nature03128.
Son MJ, et al. SSEA-1 is an enrichment marker for tumor-initiating cells in human glioblastoma. Cell stem cell. 2009;4:440-452. doi: 10.1016/j.stem.2009.03.003.
Stupp R, et al. Maintenance Therapy With Tumor-Treating Fields Plus Temozolomide vs Temozolomide Alone for Glioblastoma: A Randomized Clinical Trial. JAMA: the journal of the American Medical Association. 2015;314:2535-2543. doi: 10.1001/jama.2015. 16669.
Stupp R, et al. Radiotherapy plus concomitant and adjuvant temozolomide for glioblastoma. N Engl J Med 352, 987-996, doi:352/10/987 (2005).
Sugano, M, et al., Antibody Targeting of Doxorubicin-loaded Liposomes Suppresses the Growth and Metastatic Spread of Established Human Lung Tumor Xenografts in Severe Combined Immunodeficient Mice, Cancer Research 60, 6942-6949, Dec. 15, 2000.
Sukhanova, A, et al. "Oriented conjugates of single-domain antibodies and quantum dots: toward a new generation of ultrasmall diagnostic nanoprobes." Nanomedicine: nanotechnology, biology and medicine 8.4 (2012): 516-525.
Suryadevara CM, et al. Are BiTEs the "missing link" in cancer therapy? Oncoimmunology. 2015;4:e1008339.
Svendsen, C. N. et al. A new method for the rapid and long term growth of human neural precursor cells. J Neurosci Methods 85, 141-152, doi:S0165-0270(98)00126-5 (1998).
Swanson, K. I. et al. Fluorescent cancer-selective alkylphosphocholine analogs for intraoperative glioma detection. Neurosurgery 76, 115-123, discussion 123-114, doi:10.1227/NEU.0000000000000622 (2015).
Takahashi, M, et al. "Identification of a novel type II classical cadherin: rat cadherin19 is expressed in the cranial ganglia and Schwann cell precursors during development." Developmental dynamics: an official publication of the American Association of Anatomists 232.1 (2005): 200-208.
Tillotson BJ, et al. Cells and cell lysates: a direct approach for engineering antibodies against membrane proteins using yeast surface display. Methods. 2013;60:27-37. doi: 10.1016/j.ymeth 2012. 03.010.
Valton, J. et al. "A Versatile Safeguard for Chimeric Antigen Receptor T-cell Immunotherapies" Nature Scientific Reports 8, Article No. 8972 (2018).
Van De Broek, B., et al. "Specific cell targeting with nanobody conjugated branched gold nanoparticles for photothermal therapy." ACS nano 5.6 (2011): 4319-4328.
Vanantwerp JJ, et al. Fine affinity discrimination by yeast surface display and flow cytometry. Biotechnology progress. 2000;16:31-37. doi: 10.1021/bp990133s.
Wang XX, et al. Mining a yeast library for brain endothelial cell-binding antibodies. Nature methods. 2007;4:143-145. doi: 10.1038/nmeth993.
Wang XX, et al. The use of scFv-displaying yeast in mammalian cell surface selections. Journal of immunological nethods. 2005;304:30-42. doi: 10.1016/j.jim.2005.05.006.
Weichert JP, et al. Alkylphosphocholine analogs for broad-spectrum cancer imaging and therapy. Science translational medicine. 2014;6:240ra275. doi: 10.1126/scitranslmed.3007646.
Wrensch, M., et al. "Epidemiology of primary brain tumors: current concepts and review of the literature." Neuro-oncology 4.4 (2002): 278-299.
Wu, C-Y, et al. "Remote control of therapeutic T cells through a small molecule-gated chimeric receptor." Science 350.6258 (2015).
Yang Y, et al. Targeting CD146 with a 64Cu-labeled antibody enables in vivo immunoPET imaging of high-grade gliomas. Proceedings of the National Academy of Sciences of the United States of America. 2015;112.E6525-6534. doi: 10.1073/pnas.1502648112.

(56) References Cited

OTHER PUBLICATIONS

Yang Y, et al. In vivo near-infrared fluorescence imaging of CD105 expression during tumor angiogenesis. European journal of nuclear medicine and molecular imaging. 2011;38:2066-2076. doi: 10.1007/s00259-011-1886-x.

Zhang RR, et al. Diapeutic cancer-targeting alkylphosphocholine analogs may advance management of brain malignancies. CNS Oncol. 2016;5:223-231. doi: 10.2217/cns-2016-0017.

Zhang, Q., et al. (2016). Co-stimulatory and co-inhibitory pathways in autoimmunity. Immunity, 44(5), 1034-1051.

Zhao, X, et al. "MicroRNA-mediated control of oligodendrocyte differentiation." Neuron 65.5 (2010). 612-626.

Zhu, X, et al. "Identification of internalizing human single-chain antibodies targeting brain tumor sphere cells." Molecular cancer therapeutics 9.7 (2010): 2131-2141.

Zorniak, M. et al. "Yeast display biopanning identifies human antibodies targeting glioblastoma stem-like cells." Scientific reports 7.1 (2017): 1-12.

Zorniak, M. et al. Differential expression of 2',3'-cyclic-nucleotide 3'-phosphodiesterase and neural lineage markers correlate with glioblastoma xenograft infiltration and patient survival. Clinical cancer research. 2012;18:3628-3636.

Zorniak, M. et al. Identification of Glioblastoma Cancer Stem-Like Cell-Binding Human Antibodies via Yeast Expression Library Biopanning. Poster at PEGS Conference 2013. Boston, MA.

Zorniak, M. et al. Identifying and Targeting Oligodendrocyte-Like Glioma Initiating Cells (GICs). Presentation at NTF Monday Night Seminar on Feb. 7, 2011.

Zorniak, M. et al. Membrane Proteomics of Human Glioblastoma Cancer Stem-Like Cells. NIH National Graduate Student Research Conference Poster. 2012.

* cited by examiner a b c a

| | Positive Screening Rounds Against 22 GSC | | | | | | | | |
|---|---|---|---|---|---|---|---|---|---|
| | 1 | 2 | 3 | 4 | 5 | 6 | 7 | 8 | 9 |
| Total no. yeast applied | 5×10⁶ | 2×10⁶ | 5×10⁷ | 5×10⁷ | 5×10⁷ | 5×10⁷ | 5×10⁷ | 5×10⁷ | 5×10⁷ |
| Yeast density (yeast/cm²) | 4×10⁷ | 4×10⁶ | 2×10⁶ | 2×10⁶ | 2×10⁶ | 2×10⁶ | 2×10⁶ | 2×10⁶ | 2×10⁶ |
| Surface area (cm²) | 126 | 50.2 | 25.1 | 25.1 | 25.1 | 25.1 | 25.1 | 25.1 | 25.1 |
| No. recovered yeast | ND | 2.58×10⁶ | 4.28×10⁵ | 9.05×10⁵ | ND | 2.58×10⁶ | 7.8×10⁶ | 5.86×10⁶ | 6.26×10⁶ |
| Recovery percentage | ND | 1.3 | 0.86 | 1.8 | ND | 5.2 | 16 | 12 | 13 |
| No. different binders/analyzed yeast | ND | ND | ND | ND | ND | 26/110 | ND | ND | 15/201 | b

| | Negative Screening Rounds Against Co-Culture | | | | |
|---|---|---|---|---|---|
| | S.6 | S.7 | S.8 | S.9 | |
| Total no. yeast applied | 5×10⁶ | 5×10⁶ | 5×10⁶ | 5×10⁶ | |
| Yeast density (yeast/cm²) | 2×10⁵ | 2×10⁵ | 2×10⁵ | 2×10⁵ | |
| Surface area (cm²) | 25.1 | 25.1 | 25.1 | 25.1 | |
| No. depleted yeast | 4.77×10⁶ | 4.62×10⁶ | 4.70×10⁶ | 4.66×10⁶ | |
| Depletion percentage | 95 | 93 | 94 | 93 | |
| No. different binders/analyzed yeast | 34/81 | 19/41 | 12/41 | 11/41 | | c

| | Re-Positive Screening Against 22 GSC |
|---|---|
| | RS.6 |
| Total no. yeast applied | 5×10⁷ |
| Yeast density (yeast/cm²) | 2×10⁶ |
| Surface area (cm²) | 25.1 |
| No. recovered yeast | 2.62×10⁷ |
| Recovery percentage | 52 |
| No. different binders/analyzed yeast | 27/83 |

FIGS. 6A-6E

Supplementary Table 1. Yeast scFv clone discovery counts.

| # | Clone ID | Round 6 | Round 9 | Round S.6 | Round S.7 | Round S.8 | Round S.9 | Round RS.6 | Total |
|---|---|---|---|---|---|---|---|---|---|
| 1 | 9.1 | 18 | 92 | 3 | 2 | 6 | 10 | 13 | 144 |
| 2 | 9.2 | 30 | 42 | 21 | 12 | 11 | 9 | 20 | 145 |
| 3 | 9.5 | 2 | 10 | 1 | 0 | 0 | 2 | 2 | 17 |
| 4 | 9.6 | 3 | 4 | 2 | 1 | 3 | 2 | 5 | 20 |
| 5 | 9.7 | 13 | 23 | 12 | 4 | 11 | 9 | 12 | 84 |
| 6 | 9.15 | 6 | 13 | 1 | 0 | 2 | 4 | 0 | 26 |
| 7 | 9.24 | 0 | 1 | 0 | 0 | 0 | 0 | 0 | 1 |
| 8 | 9.37 | 0 | 3 | 0 | 0 | 0 | 0 | 0 | 3 |
| 9 | 9.42 | 1 | 3 | 0 | 2 | 0 | 1 | 0 | 7 |
| 10 | 9.66 | 3 | 1 | 1 | 1 | 0 | 1 | 0 | 7 |
| 11 | 9.92 | 5 | 4 | 2 | 1 | 2 | 1 | 1 | 16 |
| 12 | 9.106 | 2 | 2 | 1 | 1 | 0 | 0 | 5 | 11 |
| 13 | 9.107 | 0 | 1 | 1 | 2 | 1 | 0 | 0 | 5 |
| 14 | 9.150 | 3 | 1 | 1 | 2 | 0 | 0 | 2 | 9 |
| 15 | 9.160 | 5 | 1 | 1 | 0 | 0 | 0 | 1 | 8 |
| 16 | 6.20 | 1 | 0 | 0 | 0 | 0 | 0 | 0 | 1 |
| 17 | 6.25 | 1 | 0 | 0 | 0 | 0 | 0 | 2 | 3 |
| 18 | 6.27 | 1 | 0 | 0 | 0 | 0 | 0 | 1 | 2 |
| 19 | 6.39 | 2 | 0 | 0 | 0 | 0 | 0 | 0 | 2 |
| 20 | 6.69 | 1 | 0 | 0 | 0 | 0 | 0 | 0 | 1 |
| 21 | 6.92 | 1 | 0 | 0 | 0 | 0 | 0 | 0 | 1 |
| 22 | S.6.1 | 1 | 0 | 3 | 0 | 0 | 0 | 0 | 4 |
| 23 | S.6.3 | 0 | 0 | 1 | 0 | 0 | 0 | 0 | 1 |
| 24 | S.6.4 | 1 | 0 | 3 | 0 | 0 | 0 | 1 | 5 |
| 25 | S.6.6 | 1 | 0 | 1 | 0 | 0 | 0 | 0 | 2 |
| 26 | S.6.7 | 0 | 0 | 2 | 0 | 0 | 0 | 0 | 2 |
| 27 | S.6.8 | 0 | 0 | 1 | 0 | 0 | 0 | 0 | 1 |
| 28 | S.6.20 | 0 | 0 | 1 | 0 | 0 | 0 | 0 | 1 |
| 29 | S.6.27 | 0 | 0 | 3 | 5 | 0 | 0 | 0 | 8 |
| 30 | S.6.28 | 0 | 0 | 2 | 0 | 0 | 0 | 0 | 2 |
| 31 | S.6.33 | 1 | 0 | 1 | 0 | 0 | 0 | 2 | 4 |
| 32 | S.6.47 | 0 | 0 | 1 | 0 | 0 | 0 | 1 | 2 |
| 33 | S.6.48 | 0 | 0 | 1 | 0 | 0 | 0 | 0 | 1 |
| 34 | S.6.49 | 0 | 0 | 2 | 0 | 0 | 0 | 0 | 2 |
| 35 | S.6.52 | 0 | 0 | 1 | 0 | 0 | 0 | 1 | 2 |
| 36 | S.6.58 | 0 | 0 | 1 | 0 | 0 | 0 | 0 | 1 |
| 37 | S.6.59 | 0 | 0 | 1 | 0 | 0 | 0 | 0 | 1 |
| 38 | S.6.65 | 0 | 0 | 1 | 0 | 0 | 0 | 0 | 1 |
| 39 | S.6.69 | 0 | 0 | 1 | 0 | 0 | 0 | 3 | 4 |
| 40 | S.6.76 | 0 | 0 | 1 | 0 | 0 | 0 | 0 | 1 |
| 41 | S.6.79 | 0 | 0 | 3 | 0 | 0 | 0 | 0 | 3 |
| 42 | S.7.19 | 0 | 0 | 2 | 1 | 0 | 0 | 0 | 3 |
| 43 | S.7.21 | 3 | 0 | 1 | 1 | 0 | 0 | 0 | 6 |
| 44 | S.7.25 | 0 | 0 | 0 | 1 | 0 | 0 | 0 | 1 |
| 45 | S.7.33 | 0 | 0 | 0 | 1 | 0 | 0 | 0 | 1 |
| 46 | S.7.37 | 0 | 0 | 0 | 1 | 0 | 0 | 0 | 1 |
| 47 | S.7.40 | 0 | 0 | 0 | 1 | 0 | 0 | 0 | 1 |
| 48 | S.8.4 | 0 | 0 | 0 | 0 | 1 | 0 | 1 | 2 |
| 49 | S.8.5 | 0 | 0 | 0 | 1 | 1 | 0 | 0 | 2 |
| 50 | S.8.24 | 2 | 0 | 0 | 1 | 1 | 1 | 0 | 5 |
| 51 | S.8.38 | 2 | 0 | 0 | 0 | 1 | 0 | 0 | 3 |
| 52 | S.9.8 | 1 | 0 | 0 | 0 | 0 | 1 | 0 | 2 |
| 53 | RS.6.5 | 0 | 0 | 0 | 0 | 0 | 0 | 1 | 1 |
| 54 | RS.6.35 | 0 | 0 | 0 | 0 | 0 | 0 | 1 | 1 |
| 55 | RS.6.61 | 0 | 0 | 0 | 0 | 0 | 0 | 1 | 1 |
| 56 | RS.6.63 | 0 | 0 | 0 | 0 | 0 | 0 | 1 | 1 |
| 57 | RS.6.76 | 0 | 0 | 0 | 0 | 0 | 0 | 1 | 1 |
| 58 | RS.6.77 | 0 | 0 | 0 | 0 | 0 | 0 | 1 | 1 |
| 59 | RS.6.85 | 0 | 0 | 0 | 0 | 0 | 0 | 1 | 1 |
| 60 | RS.6.94 | 0 | 0 | 0 | 0 | 0 | 0 | 1 | 1 |
| 61 | RS.6.101 | 0 | 0 | 0 | 0 | 0 | 0 | 1 | 1 |
| 62 | RS.6.102 | 0 | 0 | 0 | 0 | 0 | 0 | 1 | 1 |
| | Unique Clones | 26 | 15 | 34 | 19 | 12 | 11 | 27 | 62 |
| | Total Analyzed | 110 | 201 | 81 | 41 | 41 | 41 | 83 | 598 |

ANTIBODIES TARGETING GLIOBLASTOMA STEM-LIKE CELLS AND METHODS OF USE THEREOF

CROSS-REFERENCE TO RELATED APPLICATIONS

This application is a national stage filing under 35 U.S.C. 371 of International Patent Application No. PCT/US2018/054952, filed Oct. 9, 2018, which claims priority to U.S. Provisional Application No. 62/569,834 filed on Oct. 9, 2017, the contents of both of which are incorporated by reference in their entirety.

STATEMENT REGARDING FEDERALLY SPONSORED RESEARCH

This invention was made with government support under NS052649 awarded by the National Institutes of Health. The government has certain rights in the invention.

BACKGROUND OF THE INVENTION

The field of the invention is related to antibodies for use in identifying glioblastoma stem-like cells, methods of analyzing and categorizing GBM, and methods of treating GBM.

Glioblastoma multiforme (GBM), also known as Glioblastoma or grade IV astrocytoma, is an aggressive and deadly central nervous system malignancy that grows in the brain. The median survival of a GBM patient is 14.6 months after diagnosis, despite aggressive surgery followed by radiotherapy and temozolomide. Many studies have shown that GBM varies extensively in pathology and genotype features, which likely determine differential therapeutic response and patient outcomes. GBM is the most common brain tumor representing about 15% of brain tumors. The causes of GBM are still unclear. Typical diagnosis is made by a combination of CT scan, MRI scan and tissue biopsy. Typical treatment is surgery followed by radiation and/or chemotherapy. Despite aggressive treatment, the cancer usually recurs, with fewer than 3-5% people surviving longer than five years. GBM regrowth is believed to originate from therapeutically resistant cancer cells, including glioblastoma stem-like cell (GBM cells that biologically behave like stem cells).

There are very few molecular assays or clinical markers for classifying GBM that are clinically validated and prognostically useful. There is an unfilled need for new tools that can be used to identify clinically useful prognosis markers and help aid in the treatment of such tumors.

SUMMARY OF THE INVENTION

The present invention overcomes the aforementioned drawbacks by providing antibodies that specifically recognize glioblastoma stem-like cells.

In one aspect, the disclosure provides an isolated antibody able to bind glioblastoma stem-like cells, wherein the antibody comprises CDR1, CDR2 and CDR3 domains, wherein the domain CDR1 comprises SEQ ID NO:3 or a sequence with at least 85% identity to SEQ ID NO:3, the domain CDR2 comprises SEQ ID NO:4 or a sequence with at least 85% identity to SEQ ID NO:4, and the domain CDR3 comprising SEQ ID NO:5 or a sequence with at least 85% identity to SEQ ID NO:5.

In another aspect, the disclosure provides an antibody comprising the polypeptide sequence of SEQ ID NO: 1 or a sequence with at least 85% identity to SEQ ID NO:1. In another aspect, the disclosure provides the antibody of SEQ ID NO:2 or a sequence with at least 85% identity to SEQ ID NO:2.

In further aspects, isolated nucleic acid molecules encoding an antibody specific to glioblastoma stem-like cells are provided. In some aspects, the nucleic acid molecule is a recombinant expression vector. In another aspect, the disclosure provides host cells able to express antibodies specific to glioblastoma stem-like cells.

Another aspect provides a method of detecting glioblastoma stem-like cells in a sample, wherein the method comprises contacting the sample with an antibody capable of binding glioblastoma stem-like cells and detecting the binding of the antibody in the sample.

In yet another aspect, the method of detecting glioblastoma stem-like cells in a subject comprises (a) contacting a sample from a subject with the antibody capable of binding glioblastoma stem-like cells and (b) detecting binding of the antibody to the sample, wherein binding indicates glioblastoma stem-like cells within the subject.

Another aspect provides a method of identifying glioblastoma stem-like cells within a brain tumor, the method comprising: (a) contacting a sample from a brain tumor of a subject with an antibody capable of binding to glioblastoma stem-like cells; and (b) detecting the presence of glioblastoma stem-like cells, wherein the presence of the glioblastoma cells indicates the tumor is a glioblastoma.

In a further aspect, a method of treating a subject with glioblastoma is provided. The method comprises administering an antibody able to bind glioblastoma stem-like cells directly or indirectly linked with a therapeutic agent in an effective amount to treat the glioblastoma.

In another aspect, the disclosure provides a method of targeting an agent to glioblastoma stem-like cells, the method comprising directly or indirectly linking the agent with an antibody capable of binding to glioblastoma stem-like cells.

In yet another aspect, the disclosure provides a kit for carrying out the methods described herein.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

BRIEF DESCRIPTION OF THE DRAWINGS

FIG. 12. Supplemental Table 1 listing yeast scFv clones. Table listing the scFv clones and discovery counts during the rounds of enrichment.

DETAILED DESCRIPTION OF THE INVENTION

Figure 1A:
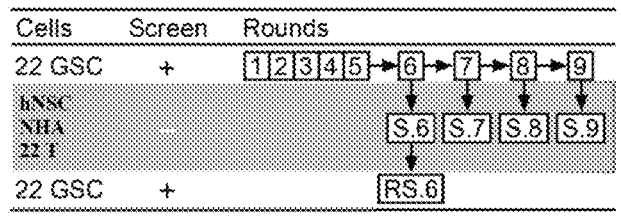
FIGS. 1A-1C. Biopanning enriches for GSC binding yeast antibodies. (a) Biopanning screening flow chart outlining strategy to achieve GSC-selective scFv. (b) A human nonimmune yeast display scFv library[18] was screened against 22 GSC for 9 rounds and visible yeast binding to 22 GSC was observed by light microscopy. Arrows show examples of widespread yeast binding. Binding efficiency after each round of screening was evaluated by yeast plating and colony counting. An increase in the number of recovered yeast in round 6 and maintenance after round 7 indicated enrichment and screen completion, respectively. Scale bar, 50 µm. (c) Negative screening on hNSC, NHA, and 22T co-culture to improve GSC-selectivity. After negative screening, photomicrographs show the depleted yeast binding after washing and recovery steps for round S.6 and S.9. Unbound yeast were recovered from each round, percentage shown. Positive re-screening on 22 GSC indicated further enrichment after depletion with 52% recovery. Scale bar, 100 µm.

The present disclosure provides antibodies that are specific to glioblastoma stem-like cells and uses thereof.

Before the present invention is described, it is understood that this invention is not limited to the particular methodology, protocols, and reagents described, as these may vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

Glioblastoma stem-like cells (GSC) are hypothesized to evade current therapies and cause tumor recurrence, contributing to poor patient survival of glioblastoma patients. Existing cell surface markers for GSC are developed from embryonic or neural stem cell systems; however, currently available GSC markers are suboptimal in sensitivity and specificity.

The present Examples demonstrate a selection method of a yeast display antibody library that revealed novel immunophenotypes specific for glioblastoma stem-like cells.

A single domain antibody VH-9.7 (SEQ ID NO:1) showed targeting for five distinct patient-derived GSC lines and visualized orthotopic GBM xenografts in vivo after conjugation with a near-infrared dye. This antibody is GSC specific, as it has markedly decreased binding for normal neural stem cell lines, and does not bind other tested differentiated astrocyte cell lines. These findings demonstrate a previously unexplored high-throughput strategy for GSC-selective antibody discovery, to aid in GSC isolation, diagnostic imaging, and therapeutic targeting.

Patients with glioblastoma (GBM) have experienced only modest improvements in survival (measured in months) after treatment with maximal surgery, radiation, temozolomide, chemotherapy and tumor-treating fields[1-2]. Growing evidence suggests that tumor recurrence due to therapeutically resistant glioblastoma stem-like cells (GSC) contributes to poor survival[3-5]. Unfortunately, current markers for detection, isolation and therapeutic targeting of GSC remain scarce[6-8] and somewhat controversial since many marker-negative tumor cells also exhibit GSC properties[9].

This disclosure provides an alternative approach to identify differentially binding single-chain variable fragments (scFv) and a single domain antibody (VH) via biopanning with a yeast display antibody library[14]. Optimized for cell surface screening, multivalent display of $10^4$-$10^5$ scFv on each yeast cell enhances avidity for isolation of both low affinity lead antibodies and antibodies that may recognize low abundance targets[17-19]. Moreover, the yeast display library employs a flocculin-deficient yeast strain that reduces non-specific binding to cell surfaces, thus facilitating high efficiency recovery of cell-binding scFv[17,18,20]. Biopanning with a yeast antibody library enriched for GSC-selective scFv.

A total of 62 unique scFv or VH clones were identified out of 598 candidates evaluated from multiple biopanning rounds. Each unique clone was evaluated for differential binding on 12 cell lines representing human brain, patient-matched GSC and GBM cell lines. One particular clone, VH-9.7 (SEQ ID NO:1), demonstrated GSC-targeting. Flow cytometry with VH-9.7 identified human GSC from invasive orthotopic tumor xenografts. Finally, intravenously injected fluorophore-conjugated VH-9.7 detected and localized to 22 focal GSC orthotopic xenografts.

Glioblastoma Stem-Like Cell Specific Antibodies

The present disclosure provides in one embodiment an isolated antibody or fragment thereof capable of selectively binding to glioblastoma stem-like cells. By "selectively" we mean an antibody capable of binding the surface of glioblastoma stem-like cells but has substantially reduced binding to other cell types, including neural stem cells or other cells of the brain. Term "binding" refers to the antibody's ability to detect the glioblastoma stem-like cells in a variety of environments in vitro and in vivo.

The disclosure provides an isolated recombinant antibody able to specifically bind glioblastoma stem-like cells, wherein the antibody comprises one or more domains selected from the group consisting of a CDR1 domain comprising SEQ ID NO:3 or a sequence with at least 85% identity to SEQ ID NO:3, a CDR2 domain comprising SEQ ID NO:4 or a sequence with at least 85% identity to SEQ ID NO:4, and a CDR3 domain comprising SEQ ID NO:5 or a sequence with at least 85% identity to SEQ ID NO:5. In another embodiment, the antibody comprises two or more domains selected from the group consisting of CDR1 domain comprising SEQ ID NO:3 or a sequence with at least 85% identity to SEQ ID NO:3, a CDR2 domain comprising SEQ ID NO:4 or a sequence with at least 85% identity to SEQ ID NO:4, and a CDR3 domain comprising SEQ ID NO:5 or a sequence with at least 85% identity to SEQ ID NO:5. In one embodiment, the antibody is a single domain antibody. Specifically, the antibody is the polypeptide sequence of SEQ ID NO:1 or an antibody with at least 85% identity to SEQ ID NO:1.

The disclosure provides an isolated recombinant antibody able to specifically bind glioblastoma stem-like cells, wherein the antibody comprises one or more domains selected from the group consisting of a CDR1 domain comprising SEQ ID NO:3 or a sequence with at least 95% identity to SEQ ID NO:3, a CDR2 domain comprising SEQ ID NO:4 or a sequence with at least 95% identity to SEQ ID NO:4, and a CDR3 domain comprising SEQ ID NO:5 or a sequence with at least 95% identity to SEQ ID NO:5. In another embodiment, the antibody comprises two or more domains selected from the group consisting of CDR1 domain comprising SEQ ID NO:3 or a sequence with at least 95% identity to SEQ ID NO:3, a CDR2 domain comprising SEQ ID NO:4 or a sequence with at least 95% identity to SEQ ID NO:4, and a CDR3 domain comprising SEQ ID NO:5 or a sequence with at least 95% identity to SEQ ID NO:5. In one embodiment, the antibody is a single domain antibody. Specifically, the antibody is the polypeptide sequence of SEQ ID NO:1 or an antibody with at least 95% identity to SEQ ID NO:1.

The disclosure further provides an isolated recombinant antibody able to specifically bind glioblastoma stem-like cells, wherein the antibody comprises one or more domains selected from the group consisting of a CDR1 domain comprising SEQ ID NO:3, a CDR2 domain comprising SEQ ID NO:4, and a CDR3 domain comprising SEQ ID NO:5. In another embodiment, the antibody comprises two or more domains selected from the group consisting of CDR1 domain comprising SEQ ID NO:3, a CDR2 domain comprising SEQ ID NO:4, and a CDR3 domain comprising SEQ ID NO:5.

Glioblastoma binding or targeting is mediated by regions within the VH-9.7 single chain antibody of SEQ ID NO:1, and may be mediated by one or a combination of multiple CDRs of the isolated antibody described herein. In some examples, the binding specificity to glioblastoma stem-like cells of the recombinant antibody or fragment can be provided by a single CDR, for example CDR3 domain. For example, the isolated recombinant antibody may comprise CDR1 of SEQ ID NO:3 or a sequence with at least 85% identity to SEQ ID NO:3. In another example, the isolated recombinant antibody may comprise CDR2 of SEQ ID NO:4 or a sequence with at least 85% identity to SEQ ID NO:4. In another example, the isolated recombinant antibody may comprise CD3 of SEQ ID NO: 5 or a sequence with at least 85% identity to SEQ ID NO:5. Suitable examples of the isolated antibody or fragment thereof may be made up of different combinations of CD1, CD2 and CD3 or sequences with at least 85% identity to CD1, CD2 and CD3, for example: (a) CDR1 comprising SEQ ID NO: 3 or a sequence with at least 85% identity to SEQ ID NO:3 and CDR3 comprising SEQ ID NO:5 or a sequence with at least 85% identity to SEQ ID NO:5, (b) CDR1 comprising SEQ ID NO:3 or a sequence with at least 85% identity to SEQ ID NO:3 and CDR2 comprising SEQ ID NO:4 or a sequence with at least 85% identity to SEQ ID NO:4, (c) CDR1, CDR2 and CDR3 comprising SEQ ID NO: 3 or a sequence with at least 85% identity to SEQ ID NO:3, SEQ ID NO:4 or a sequence with at least 85% identity to SEQ ID NO:4, and SEQ ID NO:5 or a sequence with at least 85% identity to SEQ ID NO:5 respectively, (d) CDR2 comprising SEQ ID NO:4 or a sequence with at least 85% identity to SEQ ID NO:4 and CDR3 comprising SEQ ID NO:5 or a sequence with at least 85% identity to SEQ ID NO:5, or combinations thereof. In another embodiment, the isolated recombinant antibody comprises CDR1, CDR2 and CDR3 domains, wherein the domain CDR1 comprises SEQ ID NO:3 or a sequence with at least 85% identity to SEQ ID NO:3, the domain CDR2 comprises SEQ ID NO:4 or a sequence with at least 85% identity to SEQ ID NO:4, and the domain CDR3 comprises SEQ ID NO:5 or a sequence with at least 85% identity to SEQ ID NO:5. In a preferred embodiment, the isolated antibody able to specifically bind glioblastoma stem-like cells comprises at least CDR3 domain comprising SEQ ID NO:5 or a sequence with at least 85% identity to SEQ ID NO:5. In one embodiment, the antibody is a single domain antibody. Specifically, the antibody is the polypeptide sequence of SEQ ID NO:1 or an antibody with at least 85% identity to SEQ ID NO:1. The sequence identity in any of the combinations denoted above may be 85%, 86%, 87%, 88%, 89%, 90%, 91%, 92%, 93%, 94%, 95%, 96%, 97%, 98%, %, or 99% for the above noted antibodies.

The terms "antibody" or "antibody molecule" are used herein interchangeably and refer to immunoglobulin molecules or other molecules which comprise an antigen binding domain. The term "antibody" or "antibody molecule" as used herein is thus intended to include whole antibodies (e.g., IgG, IgA, IgE, IgM, or IgD), monoclonal antibodies, polyclonal antibodies, and chimeric antibodies, humanized antibodies, and antibody fragments, including single chain variable fragments (ScFv), single domain antibody, and antigen-binding fragments, among others.

The term "antibody" also includes "antibody fragments" or "antibody-derived fragments" which comprise an antigen binding domain. The term "antibody fragment" as used herein is intended to include any appropriate antibody fragment that displays antigen binding function, for example, Fab, Fab', F(ab')2, scFv, Fv, dsFv, ds-scFv, Fd, dAbs, TandAbs dimers, mini bodies, monobodies, diabodies, and multimers thereof and bispecific antibody fragments. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art.

The scFv or one or more CDRs of the VH domain described herein may be used in chimeric antigen receptors (CAR) which can be expressed on one or more immune effector cells. In one embodiment, the disclosure provides an immune effector cell expressing CAR. Design and methods of CARs are known in the art and include, but are not limited to the first, second, third and fourth generation of CARs.

Genetically engineered CARs are contemplated herein. These genetically engineered receptors, CARs, comprise an antigen-specific recognition domain that binds to specific target antigen or cell and a transmembrane domain linking the extracellular domain to an intracellular signaling domain. Design and methods of making CAR are known in the art. In one embodiment, the antigen-specific recognition domain in the extracellular domain redirect cytotoxicity of the effector cell toward tumor cells.

The present invention provides chimeric antigen receptor (CAR) comprising an extracellular domain. The extracellular domain comprises a glioblastoma stem-like cell binding domain. In some embodiments, the extracellular domain comprises SEQ ID NO:1.

In another embodiment, the CAR comprises VH-9.7 (SEQ ID NO:1) linked to an intracellular domain where the intracellular domain comprises a cytoplasmic domain which comprises a signaling domain or domains (e.g. a zeta chain portion of T cell receptor) and optionally a costimulatory signaling region. Between the extracellular domain and the transmembrane domain of the CAR, or between the cytoplasmic domain and the transmembrane domain of the CAR, there may be incorporated a spacer region. As used herein, a spacer region generally refers to any oligo- or polypeptide that functions to link the transmembrane domain to either the extracellular domain or the cytoplasmic domain in the polypeptide chain. A spacer domain may comprise up to 300 amino acids, preferably about 10-100 amino acids, alternatively about 25-50 amino acids.

In some embodiments, the glioblastoma stem-like cell binding domain is a single-chain antibody variable fragment (scFv) fused to a transmembrane domain which is linked to a signaling domain. The signaling domain may be, in some embodiments, derived from CD3ζ or FcRy and optionally one or more co-stimulatory domains derived from a protein, such as, for example, but not limited to, CD28, CD137 (also known as 4-1BB), CD134 and CD278. Engagement of the CAR with its target antigen or cell results in the clustering of the CAR and delivers an activation stimulus to the CAR-containing effector cell. The main characteristic of the CARs is their ability to redirect immune effector cell specificity, thereby triggering proliferation, cytokine production, phagocytosis and production of molecules that can mediate cell death of the target cell in a major histocompatibility (MHC) independent manner, exploiting the cell specific targeting ability of antibodies.

In one embodiment, the CARs of the present invention comprise four functional domains: (1) a binding domain that binds the glioblastoma stem-like cells and thereby targets the CAR expressing immune effector cell to a glioblastoma stem-like target cells; (2) a spacer region that extends the binding domain away from the effector cell plasma membrane; (3) a transmembrane domain that anchors the CAR to the effector cell and links the binding domain to the intracellular signaling domain; and (4) an intracellular domain comprising a signaling domain or domains, and optionally one or more co-stimulatory signaling domains.

CAR-T cells designed to have switch-mediated activation are also contemplated. Specifically, a CAR-T cell with antibody-based switches to mediate the interaction between the CAR_T cells and target cell is contemplated. These CAR-T cells enable full control over both activity and specificity, as shown in Rodgers et al. ("Switch-mediated activation and retargeting of CAR-T cells for B-cell malignancies, PNAS, Jan. 12, 2006, pp. E459-E468, incorporated by reference in its entirety). Suitable scaffolds for such a switchable CAR-T (sCAR-T) are found in Rodgers et al. Briefly, antibody-based switches are engineered by the introduction of peptide neo-epitopes (PNE) at defined locations in an antigen-specific antibody. The sCAR-T cell binds the PNE and no endogenous tissue or antigen, and is therefor strictly dependent on the presence of the switch for activation. Suitable PNE peptide sequence includes, for example but not limited to, NYHLENEVARLKKL (SEQ ID NO:6). Suitable CAR can comprise scFv, CD8 hinge, CD137 and CD3ζ domains.

Other suitable ON-switch chimeric antigen receptors (CAR) are also contemplated in the present invention. For example, small molecule-gated CAR are contemplated, as described in Wu et al. ("Remote control of therapeutic T cells through a small molecule-gated chimeric receptor" Science 350(6258), Oct. 16, 2015, aab4077-9, incorporated by reference in its entirety).

Suitable CAR-T cells also include CubiCAR, a tri-functional CAR architecture that enables CAR-T cell detection, purification and on-demand depletion using CD20 minitopes and CD34 epitopes for T cell depletion and enrichment, respectively, as described in Valton et al. ("A Versatile Safeguard for Chimeric Antigen Receptor T-cell Immunotherapies" *Nature Scientific Reports* 8, Article number: 8972 (2018), the contents of which are incorporated by reference in its entirety.)

In another embodiment, the invention relates to a nucleic acid or nucleic acid construct encoding a CAR, the CAR comprising several polypeptide portions: (1) a binding domain that binds glioblastoma stem-like cells, or an antigen-binding fragment thereof (such as a scFv of SEQ ID NO:1); (2) a spacer region derived from CD8a, CD4, CD28 or CD7; (3) human CD3, CD28, CD8a or CD4 transmembrane region and (4) a human CD3ζ or FcR γ intracellular signaling domain, and (5) optionally one or more intracellular co-stimulatory signaling domains derived from a protein selected from the group consisting of CD28, CD137 (4-1BB), CD134 (OX40) and CD298 (ICOS). Suitable methods of making a CAR are described in, for example, US Appl. Publ. No. 2013/0287748, and PCT Appl. Publ. No. WO 2140099671, the contents of which are incorporated by reference in their entireties. The present invention also provides immune effector cells comprising CARs. In some embodiments, the present invention provides genetically modified immune effector cells comprising T lymphocytes, natural killer (NK) cells, natural killer T (NKT) cells, mature immune effector cells including neutrophils, macrophages which upon administration in a subject differentiate into mature immune effector cells; said immune effector cells expressing murine, human or humanized CARs that redirect these effector cells to specifically bind to and kill glioblastoma stem-like target cells. CAR-expressing immune effector cells are capable of killing target cells by immune effector cell mediated (e.g. T cell-mediated) cell death. In the case of T cell mediated killing, CAR-target binding initiates CAR signaling to the T cell, resulting in activation of a variety of T cell signaling pathways that induce the T cell to produce or release proteins capable of inducing target cell apoptosis by various mechanisms. These T cell mechanisms include, but are not limited to, for example, the transfer of intracellular cytotoxic granules from the T cell into the target cell, T cell secretion of pro-inflammatory cytokines that can induce target cell killing directly or indirectly via recruitment of other killer effector cells, and upregulation of death receptor ligands on the T cell surface that induce target cell apoptosis following binding to their cognate death receptor on the target cell.

In a preferred embodiment, the effector cell is a T cell, a NK cell or a NKT cell.

The antibodies or antibody fragments can be produced naturally or can be wholly or partially synthetically produced. Thus the antibody may be from any appropriate source, for example recombinant sources and/or produced in transgenic animals or transgenic plants. Thus, the antibody molecules can be produced in vitro or in vivo. Preferably the antibody or antibody fragment comprises at least the heavy chain variable region ($V_H$) which generally comprises the antigen binding site. The antibody or antibody fragment can comprise all or a portion of a heavy chain constant region, such as an IgG1, IgG2, IgG3, IgG4, IgA1, IgA2, IgE, IgM or IgD constant region.

Furthermore, the antibody or antibody fragment can comprise all or a portion of a kappa light chain constant region or a lambda light chain constant region. All or part of such constant regions may be produced naturally or may be wholly or partially synthetic. Appropriate sequences for such constant regions are well known and documented in the art.

The term "fragment" as used herein refers to fragments of biological relevance (functional fragment), e.g., fragments which can contribute to or enable antigen binding, e.g., form part or all of the antigen binding site or can contribute to the prevention of the antigen interacting with its natural ligands. Fragments in some embodiments comprise a heavy chain variable region ($V_H$ domain) of the invention. Fragments may also comprise one or more of the heavy chain complementarity determining regions (CDRs) of the antibodies or of the $V_H$ domains, or one or more of the non-specific light chain complementarity determining regions (CDRs), or $V_L$ domains to form the antigen binding site. Any suitable non-specific light chains may be used that do not interfere with the specificity of binding to the glioblastoma stem-like cells. In some embodiments, light chains may be added that enhance the ability of the antibody to bind to the glioblastoma stem-like cells. For example, a fragment is suitable for use in the present methods and kits if it retains its ability to bind to patient-derived glioblastoma stem-like cell lines.

The term "complementarity determining regions" or "CDRs," as used herein, refers to part of the variable chains in immunoglobulins (antibodies) and T cell receptors, generated by B-cells and T-cells respectively, where these molecules bind to their specific antigen. As the most variable parts of the molecules, CDRs are crucial to the diversity of antigen specificities generated by lymphocytes. There are three CDRs (CDR1, CDR2 and CDR3), arranged non-consecutively, on the amino acid sequence of a variable domain of an antigen receptor. Since the antigen receptors are typically composed of two variable domains (on two different polypeptide chains, heavy and light chain), there are six CDRs for each antigen receptor that can collectively come into contact with the antigen. A single whole antibody molecule has two antigen receptors and therefore contains twelve CDRs. Sixty CDRs can be found on a pentameric IgM molecule.

Within the variable domain, CDR1 and CDR2 may be found in the variable (V) region of a polypeptide chain, and CDR3 includes some of V, all of diversity (D, heavy chains only) and joining (J) regions. Since most sequence variation associated with immunoglobulins and T cell receptors is found in the CDRs, these regions are sometimes referred to as hypervariable regions. Among these, CDR3 shows the greatest variability as it is encoded by a recombination of VJ in the case of a light chain region and VDJ in the case of heavy chain regions. The tertiary structure of an antibody is important to analyze and design new antibodies.

The term "single-chain variable fragment" or "scFv," as used herein, refers to a fusion protein of the variable regions of the heavy ($V_H$) and light chains ($V_L$) of immunoglobulins, connected with a short linker peptide of ten to about 25 amino acids. The linker may usually be rich in glycine for flexibility, as well as serine or threonine for solubility, and can either connect the N-terminus of the $V_H$ with the C-terminus of the $V_L$, or vice versa. This protein may retain the specificity of the original immunoglobulin, despite removal of the constant regions and the introduction of the linker. scFvs may often be produced in microbial cell cultures such as E. coli or Saccharomyces cerevisiae.

ScFvs may be created to facilitate phage or yeast display, where it is highly convenient to express the antigen-binding domain as a single peptide. As an alternative, scFv can be created directly from subcloned heavy and light chains derived from a hybridoma. ScFvs have many uses, e.g., flow cytometry, immunohistochemistry, and as antigen-binding domains of artificial T cell receptors. In one embodiment, the present invention discloses scFvs. In one embodiment, scFvs can be designed and made that contain the three heavy chain variable domains, CDR1, CDR2, and CDR3, e.g., SEQ ID NO: 3, SEQ ID NO:4, and SEQ ID NO:5, respectively.

In one embodiment, the antibody or fragment comprises CDR1, CDR2 and CDR3 of SEQ ID NO: 3, SEQ ID NO:4, and SEQ ID NO.5. In some embodiments, additional polypeptide sequence is found linking the CDR1, CDR2 and CDR3 in order to allow for the formation of the proper three dimensional antigen binding site of the antibody or fragment so that the antibody or fragment is capable of binding to glioblastoma stem-like cells, specifically patient-derived glioblastoma stem-like cells.

In another embodiment, the antibody comprises the polypeptide of SEQ ID NO:1 or a sequence with at least 85% identity to SEQ ID NO:1.

In some embodiments, the antibodies have substantial identity to the polypeptide found in SEQ ID NO:1. In some embodiments, the antibodies have at least 85% identity to SEQ ID NO:1, alternatively at least 90% sequence identity, alternatively at least 92% sequence identity, alternatively at least 94% sequence identity, alternatively at least 95% sequence identity, alternatively at least 98% sequence identity, alternatively at least 100% sequence identity. In some embodiments, the modified protein has 100% sequence identity within CDR1, CDR2 and CDR3 within SEQ ID NO:1 (e.g. SEQ ID Nos. 3-5).

In some embodiments, the antibodies have substantial identity to the protein found in SEQ ID NO:2. In some embodiments, the antibodies have at least 85% identity to SEQ ID NO:2, alternatively at least 90% sequence identity, alternatively at least 92% sequence identity, alternatively at least 94% sequence identity, alternatively at least 95% sequence identity alternatively at least 98% sequence identity, alternatively 100% sequence identity. In some embodiments, the modified protein has 100% sequence identity within CDR1, CDR2 and CDR3 within SEQ ID NO:2 (e.g. SEQ ID Nos. 3-5).

Protein and nucleic acid sequence identities are evaluated using the Basic Local Alignment Search Tool ("BLAST") which is well known in the art (Karlin and Altschul, 1990, Proc. Natl. Acad. Sci. USA 87: 2267-2268; Altschul et al., 1997, Nucl. Acids Res. 25: 3389-3402). The BLAST programs identify homologous sequences by identifying similar segments, which are referred to herein as "high-scoring segment pairs," between a query amino or nucleic acid sequence and a test sequence which is preferably obtained from a protein or nucleic acid sequence database. Preferably, the statistical significance of a high-scoring segment pair is evaluated using the statistical significance formula (Karlin and Altschul, 1990), the disclosure of which is incorporated by reference in its entirety. The BLAST programs can be used with the default parameters or with modified parameters provided by the user.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 85% sequence identity to the SEQ ID. Alternatively, percent identity can be any integer from 85% to 100%. More preferred embodiments include at least: 85%, 86%, 87%, 88%, 89%, 90%, 91%, 92%, 93%, 94%, 95%, 96%, 97%, 98% or 99% compared to a reference sequence using the programs described herein; preferably BLAST using standard parameters, as described. These values can be appropriately adjusted to determine corresponding identity of proteins encoded by two nucleotide sequences by taking into account codon degeneracy, amino acid similarity, reading frame positioning and the like.

"Substantial identity" of amino acid sequences for purposes of this invention normally means polypeptide sequence identity of at least 85%. Preferred percent identity of polypeptides can be any integer from 85% to 100%. More preferred embodiments include at least 85%, 86%, 87%, 88%, 89%, 90%, 91%, 92%, 93%, 94%, 95%, 96%, 97%, 98%, %, or 99%.

The terms "monoclonal antibody" or "monoclonal antibody composition" as used herein refer to a preparation of antibody molecules of a single amino acid composition. The monoclonal antibody also includes "human monoclonal antibody" which refers to antibodies displaying a single binding specificity which have variable and constant regions derived from human germline immunoglobulin sequences. The human monoclonal antibodies can be produced by a hybridoma which includes a B cell obtained from a transgenic nonhuman animal, for example, a transgenic mouse, having a genome comprising a human heavy chain transgene and a light human chain transgene fused to an immortalized cell.

The term "chimeric antibody" refers to a monoclonal antibody comprising a variable region, i.e., binding region, from one source or species and at least a portion of a constant region derived from a different source or species, usually prepared by recombinant DNA techniques. Other forms of "chimeric antibodies" are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art.

The term "antibody" also shall include humanized antibody, human antibody and recombinant human antibody. The term "humanized antibody" refers to antibodies in which the human framework has been modified to comprise fragments of antibodies taken from a different species that provide specificity to an antigen.

The antibodies disclosed in the present invention are human antibodies, as they include the constant region from human germline immunoglobulin sequences. The term "recombinant human antibody" includes all human antibodies that are prepared, expressed, created or isolated by recombinant means, such as antibodies isolated from a host cell such as an SP2-0, NS0 or CHO cell (like CHO Kl) or from an animal (e.g., a mouse) that is transgenic for human immunoglobulin genes or antibodies expressed using a recombinant expression vector transfected into a host cell. Such recombinant human antibodies have variable and in some embodiments, constant regions derived from human germline immunoglobulin sequences in a rearranged form.

As used herein, the terms "proteins" and "polypeptides" are used interchangeably herein to designate a series of amino acid residues connected to each other by peptide bonds between the alpha-amino and carboxy groups of adjacent residues. The terms "protein" and "polypeptide" refer to a polymer of protein amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to an encoded gene product and fragments thereof. Thus, exemplary polypeptides or proteins include gene products, naturally occurring proteins, homologs, orthologs, paralogs, fragments and other equivalents, variants, fragments, and analogs of the foregoing.

In one embodiment, the antibody is selected from the group consisting of a single chain variable fragment (scFv) antibody, a single domain antibody, an antigen-binding fragment and a chimeric antibody.

In some embodiments, the isolated antibody or fragment thereof is directly or indirectly linked to a tag or agent. In some embodiments, the antibody or fragment thereof is conjugated to the tag or agent. In other embodiments, the tag or agent is a polypeptide, wherein the polypeptide is translated concurrently with the antibody polypeptide sequence.

The term "tag" or "agent" as used herein includes any useful moiety that allows for the purification, identification, detection, diagnosing, imaging, or therapeutic use of the antibody of the present invention. The terms tag or agent includes epitope tags, detection markers and/or imaging moieties, including, for example, enzymatic markers, fluorescence markers, radioactive markers, among others. Additionally, the term tag or agent includes therapeutic agents, small molecules, and drugs, among others. The term tag or agent also includes diagnostic agents.

In some embodiments, the antibody or fragment may contain a tag which is an antibody. In one embodiment, the tag may be an antibody against T-cell co-inhibitory domains. Suitable T-cell co-inhibitory domains include but are not limited to, for example, PD-1, CTLA4, BTLA, 4-1BB, among others (See, e.g., Zhang et al. Co-stimulatory and Co-inhibitory Pathways in Autoimmunity, Immunity, 44, May 17, 2016, pp. 1034-1051, incorporated by reference in its entirety). For example, the tag may be an antibody against PD-1, e.g. pembrolizumab (Keytruda™, Merck), nivolumab (Opdivo™, Bristol-Myers Squibb), among others. In another embodiment, the antibody or fragment may be linked to a T-cell co-stimulatory domain, for example, CD28, CD40L, ICOS, SLAMF6, among others (See, e.g., Zhang et al. incorporated by reference in its entirety).

The agent to be attached to an antibody described herein is selected according to the purpose of the intended application (i.e., killing, prevention of tumor cell proliferation). Such agents may include but are not limited to, for example, pharmaceutical agents, toxins, fragments of toxins, alkylating agents, enzymes, antibiotics, antimetabolites, antiproliferative agents, hormones, neurotransmitters, DNA, RNA, siRNA, oligonucleotides, antisense RNA, aptamers, diagnostics, radioopaque dyes, radioactive isotopes, fluorogenic compounds, magnetic labels, nanoparticles, marker compounds, lectins, compounds which alter cell membrane permeability, photochemical compounds, small molecules, liposomes, micelles, gene therapy vectors, viral vectors, and the like.

For use herein, the term "antibody conjugate" includes an antibody described above linked directly or indirectly to a tag or agent.

In one embodiment, the antibody or fragment (e.g. VH-9.7, SEQ ID NO:1) can be linked directly or indirectly to β-diketone, vinylketone, and β-lactam based linkers for functionalization of chemically programmable aldolase antibody and/or monoclonal antibody 38C2. (See, e.g., Gavrilyuk et al. β-Lactam-based Approach for Chemical Programming of Aldolast Antibody 38C2, *Bioorg Med Chem Lett.* 2009 Mar. 1; 19(5):1421-1424, incorporated by reference in its entirety.

Suitable epitope tags are known in the art and include, but are not limited to, 6-Histidine (His), hemagglutinin (HA), cMyc, GST, Flag (DYKDDDDK) tag, V5 tag, NE-tag, among others. Epitope tags are commonly used as a purification tag. A purification tag is a tag that allows isolation of the antibody from other non-specific proteins.

In one embodiment of the invention, the antibody of the invention is tagged with a detectable marker, preferably a fluorescent, enzymatic or a luminescent marker. Examples of suitable enzymes include, but are not limited to, horseradish peroxidase, alkaline phosphatase, beta-galactosidase, glucose-6-phosphatase, or acetylcholinesterase. Examples of suitable tags comprising prosthetic group complexes include, but are not limited to, streptavidin/biotin and avidin/biotin. Examples of suitable fluorescent materials include, but are not limited to, umbelliferone, fluorescein, fluorescein isothiocyanate, rhodamine, dichlorot[pi]azinylamine fluorescein, green fluorescent protein (GFP), red fluorescent protein (RFP), blue fluorescent dyes excited at wavelengths in the ultraviolet (UV) part of the spectrum (e.g. AMCA (7-amino-4-methylcoumarin-3-acetic acid); Alexa. Fluor 350), green fluorescent dyes excited by blue light (e.g. FITC, Cy2, Alexa Fluor 488), red fluorescent dyes excited by green light (e.g. rhodamines, Texas Red, Cy3, Alexa Fluor dyes 546, 564 and 594), or dyes excited with infrared light (e.g. Cy5) to be visualized with electronic detectors (CCD cameras, photomultipliers), dansyl chloride, phycoerythrin or the like.

Example of a luminescent material includes, but is not limited to, for example, luminol. Examples of bioluminescent materials include, but are not limited to, for example, luciferase, luciferin, and aequorin.

Suitable examples of radioactive material include, but are not limited to, $^{125}I$, $^{131}I$, $^{35}S$ or $^{3}H$. In some embodiments, the antibody is directly or indirectly linked to a radioisotope, an NMR or MRI contrast agent or nanoparticles for diagnosing, imaging and treatment. Suitable radioisotopes include, but are not limited to, $^{18}F$, $^{11}C$, $^{13}N$, $^{15}O$, $^{68}Ga$, $^{82}Rb$, $^{44}Sc$, $^{64}Cu$, $^{86}Y$, $^{89}Zr$, $^{124}I$, $^{152}Tb$ that can be used for PET imaging or $^{67}Ga$, $^{81m}Kr$, $^{99m}Tc$, $^{111}In$, $^{123}I$, $^{125}I$, $^{133}Xe$, $^{201}Tl$, $^{155}Tb$, $^{195m}Pt$ that can be used for SPECT scintigraphic studies, or $^{14}C$, $^{3}H$, $^{35}S$, $^{32}P$, $^{125}I$ that can be used for autoradiography or in situ hybridisation, or $^{211}At—$, $^{212}Bi—$, $^{75}Br—$, $^{76}Br—$, $^{131}I—$, $^{111}In$, $^{127}Lu—$, $^{212}Pb—$, $^{186}Re—$, $^{188}Re—$, $^{153}Sm—$, $^{90}Y$ that can be used to label the antibodies. Suitable NMR or MRI contrast agents are known in the art and include, but are not limited to, for example paramagnetic agents gadolinium (Gd), dysprosium (Dy) and manganese (Mn), and the superparamagnetic agents based on iron oxide (such as MION, SPIO or USPIO) or iron platinum (SIPP), and X-nuclei such as $^{18}F$, $^{13}C$, $^{23}Na$, $^{17}O$, $^{15}N$.

Suitable nanoparticles, including metal nanoparticles and other metal chelates, are known in the art and include, but are not limited to, for example, gold nanoparticles Van de Brock et al., ACS Nano, Vol. 5, No. 6, 4319-4328, 2011), quantum dots (A. Sukhanova et al., Nanomedicine, 8 (2012) 516-525), magnetic nanoparticles ($Fe_3O_4$), silver nanoparticles, nanoshells and nanocages.

Additionally, in some embodiments, liposomes, exosomes or co-block polymer nanoparticles are used for therapeutic delivery applications to GBM. Glioblastoma cell-targeting antibodies may be provided in combination with liposomes, nanoparticles or other analogous carriers loaded with a pharmaceutically active compound. Methods of preparing such compositions are known in the field (see, for example, Sugano et al., Antibody Targeting of Doxorubicin-loaded Liposomes Suppresses the Growth and Metastatic Spread of Established Human Lung Tumor Xenografts in Severe Combined Immunodeficient Mice, *Cancer Research* 60, 6942-6949, Dec. 15, 2000 and Martin et al., Nanomaterials in Analytical Chemistry, *Analytical Chemistry News & Features*, May 1, 1998; pp. 322 A-327 A). As used herein, the phrase "antibody in combination with a pharmaceutically active compound" shall not be limited by the method of manufacture and such compositions may be produced by, but not limited to, techniques of conjugating, linking, coupling and decorating known in the art.

One may wish to express the antibody as a fusion protein with a pharmacologically or therapeutically relevant peptide. For example, one may wish to express a scFv of the present invention with a protein linker and a protein therapeutic. Standard molecular biology techniques (e.g., restriction enzyme based subcloning, or homology based subcloning) could be used to place the DNA sequence encoding a protein therapeutic in frame with the targeting vector (usually a protein linker is also added to avoid steric hindrance). The fusion protein is then produced as one peptide in a host cell (e.g., yeast, bacteria, insect, or mammalian cell) and purified before use. Note the therapeutic does not need to be a whole protein. (For example, it can be a single peptide chain as a subunit in a protein with more than one peptide. The other peptides can be co-expressed with the vector fusion and allowed to associate in the host cell or after secretion).

Applicants envision that one may also include large particles as "therapeutic" compounds. For example, one may wish to decorate liposomes or nanoparticles with an embodiment of the targeting peptide or vector. Preferably, procedures to create vector-decorated liposomes may be taken from Jones, A. R. and E. V. Shusta, Blood-brain barrier transport of therapeutics via receptor-mediation. *Pharmaceutical Research*, 2007. 24(9): p. 1759-1771. Liposomes may be created using phospholipids, one of which is polyethylene glycol-distearoylphosphatidylethanolamine (PEG-DSPE) functionalized with maleimide as in the chemical linkage described above. The liposomes can be created such that they encapsulate a therapeutic in the lipid-based sphere. The vector may be modified using Traut's reagent and attached to the surface of the liposome as described in the chemical linkage methods. Note: Nanoparticles can be treated in the same way, except that the particles are solid-based (e.g., poly-butylcyanoacrylate) and must be artificially PEGylated before reaction with modified vectors.

In some embodiments of the present invention, antibodies or fragments may be administered with or without the above modifications. One may wish to administer the antibodies of the present invention without the modifications described above. For example, one may administer the antibodies through an intravenous injection or through intra-peritoneal and subcutaneous methods.

When the antibody is used with a diagnostic agent for detection, it may comprise a radioactive atom for scintigraphic studies, for example $^{99}Tc$ or $^{123}I$, or a spin label for nuclear magnetic resonance (NMR) imaging (also known as MRI), such as $^{13}C$, $^{9}F$, Fe, Gd, $^{123}I$, $^{111}In$, Mn, $^{15}N$ or $^{7}O$.

Further embodiments contemplated include antibody-drug conjugates. For example, suitable drugs (e.g. trastuzumab emtansine, brentuximab vendotin, among others) may be conjugated to the antibodies or fragments described herein with a cleavable or non-cleavable linker. Cleavable and non-cleavable linkers are known in the art.

Additionally, in some embodiments, non-naturally occurring amino acids are incorporated into the antibody, allowing for site-specific conjugation of the antibody to one or more agents. For example, in one embodiment, the use of selenocysteine allows for the site-specific conjugation of the antibodies of the present invention to suitable agents.

The antibodies of the present invention may also be used in bi-specific T-cell engager antibodies (BiTEs). The BiTEs contain a first binding site specific to CD3 for T-cell recruitment and activation and a second binding site for a targeted antigen (e.g. antigen on glioblastoma stem-like cells).

Further, the antibodies described herein can be used as bi-specific antibodies with blood-brain barrier or blood brain-tumor barrier or blood-CSF barrier penetrant properties. For example, suitable recombinant antibodies comprising a first binding specificity to glioblastoma stem-like cells and a second binding specificity to a blood-brain barrier (BBB) receptor which allows for BBV transcytosis properties. Suitable BBBR are discussed for example in WO2012/075037, WO/2014/033074 and WO2015101586, the contents of which are incorporated by reference in their entireties. Further, suitable blood-brain barrier targeting antibodies which can be genetically altered and combined with the glioblastoma stem-like specific antibodies of the present invention are discussed in US2008/0019984, US20150196663, PCT/US2007/070587, US20170174778, which are incorporated by reference in their entireties. In some embodiments, the blood brain barrier receptor is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), and heparin-binding epidermal growth factor-like growth factor (HB-EGF).

A further embodiment provides the use of the present antibodies for conjugating to magnetic beads. Such magnetic beads can be used for cell sorting from freshly resected GBM tumors or samples obtained from a patient.

In some embodiments, the tag is a single-step agent for detection and imaging. A single step agent is an agent that does not require a secondary step or agent to be detected or imaged. For example, the antibody may be directly or indirectly attached to the detection or imaging agent that can be assayed or visualized without the use of a secondary step or agent (e.g. secondary antibody).

In one embodiment the antibody contains a cMyc tag, a His tag, or a combination thereof. For example, a suitable antibody comprises SEQ ID NO:2 or a sequence with at least 85% identity to SEQ ID NO:2.

Conventional linking methods of linking a substance of interest to a polypeptide, in particular an antibody, are known in the art (e.g., See TERNYNCK and AVRAMEAS, 1987, "Techniques immunoenzymatiques" Ed. INSERM, Paris or G. T. Hermanson, Bioconjugate Techniques, 2010, Academic Press). Many chemical cross-linking methods are also known in the art. Cross-linking reagents may be homobifunctional (i.e., having two functional groups that undergo the same reaction) or heterobifunctional (i.e., having two different functional groups). Numerous cross-linking reagents are commercially available. Detailed instructions for their use are readily available from the commercial suppliers. A general reference on polypeptide cross-linking and conjugate preparation is: WONG, Chemistry of protein conjugation and cross-linking, CRC Press (1991).

In further embodiments, the agent is a therapeutic agent. As used herein, the term "therapeutic agent" refers to any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, chemotherapeutics, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, substances used for the treatment, prevention, diagnosis, cure or mitigation of a disease or illness; substances that affect the structure or function of the body, or pro-drugs, which become biologically active or more active after they have been placed in a physiological environment.

For example, the term "therapeutic agent" includes compounds or compositions for use in the treatment of cancers, e.g. chemotherapeutic agents, immunomodulatory agents, and the like.

Chemotherapeutic agents for use in treating glioblastoma are known in the art, and include, but are not limited to, for example, mitotic inhibitors, alkylating agents, antimetabolites, growth factor inhibitors, cell cycle inhibitors, enzymes, topoisomerase inhibitors, anti-survival agents, biological response modifiers, neoplastic agents, among others. Suitable chemotherapeutic agents include, but are not limited to, for example, temozolomide, carmustine, lomustine, cis-platinum (cisplatin), anti-angiogenic agent bevacizumab, gefitinib, erlotinib (tyrosine kinase inhibitors), dabrafenib and vemurafenib for patients with specific genomic alterations (i.e. BRAF V600E), among others. Minniti et al. (Chemotherapy for Glioblastoma: Current Treatment and Further Perspectives for Cytotoxic and Targeted Agents; Anticancer Research December 2009 vol. 29 no. 12 5171-5184), incorporated by reference in its entirety, provides chemotherapeutic agents that may be used in the practice of this invention.

Suitable immunomodulatory agents are the active agents of immunotherapy that are able to increase an immune response against the target tumor. Immunomodulatory agents include, for example, interleukins, cytokines, chemokines and immunomodulatory imide drugs (IMiDs) along with other compounds. Suitable immunomodulatory agents are known in the art and include, but are not limited to, IL-2, IL-7, IL-12, interferons (e.g., IFN-α, IFN-β, IFN-ε, IFN-κ and IFN-ω, IFN-γ, IFN-λ), G-CSF, CCL3, CCL26, CXCL7, TNFα, thalidomide and its analogues (lenalidomide, pomalidomide, and apremilast), cytosine phosphate-guanosine, oligodeoxynucleotides, glucans, immune checkpoint inhibitors (e.g., PD-1 inhibitor, PD-L1 inhibitor, CTLA-4 inhibitor, etc.), among others.

Further embodiments provide an isolated nucleic acid that encodes for the antibodies described above. Some embodiments provide an isolated polynucleotide encoding an antibody described herein. In one embodiment, the isolated polynucleotide encodes an antibody comprising the CDR1, CDR2 and CDR3 domain of SEQ ID NO:3 or a sequence with at least 85% identity to SEQ ID NO:3, SEQ ID NO:4 or a sequence with at least 85% identity to SEQ ID NO:4 and SEQ ID NO:5 or a sequence with at least 85% identity to SEQ ID NO:5, respectively. Suitably, the isolated polynucleotide may encode the antibody comprising the polypeptide sequence of SEQ ID NO:1 or a sequence with at least 85% identity to SEQ ID NO:1 or SEQ ID NO:2 or a sequence with at least 85% identity to SEQ ID NO:2.

A recombinant expression cassette comprising a polynucleotide encoding the antibody of the present invention is also contemplated. The polynucleotide may be under the control of a transcriptional promoter allowing the regulation of the transcription of said polynucleotide in a host cell.

The present invention also provides a recombinant expression cassette comprising a polynucleotide according to the present invention under the control of a transcriptional promoter allowing the regulation of the transcription of said polynucleotide in a host cell. Said polynucleotide can also be linked to appropriate control sequences allowing the regulation of its translation in a host cell.

The present invention also provides a recombinant vector (e.g., a recombinant expression vector) comprising a polynucleotide according to the present invention. Advantageously, said recombinant vector is a recombinant expression vector comprising an expression cassette according to the present invention.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The present invention also provides a host cell containing a recombinant expression cassette or a recombinant expression vector according to the present invention. The host cell is either a prokaryotic or eukaryotic host cell. The host cell is capable of expressing the antibodies of the present invention. Suitable host cells include, but are not limited to, mammalian cells and yeast cells. In some embodiments, the host cell may be a eukaryotic cell. The terms "host cell" refers to a cell into which exogenous nucleic acid has been introduced, including the progeny of such cells. Host cells include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

Compositions Comprising the Glioblastoma Stem-Like Cell Targeting Antibody

The present disclosure also provides compositions comprising an antibody specific for glioblastoma stem-like cells described above. In some embodiments, the composition is a pharmaceutical composition comprising the antibody specific for glioblastoma stem-like cells and a pharmaceutically acceptable carrier. Compositions are provided that include one or more of the disclosed antibodies that bind glioblastoma stem-like cells. Compositions comprising antibodies that are conjugated to and/or directly or indirectly linked to an agent are also provided. The compositions can be prepared in unit dosaged forms for administration to a subject. The amount and timing of administration are at the discretion of the treating clinician to achieve the desired outcome (e.g. imaging of glioblastoma stem-like cells or therapeutic treatment of glioblastoma). The antibody can be formulated for systemic or local (such as intra-tumor, intrathecal, intracranial) administration. In one example, the antibody is formulated for parenteral administration, such as intravenous administration.

As used herein, "pharmaceutical composition" means therapeutically effective amounts of the antibody together with a pharmaceutically-acceptable carrier. "Pharmaceutically acceptable" carriers are known in the art and include, but are not limited to, for example, suitable diluents, preservatives, solubilizers, emulsifiers, liposomes, nanoparticles and adjuvants. Pharmaceutically acceptable carriers are well known to those skilled in the art and include, but are not limited to, 0.01 to 0.1 M and preferably 0.05M phosphate buffer or 0.9% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include isotonic solutions, alcoholic/aqueous solutions, emulsions or suspensions, including saline and buffered media.

Pharmaceutical compositions of the present disclosure may include liquids or lyophilized or otherwise dried formulations and may include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc., or onto liposomes, microemulsions, micelles, milamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

In some embodiments, the compositions comprise a pharmaceutically acceptable carrier, for example, buffered saline, and the like. The compositions can be sterilized by conventional, well known sterilization techniques. The compositions may contain pharmaceutically acceptable additional substances as required to approximate physiological conditions such as a pH adjusting and buffering agent, toxicity adjusting agents, such as, sodium acetate, sodium chloride, potassium chloride, calcium chloride, sodium lactate, and the like.

In some embodiments, the antibodies are provided in lyophilized form and rehydrated with sterile water or saline solution before administration. In some embodiments, the antibodies are provided in sterile solution of known concentration. In some embodiments, the antibody composition may be added to an infusion bag containing 0.9% sodium chloride, USP and in some cases, administered in a dosage of from 0.5 to 15 mg/kg of body weight.

Uses of the Glioblastoma Stem-Like Cell Targeting Antibody

Methods of Detection, Imaging and Diagnosing

The antibodies disclosed herein can be used for methods of assaying, detecting, imaging, and diagnosing glioblastoma stem-like cells both in vitro and in vivo.

One embodiment provides a method of detecting glioblastoma stem-like cells in a sample, wherein the method comprises contacting the sample with an antibody described herein, and detecting the binding of the antibody in the sample. An increase in binding of the antibody to the sample as compared to binding of the antibody to a negative control sample detects glioblastoma stem-like cells within the sample.

The term "contacting" or "exposing," as used herein, refers to bringing a disclosed antibody and a cell, a target receptor, or other biological entity together in such a manner that the antibody can detect and/or affect the activity of the target, either directly; i.e., by interacting with the target itself, or indirectly; i.e., by interacting with another molecule, co-factor, factor, or protein that is attached to said target.

Another embodiment provides a method of confirming a diagnosis of glioblastoma in a subject by contacting a sample from the subject diagnosed with cancer with the antibody disclosed herein and detecting the binding of the antibody to the sample. In some embodiments, the sample from the subject is compared to a control sample. An increased binding of the antibody in the sample as compared to the control sample confirms the diagnosis of glioblastoma. A negative signal, e.g. no binding of the antibody, signals that glioblastoma is not present.

Another embodiment provides a method of isolating GSC using the antibody described herein. In one embodiment, the method of isolating GSC comprises contacting a sample with the antibody of the present invention and a secondary fluorescent antibody or a fluorescently labeled antibody of the present invention and subsequently isolating the GSC by fluorescence activated cell sorting (FACS). In another embodiment, magnetic beads may be conjugated to the antibody of the present invention. The conjugated beads may be contacted with a sample, and the GSC isolated by means of isolating the beads from the sample to obtain GSC (e.g. applying a magnetic force to the sample).

Further embodiments are contemplated wherein the antibody of the present invention is used for in vitro enrichment and study of patient specific GSCs.

In some embodiments, the control sample is a negative sample from a subject without cancer. In particular examples, the sample is a blood or tissue sample.

In some embodiments, a positive control sample is provided. A positive control sample may be a tissue sample from a subject with a confirmed case of glioblastoma. In another embodiment, the positive control is glioblastoma stem-like cells.

In some embodiments, the sample is an in vitro sample or an in vivo sample. Suitable samples are known in the art and include, but are not limited to blood samples, cerebral spinal fluid (CSF), body fluid samples, patient samples and GBM samples retrieved by biopsy or surgery.

Another embodiment provides a method of detecting glioblastoma stem-like cells in a subject comprising (a) contacting a sample from a subject with the antibody described herein, and (b) detecting binding of the antibody to the sample, wherein binding indicates glioblastoma stem-like cells within the subject. In some embodiments, the method of detecting glioblastoma stem-like cells in a subject is performed in vivo by administering the antibody to the subject and imaging the antibody. Methods of imaging the antibody are known in the art, and will depend on the imaging agent attached to the antibody as described above. Suitable methods of imaging the glioblastoma stem-like cells within the subject include, but are not limited to, PET scan, MRI scan, CT scan, among others.

In some embodiments, the antibody is directly conjugated with a detection or imaging agent.

Another embodiment provides a method of imaging glioblastoma stem-like cells in a subject comprising (a) administering to the subject an antibody described herein conjugated to an imaging agent, and (b) visualizing the localization of the antibody in the subject. Methods of visualizing the antibody are known in the art, and will depend on the imaging agent attached to the antibody as described above. Suitable methods of visualization of the glioblastoma stem-like cells within the subject include, but are not limited to, PET scan, MRI scan, CT scan, among others. In some embodiments, the visualization occurs in the brain of the subject.

Suitable methods of detection are known in the art and include, but are not limited to, for example, ELISA, Western blot, immunostaining, immunoprecipitation, flow cytometry, sensor chips, magnetic beads, and the like.

In some embodiments, the antibody is administered directly to brain of a subject, or via intrathecal injection, or intravenously to the subject.

Another embodiment of the present invention provides a method of detecting and labeling glioblastoma stem-like cells within a brain tumor. The method comprises administering to the subject an antibody specific to glioblastoma stem-like cells as described herein. In some instances, the method can be performed before surgery to aid the surgeon during surgery to remove the glioblastoma. In some embodiments the method can be performed during surgery in order to aid the surgeon to determine if more tissue should be removed. In such embodiments, the antibody may be conjugated to an imaging or fluorescent or other visualizable agent that can be used by the surgeon to detect presence of glioblastoma stem-like cells within the brain.

In another embodiment, the method of detecting and labeling glioblastoma stem-like cells is performed both before and after surgery in order to determine how much of the glioblastoma stem-like cells were removed during surgery. Images or quantitative or qualitative tests before and after surgery can be compared to determine the presence of glioblastoma stem-like cells removed.

A further embodiment provides methods and kits for identifying glioblastoma stem-like cells within a brain tumor and diagnosing glioblastoma, the method comprising: (a) contacting a sample from a brain tumor of a subject with the antibody described herein; and (b) detecting the presence of glioblastoma stem-like cells, wherein the presence of the glioblastoma cells indicates the tumor is a glioblastoma. In some embodiments, the method further comprises quantifying the amount of the glioblastoma stem-like cells within a brain tumor sample, wherein the presence of a greater amount of glioblastoma cells within the brain tumor indicates more invasive glioblastoma cancer as compared to a control sample.

Another embodiment provides methods and kits of assaying the presence of glioblastoma stem-like cells within a sample. The method comprises contacting the sample with the antibody specific to glioblastoma stem-like cells, and detecting the presence of binding. In some embodiments, the detecting is done by flow cytometry. In other embodiments, magnetic beads are used to isolate and quantify the cells that are able to bind to the antibody from within a sample. If other embodiments, methods of using ELISA are used to confirm the presence of glioblastoma stem-like cells within a sample.

Methods of Treatment

Further, the present disclosure provides methods and kits of preventing, treating or ameliorating glioblastoma is a subject in need thereof. The method comprises administering an effective amount of an antibody able to bind glioblastoma stem-like cells to treat or ameliorate at least one symptom of the glioblastoma. In a preferred embodiment, the antibody is directly or indirectly linked with a therapeutic agent or incorporated in a therapeutic cell. In further embodiments, the antibody is a bi-specific T cell engager or chimeric antigen receptor (CAR).

Glioblastoma, also known as glioblastoma multiforme (GBM) or grade IV astrocytoma, is a fast-growing, aggressive type of central nervous system tumor that forms on the supportive tissue of the brain. Glioblastoma is the most common grade IV astrocytoma. Glioblastomas may appear in any part of the brain, but it develops more commonly in the frontal and temporal lobes and mainly affects older adults. Many studies have shown that GBM varies extensively in pathology and genotype features. It is thought that these differences in pathology and genotype features likely determine differential therapeutic responses and patient outcomes. Current histopathologic classification of GBM is based on tumor architectural features, such as necrosis and/or endothelial proliferation rather than individual cell morphology. Glioblastoma encompasses a number of genetically distinct GBM subclasses with differential survival and response to treatment.

The term glioblastoma stem-like cell (GSC) is used interchangeably with GBM stem cell and encompasses stem-like populations that have tumor-initiating potential and contribute to therapeutic resistance among glioblastomas, and include a number of different subtypes. GSC cultures share similar genotypes, gene expression patterns, and in vivo biology of human glioblastomas, including the ability to form neurospheres and tumorigenic potential in vivo. GSCs can vary from patient to patient and molecular characterization has been ongoing. Zorniak et al. ("Differential Expression of 2'3'-Cyclic-Nucleotide 3'-Phosphodiesterase and Neural Lineage Markers Correlate with Glioblastoma Xenograft Infiltration and Patient Survival" Clinical Cancer Research, May 2012) describes GSC classification, which is incorporated by reference in its entirety. The antibodies of the present invention were able to bind and detect GSCs from multiple patient-derived GSC lines, thus providing a specific marker for GSCs or specific markers to determine the invasiveness potential of the GBM.

As used herein "subject" or "patient" refers to mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex. In one specific embodiment, a subject is a mammal, preferably a human.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, intradermal administration, intrathecal administration and subcutaneous administration. Administration can be continuous or intermittent. In various aspects, a preparation can be administered therapeutically; that is, administered to treat an existing disease or condition. In a preferred embodiment, the administration is intracerebral administration or intravenous administration.

For purposes of the present invention, "treating" or "treatment" describes the management and care of a subject for the purpose of combating the disease, condition, or disorder. Treating includes the administration of an antibody of present invention to prevent the onset of the symptoms or complications, alleviating the symptoms or complications, or eliminating the disease, condition, or disorder. Treating also encompasses therapeutic and palliative treatment. The terms "preventative," "preventing" and "prevention" refer to the ability to prophylactically stop the growth or onset of symptoms of glioblastoma.

The term "treating" can be characterized by one or more of the following: (a) the reducing, slowing or inhibiting the growth of glioblastoma, including reducing slowing or inhibiting the growth of glioblastoma stem-like cells; (b) preventing the further growth of glioblastoma tumors; (c) reducing or preventing the metastasis of glioblastoma cells within a patient, and (d) reducing or ameliorating at least one symptom of glioblastoma cancer. In some embodiments, the optimum effective amounts can be readily determined by one of ordinary skill in the art using routine experimentation.

In one embodiment, the term treating is characterized by a reduction in the number of glioblastoma stem-like cells in a subject.

In another embodiment, the treatment can result in cell-cycle inhibition of tumor cells (i.e. cytostasis). Cell cycle inhibition may be achieved by conjugating the antibody of the present invention to CDK4/6 inhibitors.

As used herein, the terms "effective amount" and "therapeutically effective amount" refer to the quantity of active therapeutic agent or agents sufficient to yield a desired therapeutic response without undue adverse side effects such as toxicity, irritation, or allergic response. The specific "effective amount" will, obviously, vary with such factors as the particular condition being treated, the physical condition of the subject, the type of animal being treated, the duration of the treatment, the nature of concurrent therapy (if any), and the specific formulations employed and the structure of the compounds or its derivatives.

In some embodiments, the antibody of the present invention is used for treatment in addition to standard treatment options, for example surgery and radiation therapy. In some embodiments, the antibodies of the present disclosure are used in combination therapy, e.g. therapy including one or more different anti-cancer agents.

In some embodiments, the antibodies specific to glioblastoma stem-like cells are used in methods to kill glioblastoma stem-like cells within a patient.

Kits

In some embodiments, kits for carrying out the methods described herein are provided. The kits provided may contain the necessary components with which to carry out one or more of the above-noted methods. In one embodiment, a kit for detecting glioblastoma stem-like cells is provided. The kit comprises an antibody descried herein and instructions for use. In some embodiments, the antibody is conjugated to a detection agent or magnetic beads. In further embodiments, a control is provided. In one embodiment, the control is a positive control, for example, glioblastoma stem-like cells. In another embodiment the control is a negative control, such as neural stem cells.

Another embodiment provides a kit for imaging glioblastoma stem-like cells within a subject. The kit provides an antibody conjugated to an imaging agent and instructions for administration. In some embodiments, the kit provides a pharmaceutically acceptable carrier.

A further embodiment provides a kit for treating glioblastoma, the kit comprising an antibody of the present invention directly or indirectly linked to a therapeutic agent or other immunological construct (e.g. CAR, etc.). Further, the kit may comprise a pharmaceutically acceptable carrier and instructions for use.

The present invention has been described in terms of one or more preferred embodiments, and it should be appreciated that many equivalents, alternatives, variations, and modifications, aside from those expressly stated, are possible and within the scope of the invention.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. For example, with regard to sequences "consisting of" refers to the sequence listed in the SEQ ID NO. and does refer to larger sequences that may contain the SEQ ID as a portion thereof.

The invention will be more fully understood upon consideration of the following non-limiting examples.

EXAMPLES

Example 1: Yeast Display Biopanning Identifies Human Antibodies Targeting Glioblastoma Stem-Like Cells Example 1 demonstrates the isolation and characterization of a single chain antibody that is specific to glioblastoma stem-like cells and with markedly reduced binding to neural stem cells and no binding to other brain cells. Thus, the current example demonstrates a highly specific tool for specifically being able to identify, label, and target glioblastoma stem-like cells associated with glioblastoma cancer.

This Example shows the isolation of an extensive collection of antibodies that were differentially selective for GSC. A single domain antibody VH-9.7 showed selectivity for five distinct patient-derived GSC lines and visualized orthotopic GBM xenografts in vivo after conjugation with a near-infrared dye. These findings demonstrate a previously unexplored high-throughput strategy for GSC-selective antibody discovery, to aid in GSC isolation, diagnostic imaging, and therapeutic targeting.

In this study, 6 rounds of biopanning enriched for GSC-binders, whereas subsequent positive and negative screens were used to further enhance GSC-selectivity and clonal diversity. Positive biopanning after round 6 increased the percent of recovered yeast to greater than 10%, demonstrating enrichment. Negative screens against human neural stem cells (hNSC), normal human astrocytes (NHA) and patient-matched serum-cultured GBM cells appeared to increase the observed frequency of different clones. A total of 62 unique scFv or VH clones were identified out of 598 candidates evaluated from multiple biopanning rounds in this non-saturating screen. Each unique clone was evaluated for differential binding on 12 cell lines representing human brain, patient-matched GSC and GBM cell lines. One particular clone, VH-9.7, demonstrated selectivity against all GSC lines. Flow cytometry with VH-9.7 identified human GSC from invasive orthotopic tumor xenografts. Finally, intravenously injected fluorophore-conjugated VH-9.7 detected and localized to focal GSC orthotopic xenografts. Our data successfully demonstrate a yeast biopanning approach for antibody discovery against primary human brain tumor lines, leading to identification of antibodies with potential use in research, diagnostic and therapeutic applications.

Figure 1B:
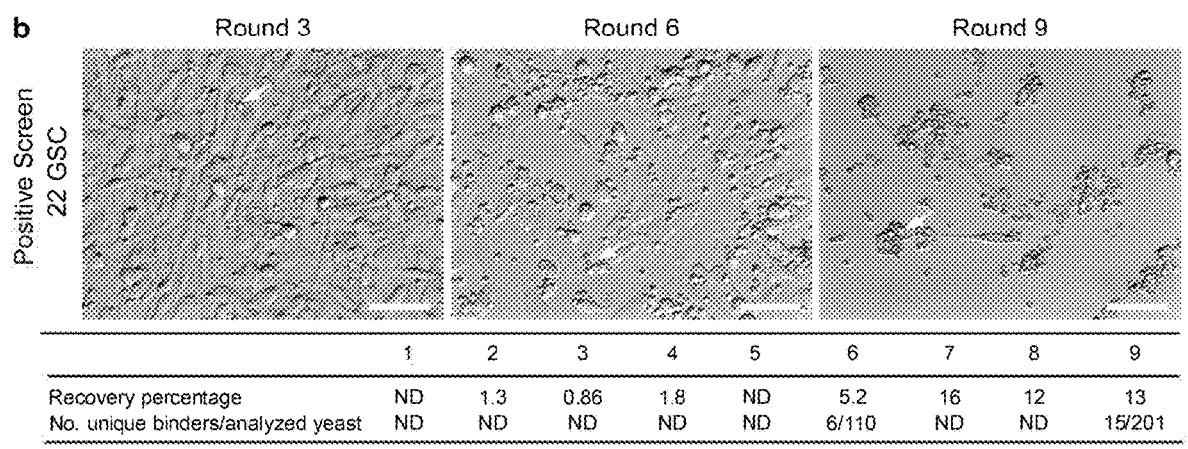
Figures 6A, 6B, 6C, 6D, 6E:
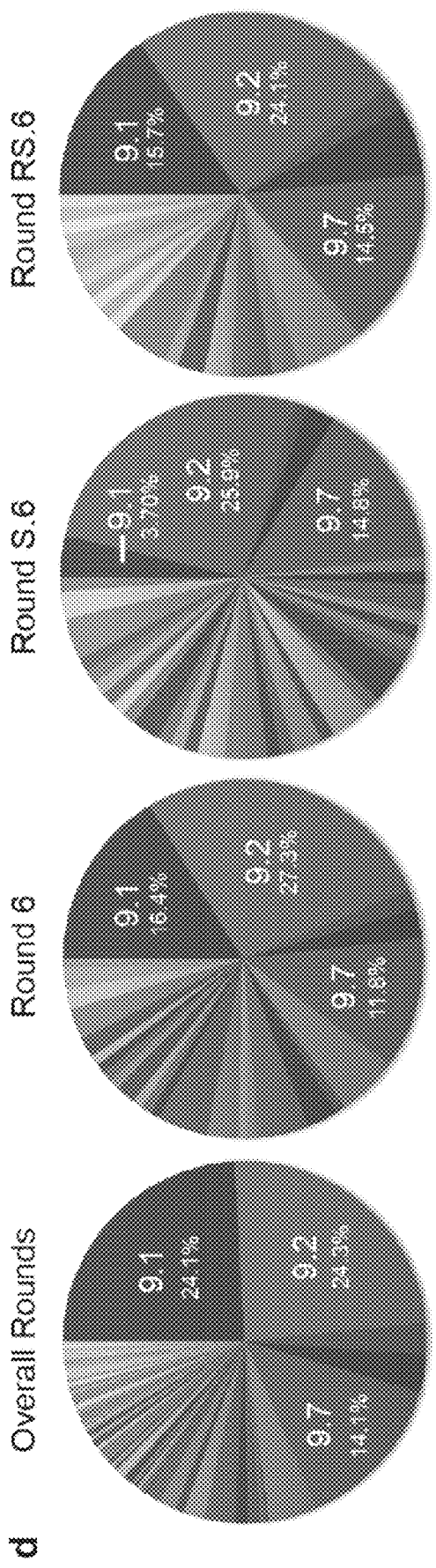
FIGS. 6A-6E. Descriptive statistics of biopanning screening. (a) Positive screening statistics against 22 GSC. (b) Negative screening statistics against hNSC, NHA, and 22T co-culture. (c) Re-positive screening statistics against 22 GSC. (d) Pie charts show increase in antibody clone diversity and selectivity after negative screening. scFv-9.1 is non-specific, and VH-9.7 is GSC-selective. Notably, by round 9 nearly half of the discovered clones are non-specific scFv-9.1. Negative screening rounds S.7, S.8, and S.9 show a steady rise in non-specific scFv-9.1 from 4.88% to 24.4%, but still less than 45.8% observed in round 9 alone. (e) Antibody-dependent enrichment was determined by incubating yeast binders from round nine with GSC in the presence or absence of antibody expression-inducing media (galactose) or non-inducing media (glucose). Scale bar, 100 µm.
Figures 6A, 6B, 6C, 6D, 6E:
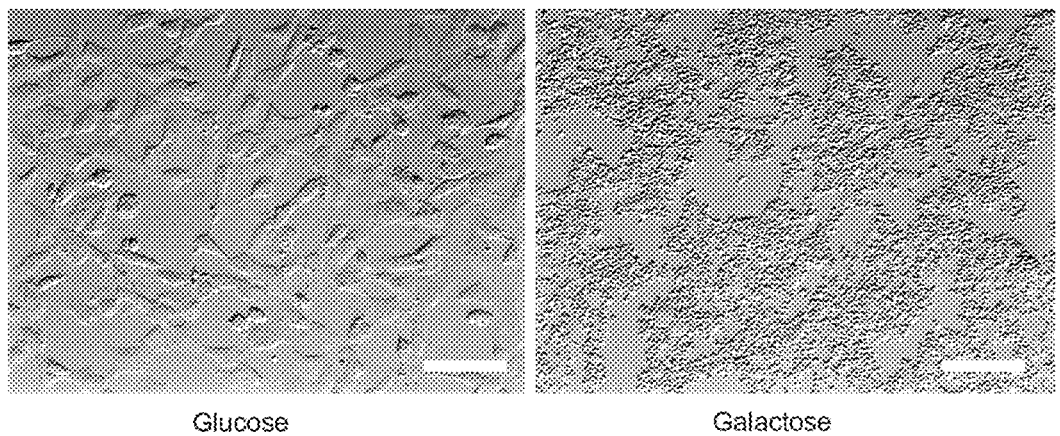

Yeast biopanning enriches for GSC-binding scFv and VH antibodies. The overall strategy for identification of GSC-binding scFv and VH involved enriching the yeast library against the patient-derived 22 GSC line followed by negative screening against hNSC, NHA and patient-matched serum-cultured 22 T cells (FIG. 1a). The patient-derived 22 GSC line was chosen for screening since it has been extensively characterized and generates reproducible mass-forming lesions after orthotopic implantation in the brains of non-obese diabetic severe combined immunodeficient (NOD-SCID) mice[5,21-26]. First, the yeast nonimmune human scFv library was panned against live patient-derived line 22 GSC for the identification of GSC-binders (FIG. 1b). Dissociated to single cells from spheres and seeded onto laminin overnight[27], 22 GSC were incubated with yeast displaying scFv. GSC-binders were recovered and amplified for subsequent rounds of screening (see Methods for details), as previously described[18]. Increased binding of yeast to the GSC cell surface was microscopically observed after round 6 of biopanning (FIG. 1b) and the recovery percentage of yeast cells applied to the cell monolayer remained stable from rounds 7-9, indicating both enrichment of GSC-binding scFv and completion of the screen (FIG. 1b; FIG. 6a). Yeast clones from round 9 demonstrated scFv-dependent binding to the GSC monolayer (FIG. 6e). Mining a total of 311 clones from the positive screen (round 6 and round 9 pools) led to the identification of 21 unique scFv and VH by BstNI restriction digest (FIG. 12 (Supplementary Table 1), Clone ID 1-21).

Figure 1C:
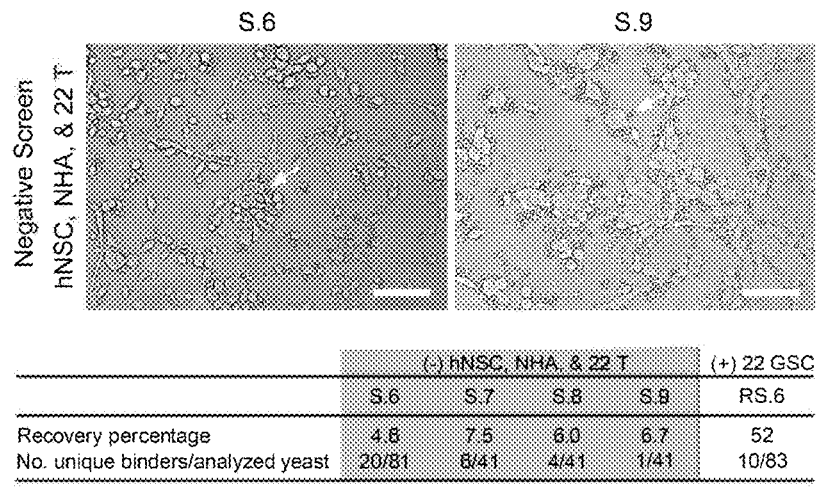

To further increase antibody diversity and remove false positives, negative or subtractive yeast biopanning screening strategies were used next. To this end, a mixed co-culture system with hNSC, NHA and patient-matched serum-cultured tumor line 22 T was used to deplete 22 GSC-enriched scFv-displaying yeast pools and increase the occurrence of GSC-selective binders (FIG. 1a). Negative screens were performed by starting with pools of initial GSC-binders from biopanning rounds 6-9, and greater than 90% of initial GSC-binders were removed via depletion with the hNSC/NHA/22T co-cultures, resulting in subtracted pools S.6-S.9 (FIG. 6b). Since pools S.6-S.9 may still contain non-GSC-binders, a repeat positive screen on 22 GSC was performed with the S.6 pool to yield pool RS.6, which showed a 52% recovery percentage indicating high enrichment for GSC-binders (FIG. 1c; FIG. 6c). BstNI restriction digest suggested that clone diversity was enhanced by the negative screen, since the highest number of different clones were observed in round S.6 at 34/81 (42%) (FIG. 1c; FIG. 6b, d; FIG. 12). S.6 also had 17 different clones that were not discovered in the non-saturated sampling of all unsubtracted rounds. Overall, 62 unique yeast scFv or VH clones were discovered and isolated out of a total 598 clones screened from all of the various positive and negative screening rounds (FIG. 12, Clone ID 1-62).

Figures 8A, 8B:
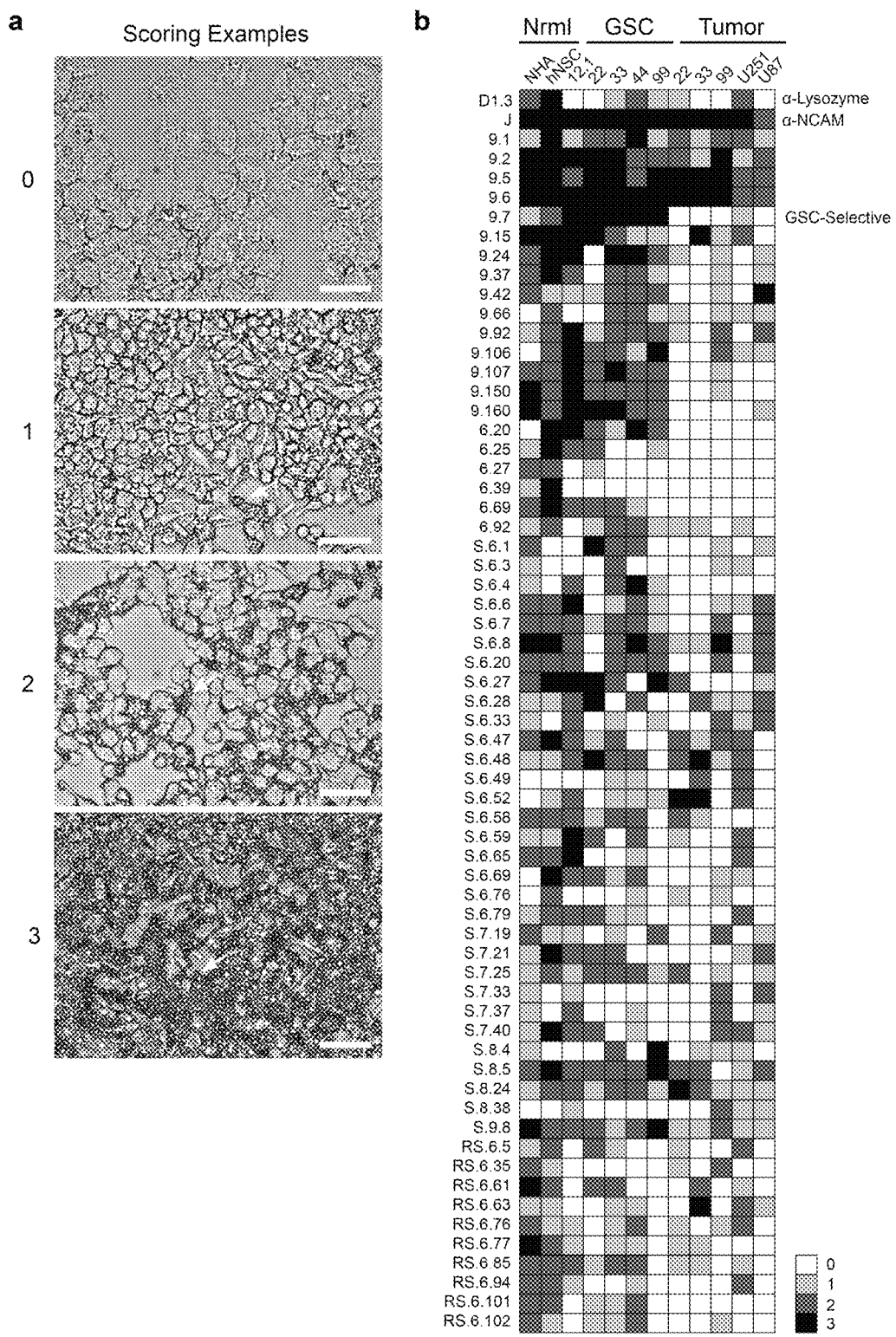
FIGS. 8A-8B. Unique yeast scFv and VH screened for GSC-selectivity. (a) Examples of qualitative scoring of yeast scFv binding with various intensity, from 0 (no observed binding) to 3 (significant yeast binding). Yeast were seeded in 96 well plates, incubated for 2 hours at 4° C. and washed according to the biopanning protocol. Scale bar, 50 µm. (b) Heat map of 62 yeast scFv or VH clones binding 12 different cell lines: normal human astrocytes (NHA); human neural stem cells (hNSC); 12.1, 22, 33, 44, & 99 GSC; and 22, 33, 99, U251, & U87 serum cultured tumor lines. Negative control: anti-lysozyme D1.3. Positive control: anti-neural cell adhesion molecule (NCAM) scFv-J.
Figures 9A, 9B, 9C:
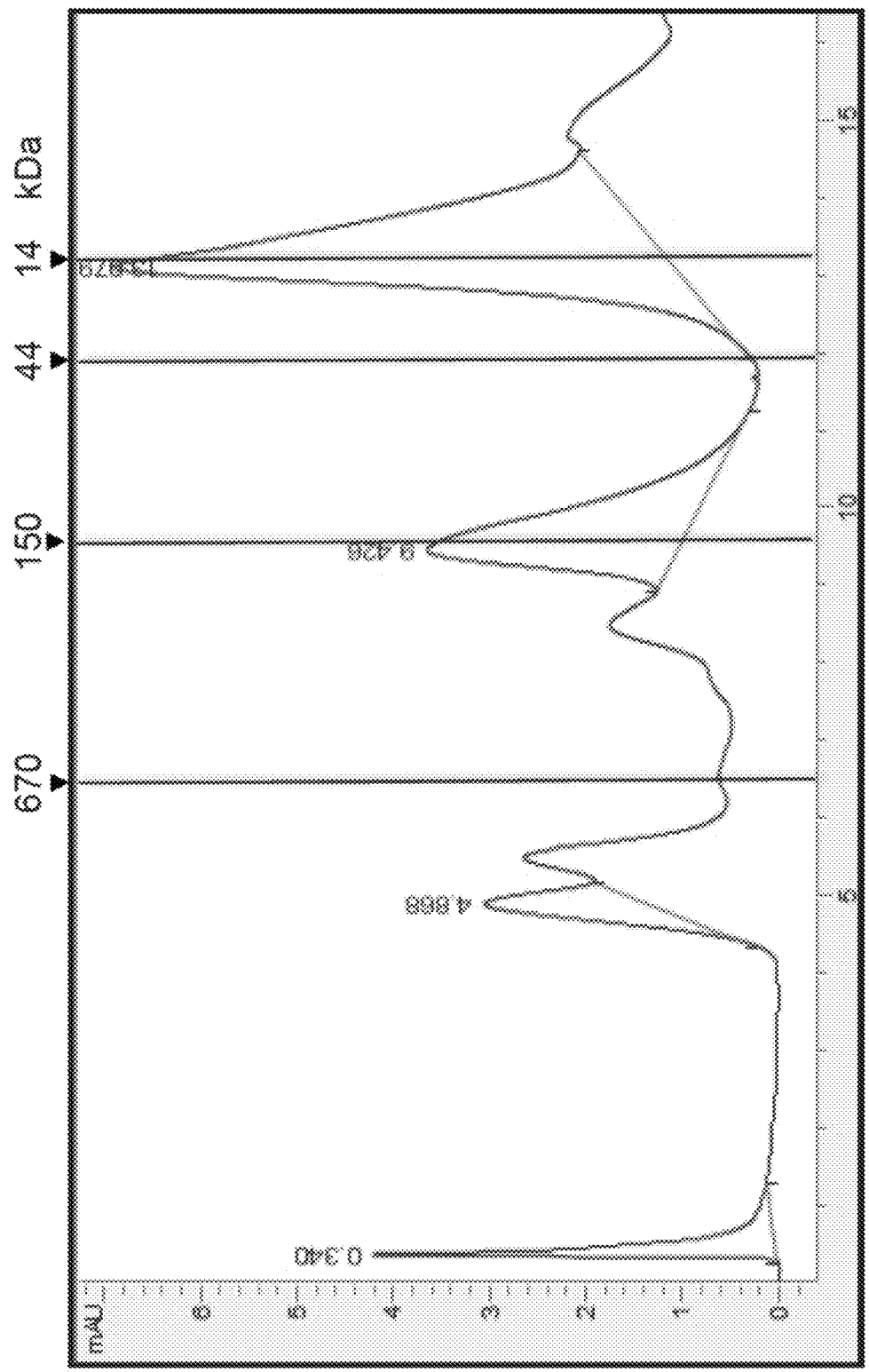
FIGS. 9A-9C. Monomeric affinity (Kd) of VH-9.7 on 33 GSCs. (a) VH-9.7 is produced largely as monomer. Ni-NTA purified VH-9.7 was analyzed by size exclusion chromatography. Elution fractions were collected and analyzed via western blotting for VH-9.7 against the c-Myc epitope tag. The major VH-9.7 peak (retention time=13.1 min) corresponded to a size of 15.3 kDa, and the expected monomeric size of VH-9.7 is ~15 kDa. Arrowheads represent the elution times for molecular size standards. 97% of the VH-9.7 detected by western blotting was monomeric. (b) Affinity titration of monomeric VH-9.7 on 33 GSCs. Monomeric VH-9.7 was titrated against 33 GSCs and binding assessed by flow cytometry. Fitting to a standard biomolecular binding equilibrium model, these data yielded a $K_d$ of 74.30±9.85 nM. The results of four independent titrations are plotted as mean±SEM. (c) Full-length immunoblot of FIG. 3a elution fractions for VH-9.7 and scFv-4-4-20. Dashed boxes indicate location of image cropping.
Figure 9A:
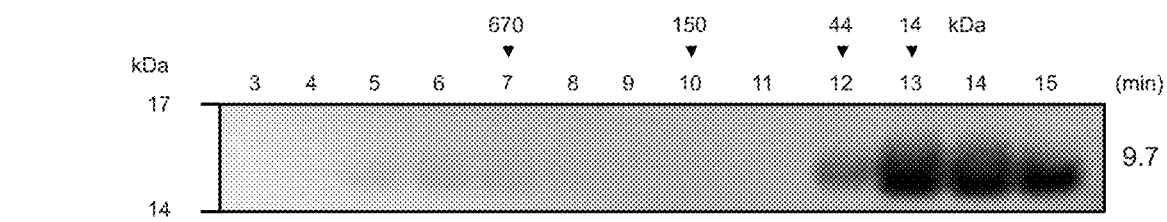
Figure 9B:
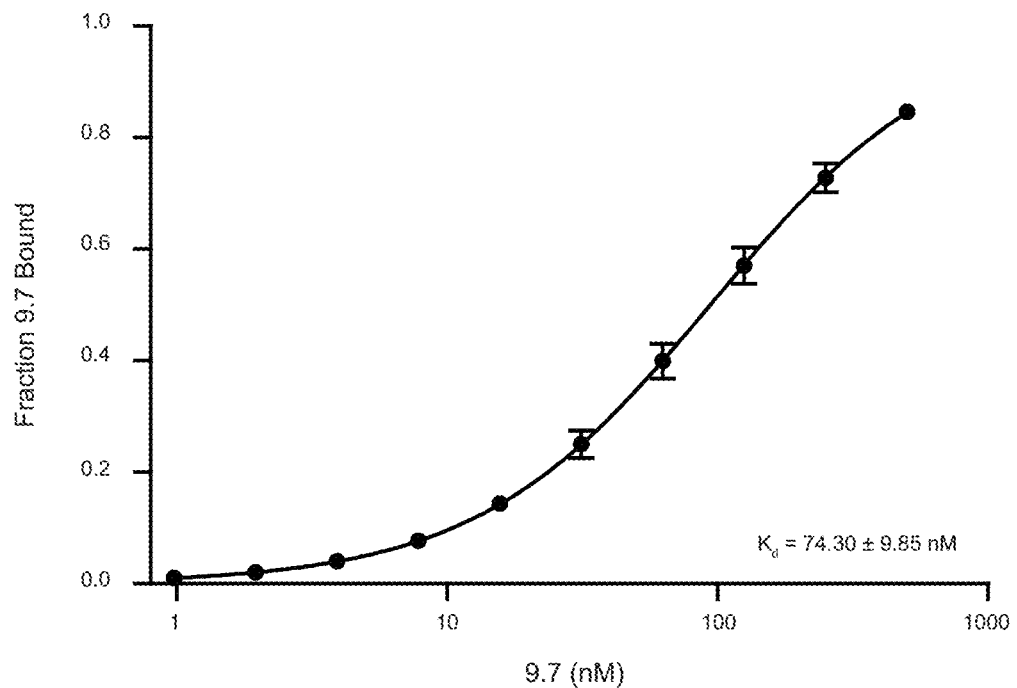
Figure 9C:
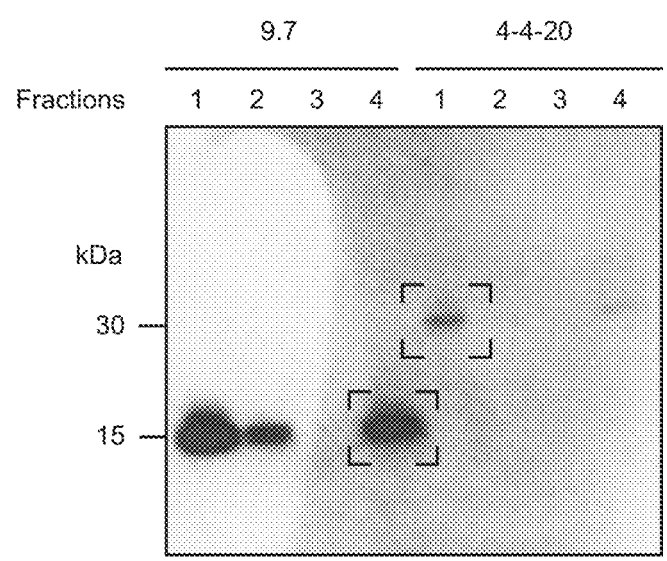

Evaluating cell-type binding capability of scFv and VH in yeast display format. To rapidly assess the cell-type binding profile of all 62 unique scFv/VH clones, each was evaluated by differential binding of the monoclonal yeast displayed scFv/VH to 12 distinct cell lines representing human brain, GSC and tumor cells with the goal of finding a GSC-selective antibody (FIG. 8b). Each of the 5 patient-derived GSC lines have been previously clustered into classes of varying invasiveness in NOD-SCID mice according to neural lineage markers[22]. Tumor xenografts generated from 12.1 and 22 GSC lines are focal, 33 GSC are minimally invasive, whereas those derived from 44 GSC and 99 GSC are highly infiltrative. Identically numbered, standard GBM or T lines were also derived from the same patient specimens by culturing in serum-containing media, rather than sphere-forming stem cell media. Binding capability of yeast clones was determined by qualitative scoring (i.e. 0-3) of cell-bound scFv-displaying yeast (FIG. 8a). Positive control scFv-J, anti-neural cell adhesion molecule (NCAM)[28] bound ubiquitously to every cell line since all are derived from neural tissue. Negative control D1.3 (anti-lysozyme)[29] maintained binding to various cell types during evaluation under manual washing conditions, suggesting presence of false positivity in this assay. Although we observed diverse scFv/VH binding from the 62 clones evaluated, yeast displayed VH-9.7 demonstrated high GSC-selectivity on 5 independent patient-derived lines and low tumor or normal brain binding (FIG. 2; FIG. 8b). Plasmid recovery, sequencing and analysis revealed that VH-9.7 is a single-domain antibody consisting of a heavy chain of VH1 germline origin (IGHV1-46*01, IGHD3-10*01, and IGHJ4*02), without an associated light chain fragment.

Figure 2:
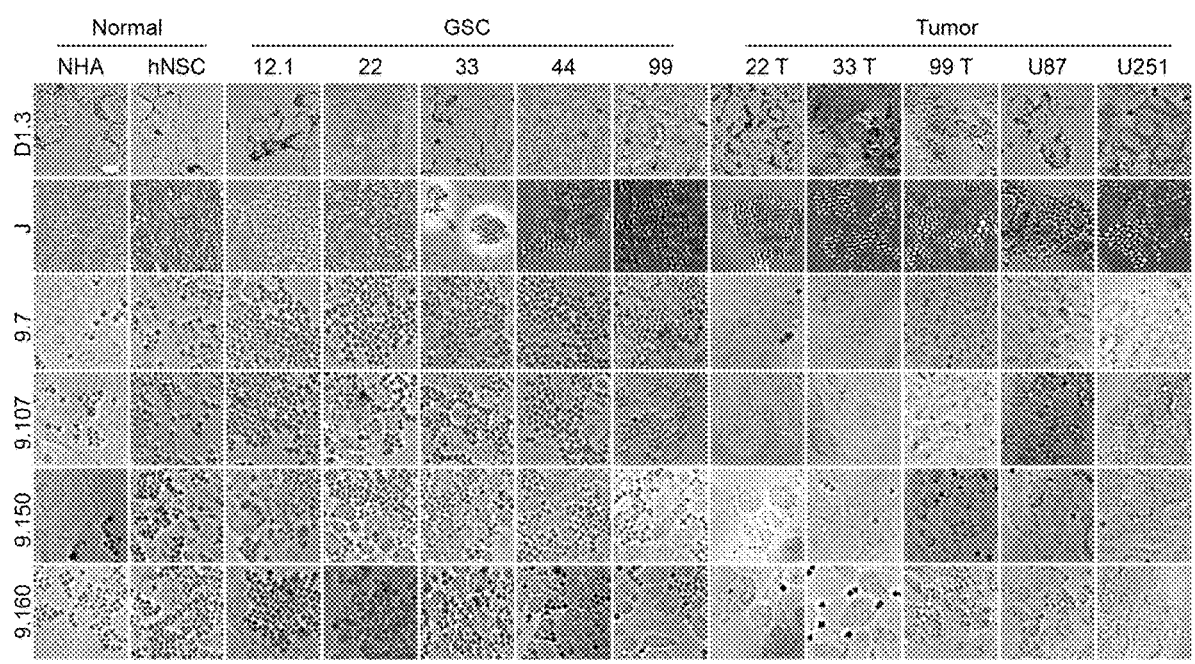
FIG. 2. Differential GSC binding of VH-9.7, scFv-9.107, -9.150, and -9.160. Twelve different cells lines used for qualitative binding assay: normal human astrocytes (NHA); human neural stem cells (hNSC); 12.1, 22, 33, 44, & 99 GSC; and 22, 33, 99, U251, & U87 serum cultured tumor lines. Negative control: anti-lysozyme D1.3. Positive control: anti-neural cell adhesion molecule (NCAM) scFv-J. Micrographs represent one trial of three technical replicates. Scale bar, 50 µm.

In addition to VH-9.7, we identified other antibodies with similar binding profiles: scFv-9.107, 9.150, and 9.160 were GSC-selective compared with the associated patient-matched tumor lines (FIG. 2; FIG. 8b). Also of future interest, clones isolated in subtracted pool S.6 collectively exhibited reduced binding to hNSC, NHA and tumor cell lines, while maintaining some GSC selectivity, albeit not to all 5 lines (FIG. 8b). For instance, scFv-S.6.3 binds selectively to 33 GSC, and scFv-S.6.4 binds to most GSC except for line 22 and 99 (FIG. 8b). In addition, from pool S.8, scFv-S.8.4 binds selectively to 33 and 99 GSC (FIG. 8b). Many of these new clones in the subtracted pools were not found in other rounds (FIG. 12). Taken together, the subtraction rounds expedited discovery of different scFv/VH clones (FIG. 12) that show heterogeneous binding across different GSC lines. To our knowledge, VH-9.7 is the only VH identified from the pools of binders in this study. The remaining clones are scFv format antibodies, some showing differential GSC binding. Since VH-9.7 exhibited binding specificity against all tested GSC lines, we pursued studies with this clone for additional in vitro and in vivo experiments.

Figures 3A, 3B, 3C:
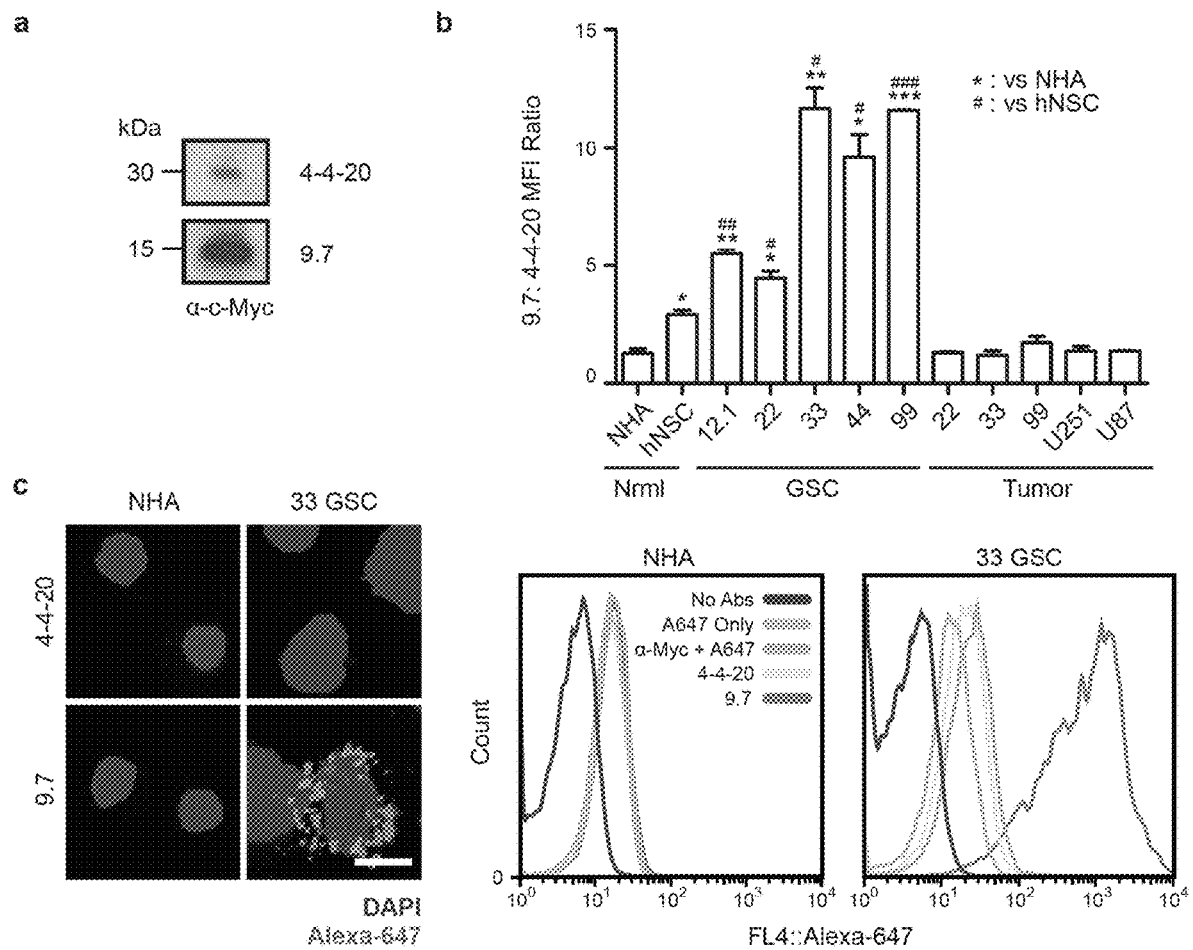
FIGS. 3A-3C. Soluble VH-9.7 is GSC-selective. (a) VH-9.7 was cloned into a pRS316-GAL yeast secretion vector and transformed into YVH10 yeast. Purified by Ni-NTA via a His6 tag and visualized by western blotting with anti-c-Myc. (b) Flow cytometry with VH-9.7 (125 nM), anti-c-Myc (66 nM), and Alexa-647. Mean fluorescence intensity (MFI) of VH-9.7 was normalized to signal generated from scFv-4-4-20. Histograms represent one experimental result. Two tailed unpaired t-tests used to confirm significance from two technical replicates (*/#p<0.05, /##p<0.01, */###p<0.001) versus NHA (*) and hNSC (#). Error bars indicate S.E.M. (c) Confocal microscopy performed after flow cytometry with live unfixed cells for internal consistency. Images were compiled as a z-stack projection to show cell surface labeling. Scale bar, 2.5 µm.

Purified VH-9.7 retains GSC-selectivity. VH-9.7 and the negative control, anti-fluorescein scFv-4-4-20, were secreted from yeast[30] and purified by Ni-NTA chromatography (FIG. 3a). VH-9.7 is produced predominantly in a monomeric form and has a GSC binding affinity of 74.30±9.85 nM (FIG. 9). GSC-selectivity of VH-9.7 was evaluated by flow cytometry, and binding was significantly higher ($p<0.05$) to all five GSC lines compared to normal and patient-matched, serum-cultured GBM tumor cell lines (FIG. 3b). As predicted by the qualitative yeast binding assay (FIG. 2), VH-9.7 binding to NHA was not observed, while hNSC labeling by VH-9.7 was detected at a significantly lower level than VH-9.7 binding of GSC (FIG. 3b). Confocal microscopy showed punctate VH-9.7 binding to an extracellular epitope on live unfixed 33 GSC (FIG. 3c).

Figures 4A, 4B:
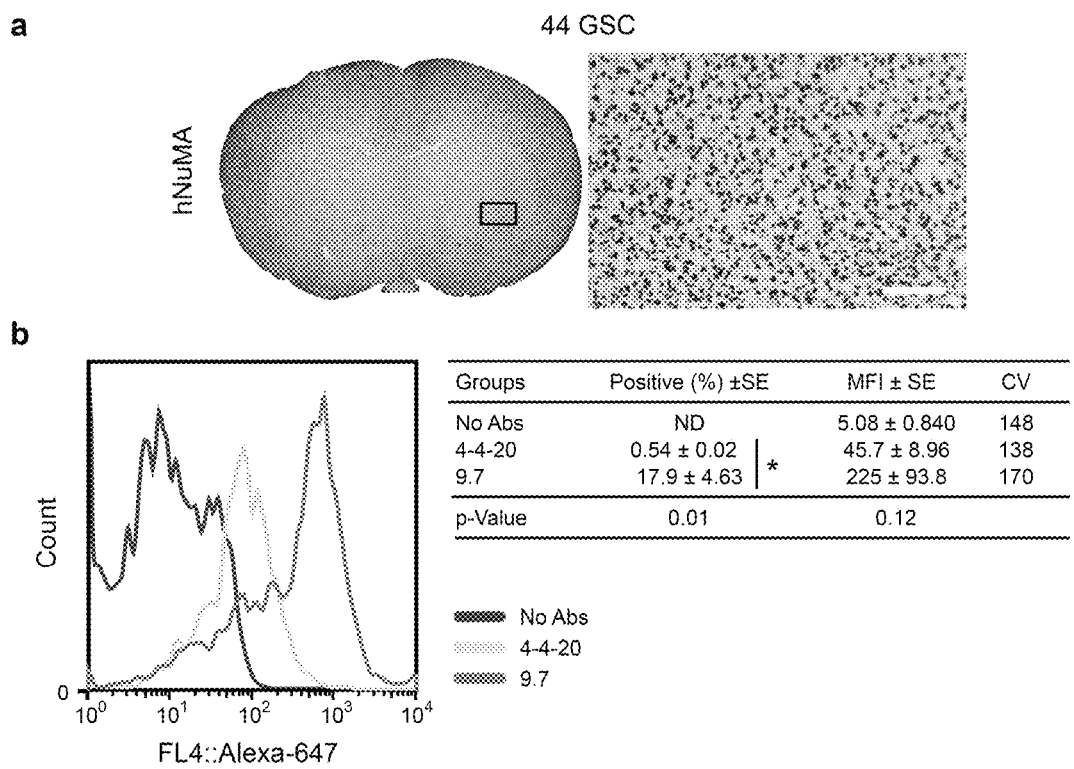
FIGS. 4A-4B. Purified VH-9.7 identifies human 44 GSC from orthotopic tumor xenografts. (a) Mouse brain coronal section shows whole-brain invasion of 44 GSC. Human nuclear mitotic apparatus protein (hNUMA) is specific to human cell nuclei (brown). Mouse nuclei counterstained with hemotoxylin (light blue). Black box indicates where the light micrograph was captured. Scale bar, 50 (b) VH-9.7 specifically detects human cells from mouse brain homogenates (n=6). No mean fluorescence intensity (MFI) signal difference was observed from normal mouse brain compared to negative control scFv-4-4-20 labeling. Histogram represents one trial of three technical replicates.
Figures 10A, 10B:
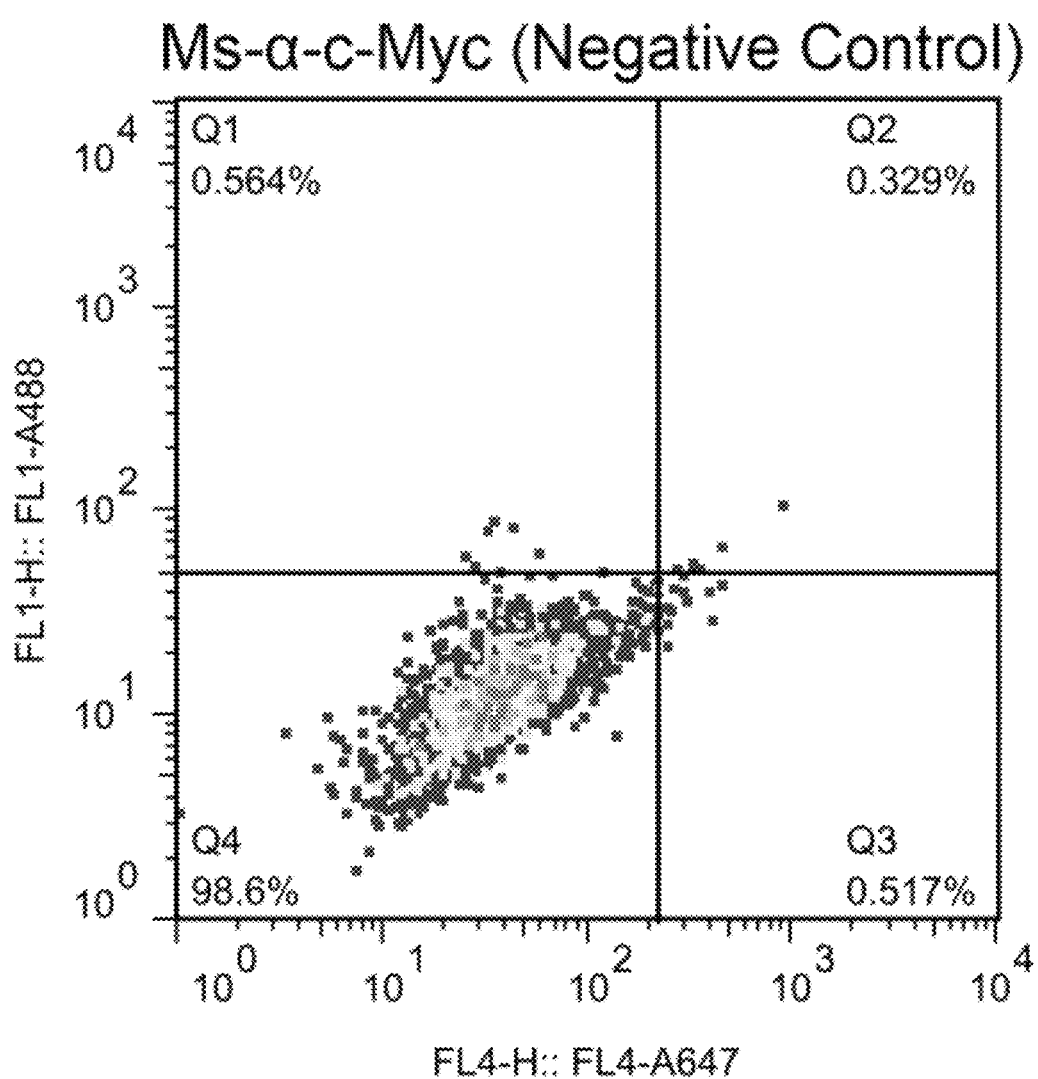
FIGS. 10A-10B. VH-9.7 labels human cells in formalin fixed orthotopic mouse 44 GSC-derived orthotopic tumor xenografts. (a) Dissociated brains from mouse xenografts were labeled with Ms-anti-c-Myc:AlexaFluor 647 (66 nM) and Gt-anti-Ms-IgG:AlexaFluor 488 (1:100) to serve as a negative control. (b) Addition of Ms-anti-human nuclei (HuNu) (1:100) and VH-9.7 (125 nM) to three 44 GSC-derived xenografts indicating human-specific labeling of VH-9.7 in quadrant 2 (Q2).
Figures 10A, 10B:
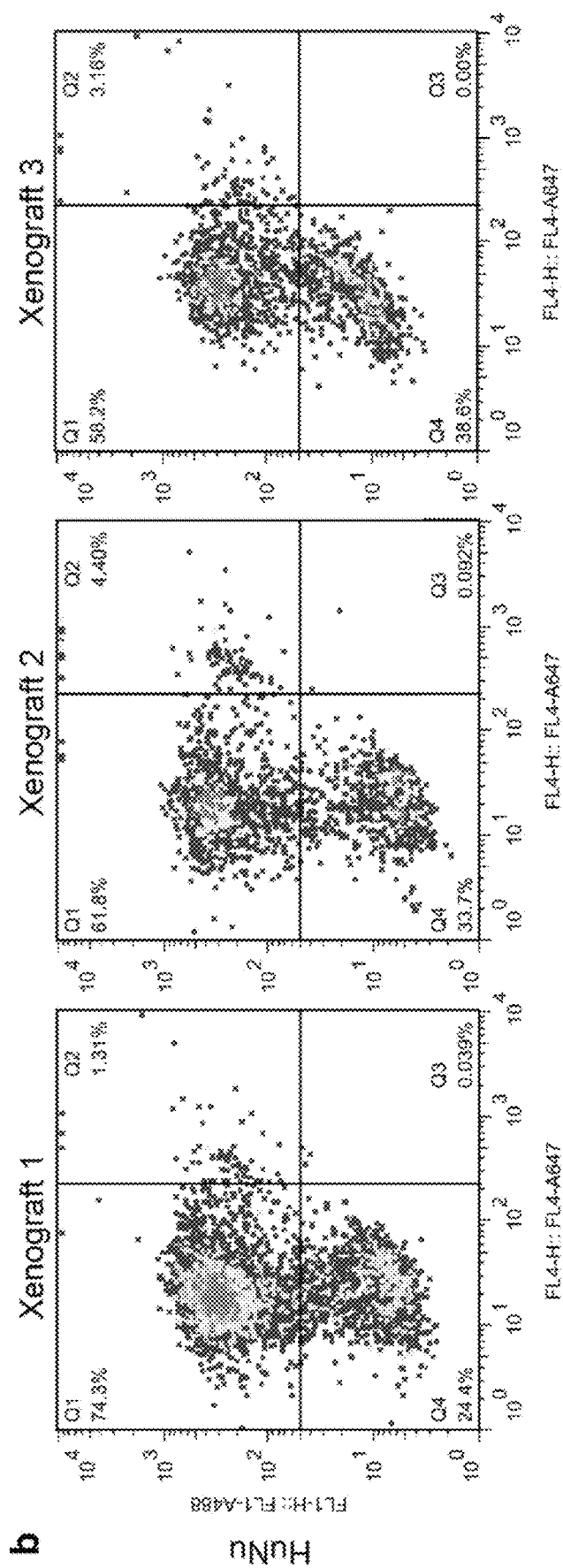

Purified VH-9.7 identifies human GSC in orthotopic mouse xenografts. Next, we used soluble VH-9.7 to identify 44 GSC harvested from NOD-SCID mouse brain xenografts via flow cytometry. Orthotopic 44 GSC invasive tumor xenografts infiltrated throughout the entire mouse brain, shown by the diffuse distribution of cells expressing human specific nuclear mitotic apparatus protein (hNuMA) (FIG. 4a). VH-9.7 positively identified a distinct population of cells from 44 GSC xenografts (17.9%±4.63), whereas negative control scFv-4-4-20 did not (0.54±0.02) ($p=0.01$) (FIG. 4b). In additional experiments, we co-labeled the tumor/normal brain cell ex vivo samples with both VH-9.7 and human specific nuclear antibody (HuNu). We only observed VH-9.7 labeling (1-4%, Q2) in the human (HuNu$^+$, Q1 and Q2) tumor cells, and not in normal mouse brain cells (HuNu$^-$, Q3 and Q4), supporting the GSC/tumor specificity of VH-9.7 (FIG. 10b). Additionally, the VH-9.7 antigen appeared sensitive to fixation, permeabilization, and other processing since decreased signal was observed in the co-labeling assay.

Figures 11A, 11B:
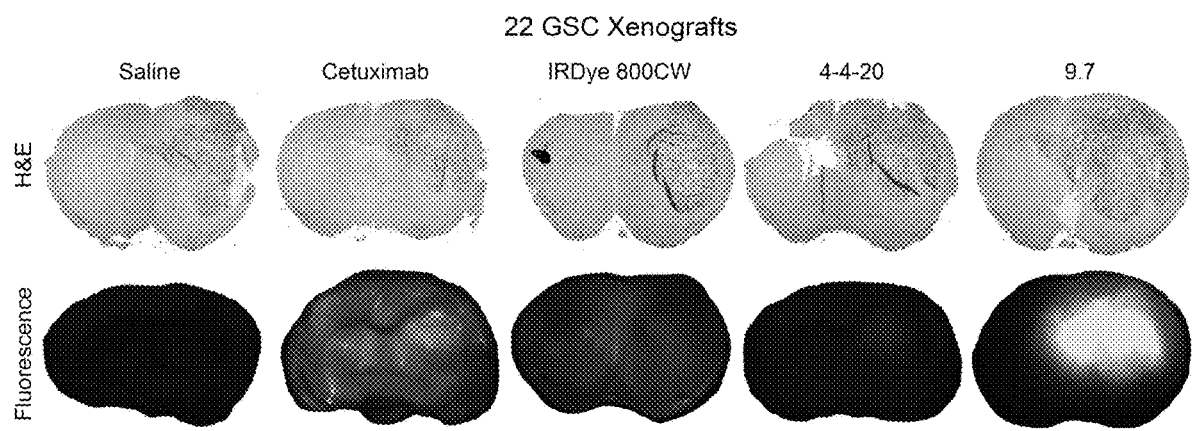
FIG. 11. Purified near-infrared VH-9.7 localizes to human 22 GSC orthotopic xenografts. Representative near-infrared fluorescent images captured from ex vivo coronal brain sections of orthotopic 22 GSC-derived tumors in mice. Tumor area was identified using H&E counterstaining. 22 GSC-derived xenografts have low expression of EGFR and the anti-EGFR antibody cetuximab was used as a control.

We chose to investigate localization of purified VH-9.7 to 22 GSC xenografts with in vivo infrared spectroscopy since these xenografts can be visualized with gadolinium-enhanced T1-weighted magnetic resonance imaging (data not shown). Thus, we hypothesized that the permeable tumor blood-brain barrier (BBB) of 22 GSC xenografts may permit VH entry. IgG (cetuximab), scFv-4-4-20, and VH-9.7 were mixed at a 1:1 molar ratio with IR800 dye to ensure an average of 1 fluorescent molecule for each IgG, scFv, or VH; 300 pmol of IRDye 800CW (IR800) dye with corresponding amount of IgG, scFv, and VH protein were injected intravenously into mice harboring orthotopic 22 GSC xenografts. Post-injection, an optimized time of 30 minutes was allowed to elapse for removal of unbound IR800 dye from normal tissues; additionally, transcardiac PBS perfusion further removed IR800 and unbound IgG/scFv/VH. The absence of free dye accumulation in tumor xenografts (FIG. 5; FIG. 11) demonstrates that tumor accumulation of VH-9.7, compared to the scFv-4-4-20 or IgG (cetuximab) controls, is not an artefactual size-dependent phenomenon but due to specific VH-9.7 binding to tumor antigen. After background correction, VH-9.7 tumor specificity was quantified and fluorescent signal was substantially higher (~10-fold) than control scFv-4-4-20 (FIG. 5; FIG. 11) ($p\leq0.05$; $n\geq2$ replicates with minimum of 2 independent animal experiments; VH-9.7=92.4±10.5 RFU and scFv-4-4-20=10.8±5.51 RFU; values are average±S.E.M.; RFU: relative fluorescent unit). Low tumor localization signal of the anti-EGFR antibody, cetuximab, is likely consistent with the previously reported low EGFR expression in 22 GSC xenografts[22] (FIG. 11).

Discussion

We have isolated 62 unique scFv or VH antibodies via biopanning a nonimmune yeast antibody library against patient-derived GSC, and they show differential binding against multiple human normal, tumor, and GSC lines. Negative screening strategies increased the diversity of a randomly sampled subset of antibodies retrieved after multiple rounds of positive selection, resulting in a higher likelihood of discovering GSC-binding clones. An identified human GSC-selective VH-9.7 antibody was validated for use as a research tool to identify and enrich for GSC from orthotopic tumor xenografts, and also as an in vivo immunodiagnostic tool to visualize tumor xenografts. Microscopically detectable yeast expressing human antibodies have practical utility in high-throughput discovery of cell type-selective scFv or VH clones.

Four recent studies have explored phage display screening approaches against GSC. Zhu et al.[11], used phage display flow cytometric sorting of CD133+ GBM spheres cells that were not fully validated for stem cell or tumor initiation properties. An internalizing scFv was identified, which showed some therapeutic effect when cloned into a full-length human IgG1 format and evaluated in a sphere forming assay. In Liu et al.[31], a phage display peptide library was used to identify new markers of glioblastoma initiating cells in vivo, but selective targeting was not investigated. Similarly, Beck et al.[12] reported using a 7-mer phage peptide library to identify a peptide that could be internalized and interact with nestin in GSC. When conjugated with a fluorescent quantum dot, this peptide localized specifically to orthotopic tumor xenografts. These studies demonstrate the promise of therapeutic and diagnostic protein-based modalities against GSC; however, selectivity to rigorously validated GSC lines with tumor initiation properties was not assessed. Another study using Cell-Systematic Evolution of Ligands by Exponential Enrichment (Cell-SELEX) or nucleic-acid based aptamers identified GSC-selective agents[13], however, labeling of human neural stem cells and localization to orthotopic xenografts were not evaluated. Our study isolated yeast biopanning-identified human antibodies screened against multiple GSC lines (each rigorously validated for stem/progenitor marker expression, multipotent differentiation and tumor initiation properties) that demonstrate both GSC-selectivity and localization to orthotopic tumor xenografts, potentially expanding the repertoire of GSC targeting biologics.

Figures 5A, 5B:
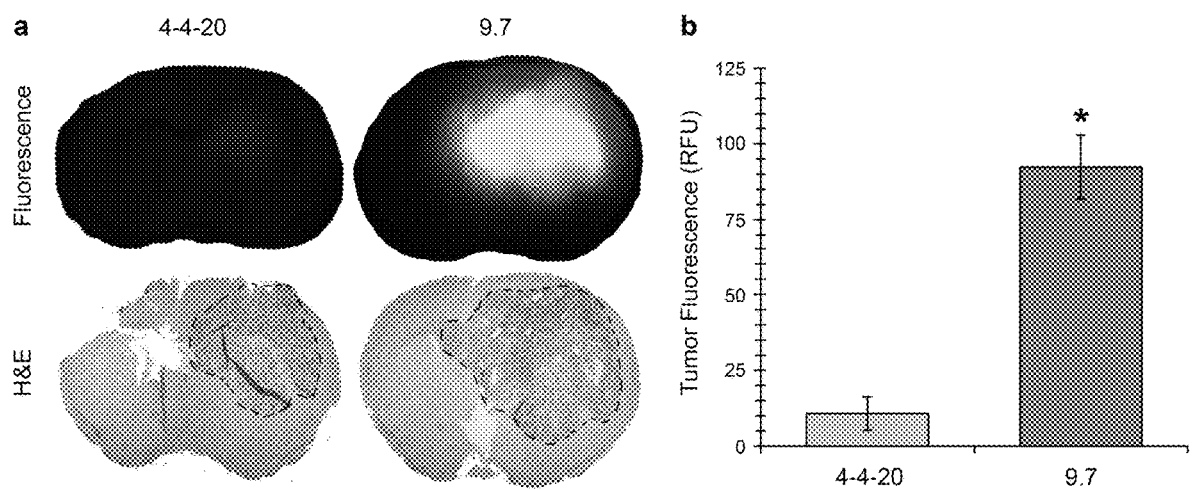
FIGS. 5A-5B. Purified near-infrared VH-9.7 localizes to human 22 GSC orthotopic xenografts. (a) Representative near-infrared fluorescent images captured from ex vivo coronal brain sections of orthotopic 22 GSC tumor xenografts in mice. Tumor area (dotted line) was identified using H&E counterstaining. (b) Tumor fluorescent signal was significantly higher in VH-9.7 injected mice compared to control scFv-4-4-20 (*: p<0.05, n≥2 replicates, minimum of 2 independent animal experiments). Error bars indicate S.E.M. RFU: relative fluorescent units.

To avoid any bias in isolating GSC with currently known markers, GSC lines were agnostically enriched from patient GBM tumors as spheres in minimal defined stem cell media for biopanning screening[22,32]. Validated for high efficiency tumor initiation after brain implantation in NOD-SCID mice, each GSC line recapitulates clinicopathological hallmark of GBM ranging from highly invasive to mass forming lesions[22]. Since all five patient-derived lines express a heterogeneous array of neural lineage markers, including low expression of CD133 in 44 and 99 GSC[22], it was unexpected to observe broad GSC-selective labeling with the identified VH-9.7 antibody (FIG. 2; FIG. 3b). Although all tested GSC lines were positively labeled by VH-9.7, the more invasive 33, 44, and 99 GSC lines exhibited higher antigenic signal than 12.1 and 22 GSC that generate less invasive xenografts. It is also notable that the VH-9.7 antibody was identified from biopanning with the 22 GSC line. The inverse expression of CD133 and VH-9.7 antigen suggests that they are not synonymous. Importantly, direct in vivo labeling of tumor xenografts (FIG. 4; FIG. 5) and positive presence in multiple patient-derived GSC suggest that VH-9.7 antigen is probably not an artifact of in vitro cell culture. Future experiments are planned to identify the cognate antigen of VH-9.7[28], residues involved with GSC binding specificity, and explore the tumor-initiating capacity and efficiency of VH-9.7-binding and VH-9.7 non-binding cells via serial implantation into brains of NOD-SCID mice[6]. Validation with these assays may provide a tool to identify and isolate GSC in addition to CD133, CD15, or marker-independent autofluorescence[6-8].

Presumably due to the heterogeneity of GBM[33] and GSC[22], seven rounds of biopanning screening were required to observe enrichment on 22 GSC (FIG. 1b). The extensive number of rounds needed for enrichment raises the possibility of yeast gain-of-function genomic alterations that may enhance non-specific binding; however, we observed that GSC binding required appropriate induction of yeast scFv or VH expression after round 9 and is absent without induction of scFv or VH expression (FIG. 6e). Similarly, phage antibody libraries theoretically require one round of screening[34], yet when challenged with heterogeneous GBM sphere cells, three rounds were necessary via fluorescence-activated cell sorting (FACS)[11].

Further, negative screens on co-cultured hNSC, NHA and 22T demonstrated VH-9.7 binding specificity for GSC, and also resulted in a richer diversity of binders that were not observed in the pools recovered after positive screens alone. Subtractive screens with yeast antibody libraries have been reported before[35,36], however, our cataloguing of clone discovery frequency and percent depletion in each round provide additional evidence for the benefits of this strategy. There was increased incidence of cell line-selective clones recovered in these pools (FIG. 8b) which were not observed in the non-depleted pools. Clones scFv-S.6.3, -S.6.4, and -S.8.4 were differentially selective to various GSC classes with reduced binding to hNSC and NHA. On the other hand, we hypothesize that antibodies that had broad coverage among all GSC invasiveness classes, such as shown with VH-9.7, scFv-3.107, scFv-3.150 and scFv-3.160, were presumably depleted by subtraction screening. Patient-specific scFv and VH clones will also be useful to continue exploring and characterizing GBM heterogeneity with respect to differential clinical survival.

In vivo localization of soluble VH-9.7 to focal 22 GSC xenografts was not surprising. Recent evidence suggests that systemic administration of bispecific T cell engaging scFv against EGFRvIII-positive U87 GBM xenografts resulted in up to 75% durable tumor control rates[37]. This suggests that scFv-based targeting platforms are potentially small enough to permeate through the partially disrupted tumor BBB in GBM. However, many central nervous system neoplasms exhibit heterogeneous permeability for smaller therapeutic molecules like paclitaxel and doxorubicin, with only a small fraction of lesions showing quantifiable uptake[38].

Highly infiltrative 44 GSC-derived xenografts, which are not easily visualized by gadolinium-enhanced T1 MRI and may have a less permeable or intact tumor BBB, may not be readily localized via VH-9.7. This suggests the need for other strategies to solve the formidable challenge of imaging and targeting of highly invasive GSC[23,39-43]. Intracarotid infusion of hypertonic solutions (such as mannitol and arabinose) or high frequency ultrasound with microbubbles[44] may be used to disrupt intact BBB and provide an opportunity to enhance scFv localization to invasive tumor cells in brain parenchyma[45,46]. Future experiments will explore the utility of VH-9.7 and other candidate antibodies for diagnostic and therapeutic targeting of GSC, including radiolabeled antibodies[47], bispecific BBB-penetrating antibodies[42], antibody-drug conjugates[48], bispecific T-cell engaging antibodies[49], and bioengineered immune cells such as chimeric antigen receptor T cells[50,51].

In conclusion, we describe a high-throughput method for identifying cell type-selective scFv and VH antibodies. VH-9.7 was used as a research tool and immunodiagnostic to identify GSC in vitro and in vivo. Further development of the diagnostic and therapeutic potential of the discovered scFv and VH antibodies are underway to target therapeutically resistant GBM cells.

Methods

All experiments were performed in accordance with relevant institutional guidelines and regulations.

Cell culture. All studies were performed with approval from the University of Wisconsin-Madison Institutional Review Board (IRB 2012-0024) with informed consent obtained from patients, and with approval from the UW-Madison Animal Care and Use Committee (M02223). Marker-neutral isolation of GSC lines from surgical specimens was performed using our previously reported protocols.[5,22,32,52-54] Cell lines were checked for *mycoplasma* contamination every 6 months (Lonza MycoAlert #LT07-218). Briefly, tumor tissue was collected directly from the University of Wisconsin Hospitals and Clinics operating room, weighed, coarsely minced with a scalpel blade, and subsequently chopped 2× at 200 μm using a tissue chopper (Sorvall TC-2 Smith-Farquahar). Chopped tissue was directly plated in suspension or on laminin (0.01 mg/mL for 3 hours at 37° C.)[27], and cultured in passaging medium: 70% Dulbecco Modified Eagle Medium (DMEM)-high glucose, 30% Ham's F12, 1×B27 supplement, 5 μg/mL heparin, penicillin-streptomycin-amphotericin (PSA), supplemented with 20 ng/ml each of human recombinant epidermal growth factor (EGF) and basic fibroblast growth factor (bFGF)[52]. Cultures were passaged approximately every 7-14 days by tissue chopping 2× at 100 μm or detached with Accutase (Millipore) before plating onto freshly coated laminin flasks. GSC lines derived from distinct patients were numbered as follows: GSC lines 12.1, 22, 33, and 44 were cultured in suspension, whereas 99 was cultured on laminin, "each number corresponds to a different anonymous patient source."

Each GSC line was validated for self-renewal by neurosphere formation, multipotency, tumor initiation, and serial implantation at high efficiency in NOD-SCID mice (The Jackson Laboratory) before experiments were performed[21,22]. Standard serum conditions were used to maintain patient-matched 22T, 33T, 99T GBM tumor lines along with traditional U251, U87, NHA (DMEM, 10% fetal bovine serum, 1% antibiotics) (Invitrogen). In most studies, GSC were compared to hNSC, a kind gift from Dr. Clive Svendsen, and maintained as previously described[52]. Establishing and cryopreservation of cell cultures ranged from passage 1-10. Cells used for experiments ranged from passage 20-25.

Growth and induction of scFv library. The nonimmune human scFv library harbored in the EBY100 yeast display strain (GAL1-AGA1::URA3 ura3-52 trp1 leu2Δ1 his3Δ200 pep4::HIS2 prb1Δ1.6R can1 GAL) was grown at 30° C. in 500 mL of SD-CAA (20.0 g/L dextrose, 6.7 g/L yeast nitrogen base, 5.0 g/L casamino acids, 10.19 g/L Na$_2$HPO$_4$·7H$_2$O, 8.56 g/L NaH$_2$PO$_4$·H$_2$O) plus 50 μg/mL kanamycin for 24 hours (OD$_{600}$~1)[14,18]. Yeast at 10-fold excess of the library diversity (5×10$^9$) were subsequently induced in 500 mL SG-CAA medium (same as SD-CAA except dextrose replaced by galactose) at 20° C. for 22 hours prior to biopanning against cell monolayers.

Biopanning of scFv library against GSC monolayers. In suspension 22 GSC spheres were enzymatically dissociated with Accutase™ and seeded as single cells onto poly-L-lysine and laminin 6-well plates at a density of 10$^7$ cells per well 12 hours prior to incubation with antibody-displaying yeast. At 10-fold excess of the library size (5×10$^9$ yeast), induced yeast were washed twice with 0.01 M PBS, pH 7.4, supplemented with 1 mM CaCl$_2$, 0.5 mM Mg$_2$SO$_4$ and 0.1% bovine serum albumin (BSA) (wash buffer) and the yeast mixture was added dropwise onto 126 cm$^2$ of GSC cell monolayer to ensure even distribution at a density of 4×10$^7$ yeast/cm$^2$ for the first round of biopanning and monolayer surface area was proportionally decreased for subsequent biopanning rounds as the library diversity reduced (FIG. 6a), described previously[18]. Since the pool diversity was greatly reduced after the 1$^{st}$ round, the yeast panning density was lowered to 4×10$^6$ yeast/cm$^2$, and the GSC area was reduced to 50.2 cm$^2$ for round 2 and 25.1 cm$^2$ for rounds 3-9. The monolayers were incubated at 4° C. for 2 hours on a rotating platform (30 revolutions/minute) to allow antibody-displaying yeast to contact and bind the GSC surface. The washing strategy was optimized to recover a model scFv that binds to RBE4 cells with nanomolar apparent affinity[17,18]. The resulting method involved washing the GSC layers with ice cold wash buffer by gently rocking the plate 25×, rotating the plate 5× (repeated 2×), and rotating the plate 10×. The washing supernatant was removed after each step and replaced with fresh wash buffer. After the washing steps, 1 mL of wash buffer was added into each well and all cells were scraped off the plate and pooled together. The yeast/GSC cell mixture was resuspended in 5 mL kanamycin-supplemented SD-CAA and grown at 30° C. overnight to OD$_{600}$~1 followed by SG-CAA induction for 20 hours at 20° C. for the subsequent round of biopanning. In parallel, a small fraction of the recovered cells were plated on SD-CAA-supplemented agar plates to quantify the number and fractional recovery of yeast cells after each round. Biopanning proceeded for 9 rounds to determine the extent of enrichment and percent yeast recovery. To confirm that the yeast-GSC interactions were scFv-based, pooled clones collected after round 9 were amplified overnight in SD-CAA at 30° C., and half the culture was then induced in SG-CAA at 20° C. for 20 hours, to assess scFv-dependent binding of 22 GSC (FIG. 6e).

Negative screen biopanning on hNSC, NHA and 22T co-culture. Negative or subtraction screens were performed by creating a co-culture of dissociated single cells of hNSC, NHA and 22T seeded at 10$^7$ cells per well in a 6-well poly-L-lysine and laminin coated plate overnight in minimal stem cell passaging media[52]. Yeast-displaying antibody pools resulting from biopanning rounds 6, 7, 8 and 9 were induced in SG-CAA for 20 hours at 20° C. and subjected to the abovementioned biopanning screening protocol on the co-cultured cells. However, the subtracted pools of unbound yeast were recovered after each washing step. A small aliquot of recovered yeast was plated on SD-CAA agar plates to calculate the percent depletion of the negative screen. After a diverse pool of clones was identified in negatively screened round S.6, it was later amplified in SD-CAA overnight and re-screened on 22 GSC to enrich for GSC-preferential scFv.

Figure 7:
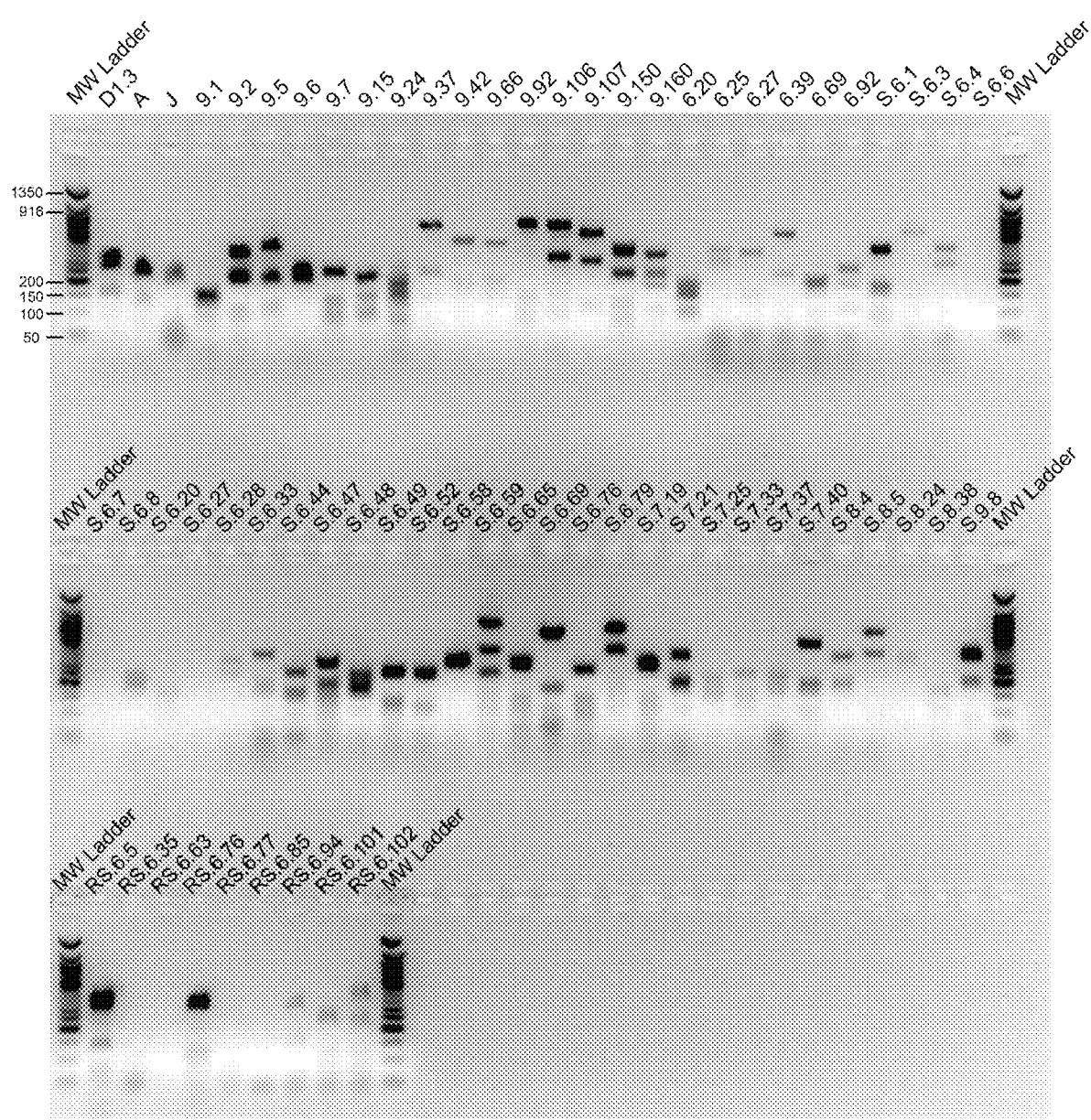
FIG. 7. Unique clones after selective screening. Unique clones discovered by plasmid isolation, PCR and BstNI restriction enzyme digest revealing different patterns on DNA gel electrophoresis. 62 unique scFv or VH clones were isolated out of 598 total yeast screened. Clones were isolated from round 6, 9, S.6, S.7, S.8, S.9, and RS.6. MW=Molecular Weight.

Restriction digest analysis of scFv clones. Plasmids encoding the identified scFv were recovered from individual yeast clones isolated from the various screened pools using the Zymoprep yeast miniprep kit (Zymo Research) and amplified by PCR using the following primers: PNL6 Forward (5'-GTACGAGCTAAAAGTACAGTG-3') and PNL6 Reverse (5'-TAGATACCCATACGACGTTC-3'). Subsequently, 20 μL of PCR product was used for BstNI (New England Biolabs) restriction digest at 60° C. for 14 hours. The digested products were resolved on a 2.5% high resolution agarose gel for unique scFv clone identification (FIG. 7; FIG. 12). Clones were named according to the screening round in which they were first discovered. "Different" clones represent diversity within a round. "Unique" clones represent the 62 antibodies with distinctive BstNI digestion patterns over all the sampled screening rounds.

Differential microscopic screening and scoring of unique yeast clones. Twelve human cell lines (NHA; hNSC; 12.1, 22, 33, 44, & 99 GSC; 22, 33, & 99 T; U251, & U87) were seeded at $10^5$ cells per well in a 96-well plate overnight in their respective stem media or serum-containing media. Non-serum cultures required a laminin-coated surface for adherence. Each of the 62 unique yeast clones tested was induced in 5 mL SG-CAA at 20° C. Clonal preparations of $10^6$ antibody-displaying yeast cells were allowed to incubate with each of the 12 cell lines in 200 µL of wash buffer for 2 hours at 4° C. on a rotating platform. Plates were gently washed three times with 100 µL of wash buffer with a multichannel pipette for uniformity. Light microscopy was then used to assess the binding capacity of the scFv yeast clones to each cell line and given a qualitative score from 0 to 3 (no binding to high binding) (FIG. 8a). scFv-D1.3 (anti-lysozyme)[29] and scFv-J (anti-NCAM)[28] were used as negative and positive controls, respectively.

VH-9.7 DNA sequencing. The VH-9.7 encoding plasmid was recovered using the Zymoprep yeast miniprep kit (Zymo Research) and sequenced with the Gal1-10 (5'-CAACAAAAAATTGTTAATATACCT-3') and alpha terminator primers (5'-GTTACATCTACACTGTTGTTAT-3') (UW-Madison Biotechnology Center). The sequence was then analyzed by IgBLAST (NCBI) to identify the human germline origin (FIG. 6-12).

ScFv and VH secretion and purification. The open reading frame for VH-9.7 was isolated from the PCR product used for BstNI typing by NheI-HindIII restriction digest and subcloned into an scFv yeast secretion vector (pRS316-GAL) that has been used extensively for scFv secretion[17,30]. The resultant pRS316-GAL-VH-9.7 plasmid was then transformed into YVH10, a yeast secretion strain overexpressing protein disulfide isomerase. Yeast harboring the pRS316-GAL-VH-9.7 secretion vector were grown in minimal SD medium (2% dextrose, 0.67% yeast nitrogen base) supplemented with 2×SCAA amino acids (190 mg/L Arg, 108 mg/L Met, 52 mg/L Tyr, 290 mg/L Ile, 440 mg/L Lys, 200 mg/L Phe, 1260 mg/L Glu, 400 mg/L Asp, 480 mg/L Val, 220 mg/L Thr, 130 mg/L Gly, 20 mg/L tryptophan lacking leucine and uracil) at 30° C. for 72 hours. Subsequently, scFv and VH secretion was induced at 20° C. for 72 hours in SG-SCAA (dextrose substituted by galactose) with 1 mg/ml BSA as a non-specific carrier. For experiments requiring purified scFv and VH, Ni-NTA columns (Qiagen) were used to purify the six histidine-tagged scFv and VH from 50 mL or 1 L batches as described previously[55]. The size, purity, and secretion yields of scFv and VH were analyzed by SDS-polyacrylamide gel electrophoresis (PAGE) with a 10-20% gradient tris-glycine gels followed by Coomassie blue staining. Purified protein concentrations were estimated by comparison to a series of ovalbumin standards (45 kDa) (0.05 mg/mL for scFv-4-4-20 and 0.29 mg/mL VH-9.7). In parallel, the SDS-PAGE resolved proteins were also blotted onto polyvinylidene difluoride membranes (PVDF) (Millipore) for Western blotting. The PVDF membrane was blocked at 4° C. overnight in TBST solution (8 g/L NaCl, and 0.1% Tween-20, buffered to pH 7.6 with 20 mM Tris) supplemented with 5% nonfat milk and probed with 1 µg/mL 9E10 anti c-Myc antibody (Pierce) followed by an anti-mouse IgG horse radish peroxidase conjugate (Thermo Scientific). Immunocomplex detection was accomplished using Supersignal West Pico Substrate (Thermo Scientific) chemiluminescence with multiple time point exposures to CL-XPosure Film (Thermo Scientific) evaluated by ImageJ (NIH) software for quantification.

Size exclusion chromatography. VH-9.7 was produced using a secretion strategy and purified using Ni-NTA resin (Roche), as previously described[15,56,57]. Eluted fractions were pooled and run over a TSKgel G3000SWXL (Tosoh) HPLC column using an Agilent 1200 HPLC system[58]. Proteins were detected by monitoring absorbance at 280 nm and collected using an automated fraction collector. A protein standard ranging from 670-14 kDa (Sigma) was used to generate the retention curved to determine size of eluted proteins. Fractions from an entire 9.7 size exclusion chromatography run were analyzed, via western blot, for the anti-c-Myc tag to determine peaks that contain VH-9.7.

$K_d$ analysis. Secreted VH-9.7 was harvested and purified via Ni-NTA and then size exclusion chromatography, as described above. Monomeric VH-9.7 was then concentrated (Millipore, 3000 MWCO Concentrators) and the amount of protein was calculated via BCA assay (Pierce). VH-9.7 was then diluted to 1,000 nM, using conditioned media from 33 GSC cultures. A titration series was then created using 2-fold dilutions with 33 GSC conditioned media ranging from 1,000.00-1.94 nM.

33 GSC, grown as spheroids, were harvested, Accutased (Innovative Cell Technologies) for 5-10 minutes, then broken apart by gentle trituration. Next, the cells were pelleted and re-suspended in condition media. Re-suspended 33 GSC were mixed 1:1 with the above mentioned dilution series to generate final concentrations of 500-0.97 nM. Cells were incubated with VH-9.7 for 1 hour at 37° C., 5% $CO_2$ with intermittent shaking. After labeling with VH-9.7, the cells were pelleted, cooled on ice, and washed two times, for 5 minutes each wash, using a blocking buffer containing 1.5% goat serum and 2% BSA in PBS. Presence of bound VH-9.7 was detected by incubating cells with 1:100 dilution of anti-c-Myc (9E10, BioLegend) and 1:200 dilution of goat anti-mouse AF647 (Life Technologies) for one hour on ice in blocking buffer. After incubation, cells were washed three times, five minutes per wash, then analyzed on a FACSCalibur (BD). Data were quantified using FlowJo, and fit to a standard one site binding model, $M.F.I._{Bound}=(M.F.I._{range}*[VH-9.7])/([VH-9.7]+K_d$, using the GraphPad Prism software suite to determine the binding affinity for monomeric VH-9.7. Data were normalized and presented as means and S.E.M. as previously described[59].

GSC-selectivity analysis by flow cytometry. To determine GSC-selectivity (FIG. 3b), approximately $10^6$ live cells were labeled in suspension (200 µL of flow cytometry buffer, PBS+1% goat serum) at 125 nM of VH-9.7 for 1 hour at 4° C., predimerized with Ms-anti-c-Myc (9E10) antibody followed by anti-mouse IgG AlexaFluor 647 (1:100) (Invitrogen) in the same conditions. Geometric mean fluorescence intensity was monitored by FACSCalibur flow cytometer (Becton Dickinson) after gating for live cells with propidium iodide and used to quantitate fractional bound ligand. Geometric mean fluorescence intensity (MFI) of scFv-4-4-20 was used to normalize VH-9.7 signal and two tailed unpaired t-tests were used to demonstrate significance ($p<0.05$). Data represented as a ratio and S.E.M.

GSC orthotopic xenograft model. Tumor initiation capacity of human GSC was verified by orthotopic xenograft as previously described[6,22,32,60]. Briefly, 22 and 44 GSC were enzymatically dissociated to single cells and varying cell numbers ($10^2$-$10^6$) were suspended in 5 µL of PBS. Using a Hamilton syringe, GSC were stereotactically implanted into the right striatum of anesthetized NOD-SCID mice at 0.33 µl/min at the following coordinates referenced from bregma: 0 mm antero-posterior, +2.5 mm medio-lateral, and −3.5 mm dorso-ventral[60]. At either 3 months or onset of neurological symptoms, tumor formation was verified using magnetic resonance imaging (MRI). Mice were anesthetized, administered 10 mmol/kg of intra-peritoneal gadodiamide (Omniscan, GE Healthcare), for contrast-enhanced T1- and T2-weighted imaging in the UW-Madison small animal MRI scanner (Varian 4.7T). After MRI detection of tumor xenograft growth or when neurological symptoms were observed, implanted NOD-SCID mice were euthanized by perfusion fixation with 4% paraformaldehyde. Brains were then excised, embedded in paraffin, and processed for general histology. Human-specific nuclear mitotic apparatus protein (hNuMA) (Abcam, ab97585) immunohistochemistry was used to discriminate between mouse and human cells at a 1:100 dilution, as previously described[22].

For flow cytometric identification of human GSC-derived tumor xenograft cells (n=6) (FIG. 4), mice were sacrificed when moribund, perfused with PBS, and brains were removed to excise the region of tumor implantation in the striatum. Recovered GSC-mouse brain tissue was broken down to single cells, as described above with human brain tumors, and labeled with 125 nM of predimerized scFv-4-4-20 or VH-9.7 (not randomized or blinded). For experiments to determine human specificity of xenografts (n=3) (FIG. 10), prior to scFv labeling, Ms-anti-human nuclei (HuNu) (Millipore, MAB1281) at 1:100 was incubated for 1 hour at 4° C. in permeabilizing 0.1% triton-X-100 flow cytometry buffer. Human specific nuclei were detected with Gt-anti-Ms AlexaFluor 488 (1:100) (Invitrogen). Next, VH-9.7 (25 µg/mL) was predimerized with an AlexaFluor 647 (1:1 molar ratio) conjugated version of 9E10 (Santa Cruz Biotechnology Inc., sc40 AF647) so it would not conflict with HuNu secondary labeling of a mouse antibody and used to label brain tumor. After flow cytometry, scFv-labeled cells were counterstained with DAPI (Invitrogen, MP01306) at 300 nM in PBS for 5 minutes, mounted onto slides with ProLong Gold antifade reagent (Invitrogen, P36930), and imaged using confocal microscopy (Nikon A1RSi). Z-stack projection images were compiled to appreciate depth and coverage of VH-9.7 surface labeling. All flow cytometry was analyzed using FlowJo v10.0.6.

Near-infrared fluorescence imaging of 22 GSC orthotopic xenografts. Near-infrared fluorescence imaging (NIRF) was performed with conjugates of cetuximab, scFv-4-4-20, and VH-9.7 with IRDye 800CW-NHS ester (LI-COR Biosciences Co.) at a 1:1 molar ratio, as previously described[61]. Briefly, 800CW-NHS dissolved in DMSO (25 mg/ml) was combined with IgG, scFv, or VH (1:1 molar ratio) in PBS (pH 8.5) for 2 hours at room temperature. The resulting solution was sterile filtered through Millipore Ultrafree Centrifugal Filters (0.65 µm). 800CW-labeled IgG, scFv, or VH were injected via the tail vein at a dose of 300 pmol per mouse harboring 22 GSC xenografts. Dorsal coats of mice were shaved and imaged at 0, 0.5, 1, and 2 hours post-injection to determine the optimal differential signal between scFv-4-4-20 and VH-9.7 with the IVIS Spectrum Pre-Clinical In Vivo Imaging System (Caliper Life Sciences). Under 2% isoflurane in $O_2$, mice were visualized with 745 nm excitation and 800, 820, and 840 nm emission spectra, collecting radiance (photons/second/$cm^2$/steradian) for approximately 1 minute at each time point. Near-infrared signal appeared highest in the animals' right cerebral hemisphere 30 minutes after injection and decayed to baseline after 2 hours. One week later, mice were re-injected with soluble IgG, scFv, or VH, and sacrificed at 30 minutes post-injection by intracardiac PBS perfusion to remove blood-borne, unbound IgG, scFv, or VH. Brains were then harvested and fixed in 4% paraformaldehyde for 24 hours. Coronal cross-sections were made at the coordinates of tumor implantation and imaged ex vivo using a NIRF scanning system (800 nm channel, Odyssey, LI-COR Biosciences). Resultant fluorescent brain scans were back-ground-corrected by subtracting mean signal of the contralateral striatum from the entire brain. Brains were then histologically processed and counterstained with hematoxylin and eosin (H&E). Tumor area was defined using H&E, and the mean fluorescent intensity of the tumor area determined using Photoshop (version CS6, Adobe Systems).

Example 2: Tumor Targeting of scFv

Figure 13:
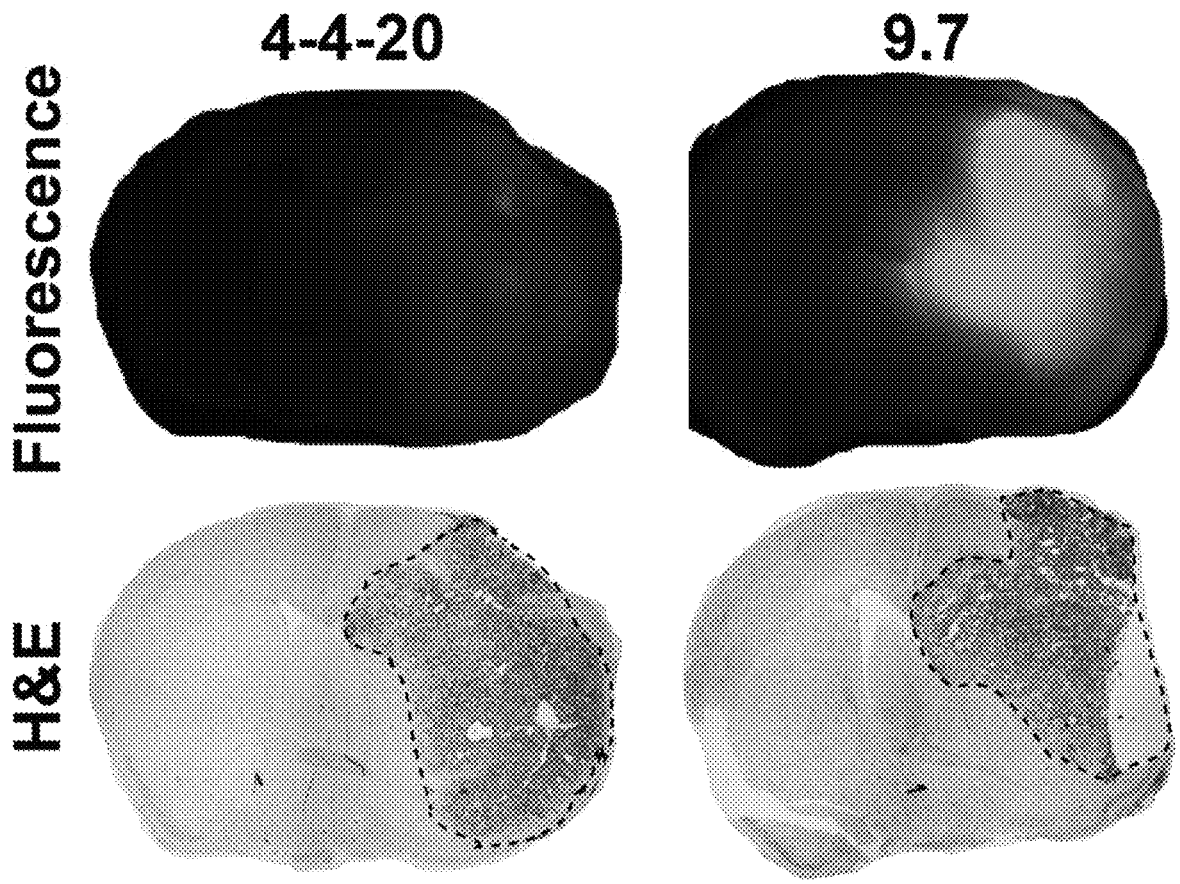
FIG. 13. Purified near-infrared VH-9.7 localizes to GL261 mouse GBM orthotopic xenografts. Representative near-infrared fluorescent images captured from ex vivo coronal brain sections of orthotopic GL261 mouse GBM xenografts in mice. Tumor area (dotted line) was identified using H&E counterstaining.

Tumor targeting potential of VH9.7 was tested in an additional orthotopic brain tumor model using GL261 mouse GBM line (FIG. 13). VH9.7 and non-targeting control scFv 4-4-20 were tagged with IR800 near-infrared dye and administered via intravenous injection to mice harboring GL261-derived orthotopic GBM (same methods as Zorniak et al., 2017, PMID: 29158489). Extensive and tumor-specific labeling was observed in VH9.7 administered mice compared to scFv 4-4-20 (control antibody). It is important to note that GL261 is a mouse GBM line; therefore, these data suggest VH9.7's tumor targeting ability and possible antigen conservation across human and mouse gliomas.

REFERENCES

1 Stupp, R. et al. Radiotherapy plus concomitant and adjuvant temozolomide for glioblastoma. *N Engl J Med* 352, 987-996, doi:352/10/987 (2005).

2 Stupp, R. et al. Maintenance Therapy With Tumor-Treating Fields Plus Temozolomide vs Temozolomide Alone for Glioblastoma: A Randomized Clinical Trial. *JAMA: the journal of the American Medical Association* 314, 2535-2543, doi:10.1001/jama.2015.16669 (2015).

3 Bao, S. et al. Glioma stem cells promote radioresistance by preferential activation of the DNA damage response. *Nature* 444, 756-760, doi:10.1038/nature05236 (2006).

4 Liu, G. et al. Analysis of gene expression and chemoresistance of CD133+ cancer stem cells in glioblastoma. *Molecular cancer* 5, 67, doi:10.1186/1476-4598-5-67 (2006).

5 Clark, P. A. et al. Activation of multiple ERBB family receptors mediates glioblastoma cancer stem-like cell resistance to EGFR-targeted inhibition. *Neoplasia* 14, 420-428 (2012).

6 Singh, S. K. et al. Identification of human brain tumour initiating cells. *Nature* 432, 396-401, doi:10.1038/nature03128 (2004).

7 Son, M. J., Woolard, K., Nam, D. H., Lee, J. & Fine, H. A. SSEA-1 is an enrichment marker for tumor-initiating cells in human glioblastoma. *Cell stem cell* 4, 440-452, doi:10.1016/j.stem.2009.03.003 (2009).

8 Clement, V. et al. Marker-independent identification of glioma-initiating cells. *Nature methods* 7, 224-228, doi: 10.1038/nmeth.1430 (2010).

9 Chen, R. et al. A hierarchy of self-renewing tumor-initiating cell types in glioblastoma. *Cancer cell* 17, 362-375, doi:10.1016/j.ccr.2009.12.049 (2010).

10 Pointer, K. B., Clark, P. A., Zorniak, M., Alrfaei, B. M. & Kuo, J. S. Glioblastoma cancer stem cells: Biomarker and therapeutic advances. *Neurochem Int* 71, 1-7, doi: 10.1016/j.neuint.2014.03.005 (2014).

11 Zhu, X. et al. Identification of internalizing human single-chain antibodies targeting brain tumor sphere cells. *Molecular cancer therapeutics* 9, 2131-2141, doi: 10.1158/1535-7163.MCT-09-1059 (2010).

12 Beck, S. et al. Identification of a peptide that interacts with Nestin protein expressed in brain cancer stem cells. *Biomaterials* 32, 8518-8528, doi: 10.1016/j.biomaterials.2011.07.048 (2011).

13 Kim, Y. et al. Aptamer Identification of Brain Tumor-Initiating Cells. *Cancer research* 73, 4923-4936, doi:10.1158/0008-5472.CAN-12-4556 (2013).

14 Feldhaus, M. J. et al. Flow-cytometric isolation of human antibodies from a nonimmune *Saccharomyces cerevisiae* surface display library. *Nature biotechnology* 21, 163-170, doi:10.1038/nbt785 (2003).

15 Shusta, E. V., Holler, P. D., Kieke, M. C., Kranz, D. M. & Wittrup, K. D. Directed evolution of a stable scaffold for T-cell receptor engineering. *Nature biotechnology* 18, 754-759, doi:10.1038/77325 (2000).

16 Richman, S. A. et al. Development of a novel strategy for engineering high-affinity proteins by yeast display. *Protein engineering, design & selection: PEDS* 19, 255-264, doi:10.1093/protein/gzl008 (2006).

17 Wang, X. X. & Shusta, E. V. The use of scFv-displaying yeast in mammalian cell surface selections. *Journal of immunological methods* 304, 30-42, doi:10.1016/j.jim.2005.05.006 (2005).

18 Wang, X. X., Cho, Y. K. & Shusta, E. V. Mining a yeast library for brain endothelial cell-binding antibodies. *Nature methods* 4, 143-145, doi:10.1038/nmeth993 (2007).

19 Boder, E. T. & Wittrup, K. D. Yeast surface display for directed evolution of protein expression, affinity, and stability. *Methods in enzymology* 328, 430-444 (2000).

20 Liu, H., Styles, C. A. & Fink, G. R. *Saccharomyces cerevisiae* S288C has a mutation in FLOG, a gene required for filamentous growth. Genetics 144, 967-978 (1996).

21 Clark, P. A., Treisman, D. M., Ebben, J. & Kuo, J. S. Developmental signaling pathways in brain tumor-derived stem-like cells. *Dev Dyn* 236, 3297-3308, doi:10.1002/dvdy.21381 (2007).

22 Zorniak, M. et al. Differential expression of 2',3'-cyclic-nucleotide 3'-phosphodiesterase and neural lineage markers correlate with glioblastoma xenograft infiltration and patient survival. *Clinical cancer research: an official journal of the American Association for Cancer Research* 18, 3628-3636, doi:10.1158/1078-0432.CCR-12-0339 (2012).

23 Weichert, J. P. et al. Alkylphosphocholine analogs for broad-spectrum cancer imaging and therapy. *Science translational medicine* 6, 240ra275, doi:10.1126/scitranslmed.3007646 (2014).

24 Zorniak, M., Clark, P. A. & Kuo, J. S. Myelin-forming cell-specific cadherin-19 is a marker for minimally infiltrative glioblastoma stem-like cells. *J Neurosurg* 122, 69-77, doi:10.3171/2014.9.JNS132373 (2015).

25 Clark, P. A. et al. Resveratrol targeting of AKT and p53 in glioblastoma and glioblastoma stem-like cells to suppress growth and infiltration. *J Neurosurg*, 1-13, doi:10.3171/2016.1.JN5152077 (2016).

26 Pointer, K. B. et al. Non-torsadogenic human Ether-a-go-go Related Gene (hERG) inhibitors are associated with better survival for high hERG-expressing glioblastoma patients. *Clinical cancer research: an official journal of the American Association for Cancer Research*, doi:10.1158/1078-0432.CCR-15-3169 (2016).

27 Pollard, S. M. et al. Glioma stem cell lines expanded in adherent culture have tumor-specific phenotypes and are suitable for chemical and genetic screens. *Cell stem cell* 4, 568-580, doi:S1934-5909(09)00149-0 (2009).

28 Cho, Y. K., Chen, I., Wei, X., Li, L. & Shusta, E. V. A yeast display immunoprecipitation method for efficient isolation and characterization of antigens. *Journal of immunological methods* 341, 117-126, doi:10.1016/j.jim.2008.11.005 (2009).

29 VanAntwerp, J. J. & Wittrup, K. D. Fine affinity discrimination by yeast surface display and flow cytometry. *Biotechnology progress* 16, 31-37, doi:10.1021/bp990133s (2000).

30 Shusta, E. V., Raines, R. T., Pluckthun, A. & Wittrup, K. D. Increasing the secretory capacity of *Saccharomyces cerevisiae* for production of single-chain antibody fragments. *Nature biotechnology* 16, 773-777, doi:10.1038/nbt0898-773 (1998).

31 Liu, J. K. et al. Phage display discovery of novel molecular targets in glioblastoma-initiating cells. *Cell Death Differ* 21, 1325-1339, doi:10.1038/cdd.2014.65 (2014).

32 Lee, J. et al. Tumor stem cells derived from glioblastomas cultured in bFGF and EGF more closely mirror the phenotype and genotype of primary tumors than do serum-cultured cell lines. *Cancer cell* 9, 391-403, doi:10.1016/j.ccr.2006.03.030 (2006).

33 Homma, T. et al. Correlation among pathology, genotype, and patient outcomes in glioblastoma. *Journal of neuropathology and experimental neurology* 65, 846-854, doi:10.1097/01.jnen.0000235118.75182.94 (2006).

34 Hoogenboom, H. R. Selecting and screening recombinant antibody libraries. *Nature biotechnology* 23, 1105-1116, doi:10.1038/nbt1126 (2005).

35 Lipovsek, D. et al. Selection of horseradish peroxidase variants with enhanced enantioselectivity by yeast surface display. *Chemistry & biology* 14, 1176-1185, doi:10.1016/j.chembiol.2007.09.008 (2007).

36 Ackerman, M. et al. Highly avid magnetic bead capture: an efficient selection method for de novo protein engineering utilizing yeast surface display. *Biotechnology progress* 25, 774-783, doi:10.1002/btpr.174 (2009).

37 Choi, B. D. et al. Systemic administration of a bispecific antibody targeting EGFRvIII successfully treats intracerebral glioma. *Proceedings of the National Academy of Sciences of the United States of America* 110, 270-275, doi:10.1073/pnas.1219817110 (2013).

38 Lockman, P. R. et al. Heterogeneous blood-tumor barrier permeability determines drug efficacy in experimental brain metastases of breast cancer. *Clinical cancer research: an official journal of the American Association for Cancer Research* 16, 5664-5678, doi:10.1158/1078-0432.CCR-10-1564 (2010).

39 Swanson, K. I. et al. Fluorescent cancer-selective alkylphosphocholine analogs for intraoperative glioma detection. *Neurosurgery* 76, 115-123; discussion 123-114, doi:10.1227/NEU.0000000000000622 (2015).

40 Clark, P. A. et al. Analysis of Cancer-Targeting Alkylphosphocholine Analogue Permeability Characteristics Using a Human Induced Pluripotent Stem Cell Blood-Brain Barrier Model. *Mol Pharm* 13, 3341-3349, doi:10.1021/acs.molpharmaceut.6b00441 (2016).

41 Zhang, R. R., Swanson, K. I., Hall, L. T., Weichert, J. P. & Kuo, J. S. Diapeutic cancer-targeting alkylphosphocholine analogs may advance management of brain malignancies. *CNS Oncol* 5, 223-231, doi:10.2217/cns-2016-0017 (2016).

42 Pardridge, W. M. Re-engineering therapeutic antibodies for Alzheimer's disease as blood-brain barrier penetrating bi-specific antibodies. *Expert Opin Biol Ther*, 1-14, doi:10.1080/14712598.2016.1230195 (2016).

43 Pardridge, W. M. CSF, blood-brain barrier, and brain drug delivery. *Expert Opin Drug Deliv* 13, 963-975, doi:10.1517/17425247.2016.1171315 (2016).

44 Liu, H. L. et al. Focused Ultrasound Enhances Central Nervous System Delivery of Bevacizumab for Malignant Glioma Treatment. *Radiology* 281, 99-108, doi:10.1148/radiol.2016152444 (2016).

45 Rapoport, S. I. Osmotic opening of the blood-brain barrier: principles, mechanism, and therapeutic applications. *Cellular and molecular neurobiology* 20, 217-230 (2000).

46 Liu, R., Martuza, R. L. & Rabkin, S. D. Intracarotid delivery of oncolytic HSV vector G47Delta to metastatic breast cancer in the brain. *Gene therapy* 12, 647-654, doi:10.1038/sj.gt.3302445 (2005).

47 Yang, Y. et al. Targeting CD146 with a 64Cu-labeled antibody enables in vivo immunoPET imaging of high-grade gliomas. *Proceedings of the National Academy of Sciences of the United States of America* 112, E6525-6534, doi:10.1073/pnas.1502648112 (2015).

48 Hamblett, K. J. et al. AMG 595, an Anti-EGFRvIII Antibody-Drug Conjugate, Induces Potent Antitumor Activity against EGFRvIII-Expressing Glioblastoma. *Molecular cancer therapeutics* 14, 1614-1624, doi:10.1158/1535-7163.MCT-14-1078 (2015).

49 Suryadevara, C. M. et al. Are BiTEs the "missing link" in cancer therapy? *Oncoimmunology* 4, e1008339, doi:10.1080/2162402X.2015.1008339 (2015).

50 Krenciute, G. et al. Characterization and Functional Analysis of scFv-based Chimeric Antigen Receptors to Redirect T Cells to IL13Ralpha2-positive Glioma. *Mol Ther* 24, 354-363, doi:10.1038/mt.2015.199 (2016).

51 Shiina, S. et al. CAR T Cells Targeting Podoplanin Reduce Orthotopic Glioblastomas in Mouse Brains. *Cancer Immunol Res* 4, 259-268, doi:10.1158/2326-6066.CIR-15-0060 (2016).

52 Svendsen, C. N. et al. A new method for the rapid and long term growth of human neural precursor cells. *J Neurosci Methods* 85, 141-152, doi:S0165-0270(98)00126-5 (1998).

53 Ignatova, T. N. et al. Human cortical glial tumors contain neural stem-like cells expressing astroglial and neuronal markers in vitro. *Glia* 39, 193-206, doi:10.1002/glia.10094 (2002).

54 Singh, S. K. et al. Identification of a cancer stem cell in human brain tumors. *Cancer research* 63, 5821-5828 (2003).

55 Hackel, B. J., Huang, D., Bubolz, J. C., Wang, X. X. & Shusta, E. V. Production of soluble and active transferrin receptor-targeting single-chain antibody using *Saccharomyces cerevisiae*. *Pharmaceutical research* 23, 790-797, doi:10.1007/s11095-006-9778-7 (2006).

56 Marshall, C. J. et al. An evolved Mxe GyrA intein for enhanced production of fusion proteins. *ACS Chem Biol* 10, 527-538, doi:10.1021/cb500689g (2015).

57 Huang, D., Gore, P. R. & Shusta, E. V. Increasing yeast secretion of heterologous proteins by regulating expression rates and post-secretory loss. *Biotechnol Bioeng* 101, 1264-1275, doi:10.1002/bit.22019 (2008).

58 Burns, M. L. et al. Directed evolution of brain-derived neurotrophic factor for improved folding and expression in *Saccharomyces cerevisiae*. *Applied and environmental microbiology* 80, 5732-5742, doi:10.1128/AEM.01466-14 (2014).

59 Tillotson, B. J., Cho, Y. K. & Shusta, E. V. Cells and cell lysates: a direct approach for engineering antibodies against membrane proteins using yeast surface display. *Methods* 60, 27-37, doi:10.1016/j.ymeth.2012.03.010 (2013).

60 Galli, R. et al. Isolation and characterization of tumorigenic, stem-like neural precursors from human glioblastoma. *Cancer research* 64, 7011-7021, doi:64/19/7011 (2004).

61 Yang, Y. et al. In vivo near-infrared fluorescence imaging of CD105 expression during tumor angiogenesis. *European journal of nuclear medicine and molecular imaging* 38, 2066-2076, doi:10.1007/s00259-011-1886-x (2011).

SEQUENCE LISTING STATEMENT

The application includes the sequence listing that is concurrently filed in computer readable form. This sequence listing is incorporated by reference herein.

```
SEQ ID NO: 1 Vh-9.7 without tag
A S Q V Q L V E S E A E V K K P G A S V K V S C K A S G Y S F T N Y Y M H
                                                      CDR1

W V R Q A P G Q G L E W M G L I D P S G T S T T Y A Q K F Q G R V T M T
                                  CDR2

R D T S A S T V Y M E L T S L R S E D T A M Y Y C V G E E S G S G S F S D
                                                  CDR3

W G Q G T L V T V S S G S A S A P

SEQ ID NO: 2 VH-9.7-CMYC-HIS6 Amino Acid Sequence:
A S Q V Q L V E S E A E V K K P G A S V K V S C K A S G Y S F T N Y Y M H
                                                      CDR1

W V R Q A P G Q G L E W M G L I D P S G T S T T Y A Q K F Q G R V T M T
                                  CDR2
```

R D T S A S T V Y M E L T S L R S E D T A M Y Y C <u>V G E E S G S G S F S D</u>
                                                         CDR3

W G Q G T L V T V S S G S A S A P <u>E O K L I S E E D L</u> <u>H H H H H H</u>
                                     CMYC              HIS6

SEQ ID NO: 3 CDR1 <u>G Y S F T N Y Y</u>

SEQ ID NO: 4 CDR2 <u>I D P S G T S T</u>

SEQ ID NO: 5 CDR3 <u>V G E E S G S G S F S D</u>

---

The invention claimed is:

1. An isolated antibody or fragment thereof able to selectively bind glioblastoma stem-like cells, wherein the antibody comprises a CDR1 domain comprising SEQ ID NO:3, a CDR2 domain comprising SEQ ID NO:4, and a CDR3 domain comprising SEQ ID NO:5.

2. The isolated antibody or antibody fragment of claim 1, wherein the antibody is selected from the group consisting of a humanized antibody, a single chain variable fragment (scFv) antibody, a single domain antibody, an antigen-binding fragment and a chimeric antibody.

3. The isolated antibody or fragment thereof of claim 1, wherein the antibody comprises the polypeptide sequence of SEQ ID NO: 1 or a sequence with at least 95% identity to SEQ ID NO:1.

4. The isolated antibody or fragment thereof of claim 1, wherein the antibody is directly or indirectly linked to a tag, or agent or cell.

5. The isolated antibody or fragment thereof of claim 4, wherein the tag or agent is selected from the group consisting of a therapeutic agent, an imaging agent, a detection agent, a immunological therapeutic construct, and a combination thereof.

6. The isolated antibody or fragment thereof of claim 4, wherein the agent is a single-step agent for detection and imaging.

7. The isolated antibody or fragment thereof of claim 4, wherein the tag is a purification tag.

8. The isolated antibody or fragment thereof of claim 4, where the antibody comprises the polypeptide sequence of SEQ ID NO:2 or a sequence with at least 95% identity to SEQ ID NO:2.

9. The isolated antibody or fragment thereof of claim 4, wherein the agent is a therapeutic agent.

10. The isolated antibody or fragment thereof of claim 9, wherein the therapeutic agent is a chemotherapeutic agent or immunomodulatory agent.

11. The isolated antibody of claim 4, wherein the agent is an imaging agent.

12. An isolated nucleic acid molecule encoding the antibody of claim 1.

13. A host cell able to express the isolated antibody of claim 1.

14. The cell of claim 13, wherein the host cell is selected from the group consisting of a yeast cell and a mammalian cell.

15. A composition comprising the isolated antibody of claim 1 and a pharmaceutically acceptable carrier.

16. A method of detecting glioblastoma stem-like cells in a sample, wherein the method comprises
contacting the sample with an antibody of claim 1, and detecting the binding of the antibody in the sample.

17. The method of claim 16, wherein the increase in binding of the antibody to the sample as compared to binding of the antibody to a control sample detects glioblastoma stem-like cells within the sample.

18. The method of claim 16, wherein the sample is an in vitro sample or an in vivo sample.

19. The method of claim 18, wherein the sample is a blood sample, a cerebral spinal fluid sample, or a tissue sample.

20. The method of detecting glioblastoma stem-like cells of claim 16, wherein the glioblastoma stem-like cell is in vivo in a subject suspected of having glioblastoma, and the contacting comprises administering the antibody to the subject wherein binding indicates glioblastoma stem-like cells within the subject.

21. The method of claim 20, wherein the antibody is directly labeled with a detection agent.

22. The method of claim 20, wherein the antibody is administered directly to the brain of a subject, by intrathecal injection or intravenously to the subject.

23. The method of claim 16, wherein the method comprises identifying glioblastoma stem-like cells within a brain tumor (a) by contacting a sample from a brain tumor of a subject with the antibody of claim 1; and (b) detecting the presence of glioblastoma stem-like cells, wherein the presence of the glioblastoma cells indicates the tumor is a glioblastoma.

24. The method of claim 23, wherein the method further comprises quantifying the amount of the glioblastoma stem-like cells within a brain tumor sample, wherein the presence of a higher percentage of glioblastoma stem-like cells within the brain tumor indicates more invasive or aggressive glioblastoma cancer.

25. A method of treating a subject with glioblastoma, the method comprising
administering an antibody able to bind glioblastoma stem-like cells of claim 1 directly or indirectly linked with a therapeutic agent or therapeutic cell in an effective amount to treat the glioblastoma.

26. The method of claim 25, wherein the treating is characterized by a reduction in the number of glioblastoma stem cells within the subject.

27. The method of claim 25, wherein the therapeutic agent is a chemotherapeutic agent.

28. The method of claim 25, wherein the therapeutic cell is a T-cell, a natural killer (NK) cell, or a natural killer T cell (NKT).

29. A method of targeting an agent to glioblastoma stem cells, the method comprising directly or indirectly linking the agent with an antibody of claim 1.

30. A kit for detecting glioblastoma stem-like cells, the kit comprising the antibody of claim 1 and instructions for use.

31. The kit of claim 30, wherein the kit further comprises a control.

32. A kit for treating glioblastoma, the kit comprising the antibody of claim 1 and instructions for use.

33. The method of claim 25, wherein the antibody is administered prior to surgery to remove or reduce the presence of glioblastoma cancer.

34. The method of claim 25, wherein the antibody is administered at least once after surgery as adjuvant maintenance therapy to reduce risk of glioblastoma recurrence.

* * * * *

UNITED STATES PATENT AND TRADEMARK OFFICE
CERTIFICATE OF CORRECTION

| | |
|---|---|
| PATENT NO. | : 11,780,932 B2 |
| APPLICATION NO. | : 16/754677 |
| DATED | : October 10, 2023 |
| INVENTOR(S) | : Michael Zorniak et al. |

It is certified that error appears in the above-identified patent and that said Letters Patent is hereby corrected as shown below:

In the Specification

Column 4, Line 11, "VII" should be --VH--.

Column 9, Line 60, "CD3" should be --CD3 ζ--.

Column 15, Line 47, "nanoparticles Van" should be --nanoparticles (B. Van--.

Column 26, Line 15, "VII" should be --VH--.

Column 27, Line 3, "VII" should be --VH--.

Column 33, Line 24, "VII" should be --VH--.

Column 37, Line 29, "FLOG" should be --FLO8--.

Column 37, Line 55, "10.3171/2016.1.JN5152077" should be --10.3171/2016.1.JNS152007--.

Signed and Sealed this
Twenty-third Day of April, 2024

Katherine Kelly Vidal
*Director of the United States Patent and Trademark Office*

SEQUENCE LISTING

<160> NUMBER OF SEQ ID NOS: 10

<210> SEQ ID NO 1
<211> LENGTH: 127
<212> TYPE: PRT
<213> ORGANISM: Artificial Sequence
<220> FEATURE:
<223> OTHER INFORMATION: Synthetic

<400> SEQUENCE: 1

Ala Ser Gln Val Gln Leu Val Glu Ser Glu Ala Glu Val Lys Lys Pro
1               5                   10                  15

Gly Ala Ser Val Lys Val Ser Cys Lys Ala Ser Gly Tyr Ser Phe Thr
            20                  25                  30

Asn Tyr Tyr Met His Trp Val Arg Gln Ala Pro Gly Gln Gly Leu Glu
        35                  40                  45

Trp Met Gly Leu Ile Asp Pro Ser Gly Thr Ser Thr Tyr Ala Gln
    50                  55                  60

Lys Phe Gln Gly Arg Val Thr Met Thr Arg Asp Thr Ser Ala Ser Thr
65                  70                  75                  80

Val Tyr Met Glu Leu Thr Ser Leu Arg Ser Glu Asp Thr Ala Met Tyr
                85                  90                  95

Tyr Cys Val Gly Glu Glu Ser Gly Ser Gly Ser Phe Ser Asp Trp Gly
            100                 105                 110

Gln Gly Thr Leu Val Thr Val Ser Ser Gly Ser Ala Ser Ala Pro
        115                 120                 125

<210> SEQ ID NO 2
<211> LENGTH: 143
<212> TYPE: PRT
<213> ORGANISM: Artificial Sequence
<220> FEATURE:
<223> OTHER INFORMATION: Synthetic

<400> SEQUENCE: 2

Ala Ser Gln Val Gln Leu Val Glu Ser Glu Ala Glu Val Lys Lys Pro
1               5                   10                  15

Gly Ala Ser Val Lys Val Ser Cys Lys Ala Ser Gly Tyr Ser Phe Thr
            20                  25                  30

Asn Tyr Tyr Met His Trp Val Arg Gln Ala Pro Gly Gln Gly Leu Glu
        35                  40                  45

Trp Met Gly Leu Ile Asp Pro Ser Gly Thr Ser Thr Tyr Ala Gln
    50                  55                  60

Lys Phe Gln Gly Arg Val Thr Met Thr Arg Asp Thr Ser Ala Ser Thr
65                  70                  75                  80

```
Val Tyr Met Glu Leu Thr Ser Leu Arg Ser Glu Asp Thr Ala Met Tyr
                85                  90                  95

Tyr Cys Val Gly Glu Glu Ser Gly Ser Gly Phe Ser Asp Trp Gly
            100                 105                 110

Gln Gly Thr Leu Val Thr Val Ser Ser Gly Ser Ala Ser Ala Pro Glu
        115                 120                 125

Gln Lys Leu Ile Ser Glu Glu Asp Leu His His His His His His
    130                 135                 140
```

<210> SEQ ID NO 3
<211> LENGTH: 8
<212> TYPE: PRT
<213> ORGANISM: Artificial Sequence
<220> FEATURE:
<223> OTHER INFORMATION: Synthetic

<400> SEQUENCE: 3

```
Gly Tyr Ser Phe Thr Asn Tyr Tyr
1               5
```

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

```
Ile Asp Pro Ser Gly Thr Ser Thr
1               5
```

<210> SEQ ID NO 5
<211> LENGTH: 12
<212> TYPE: PRT
<213> ORGANISM: Artificial Sequence
<220> FEATURE:
<223> OTHER INFORMATION: Synthetic

<400> SEQUENCE: 5

```
Val Gly Glu Glu Ser Gly Ser Gly Phe Ser Asp
1               5                   10
```

<210> SEQ ID NO 6
<211> LENGTH: 14
<212> TYPE: PRT
<213> ORGANISM: Artificial Sequence
<220> FEATURE:
<223> OTHER INFORMATION: Synthetic

<400> SEQUENCE: 6

```
Asn Tyr His Leu Glu Asn Glu Val Ala Arg Leu Lys Lys Leu
1               5                   10
```

<210> SEQ ID NO 7
<211> LENGTH: 21
<212> TYPE: DNA
<213> ORGANISM: Artificial Sequence
<220> FEATURE:
<223> OTHER INFORMATION: synthetic

<400> SEQUENCE: 7
gtacgagcta aaagtacagt g                                        21

<210> SEQ ID NO 8
<211> LENGTH: 20

```
<212> TYPE: DNA
<213> ORGANISM: Artificial Sequence
<220> FEATURE:
<223> OTHER INFORMATION: synthetic

<400> SEQUENCE: 8
tagataccca tacgacgttc                                              20

<210> SEQ ID NO 9
<211> LENGTH: 24
<212> TYPE: DNA
<213> ORGANISM: Artificial Sequence
<220> FEATURE:
<223> OTHER INFORMATION: synthetic

<400> SEQUENCE: 9
caacaaaaaa ttgttaatat acct                                         24

<210> SEQ ID NO 10
<211> LENGTH: 22
<212> TYPE: DNA
<213> ORGANISM: Artificial Sequence
<220> FEATURE:
<223> OTHER INFORMATION: synthetic

<400> SEQUENCE: 10
gttacatcta cactgttgtt at                                           22
```